United States Patent [19]

Ryan et al.

[11] Patent Number: 4,745,124

[45] Date of Patent: May 17, 1988

[54] ORALLY EFFECTIVE ANTI-HYPERTENSIVE AGENTS

[75] Inventors: James W. Ryan; Alfred Chung, both of Miami, Fla.

[73] Assignee: University of Miami, Coral Gables, Fla.

[21] Appl. No.: 515,474

[22] Filed: Jul. 20, 1983

Related U.S. Application Data

[63] Continuation-in-part of Ser. No. 295,589, Aug. 24, 1981, Ser. No. 156,749, Jun. 5, 1980, Ser. No. 145,772, May 2, 1980, Ser. No. 145,773, May 2, 1980, Ser. No. 146,107, May 2, 1980, Ser. No. 127,472, Mar. 5, 1980, Ser. No. 121,188, Mar. 3, 1980, Ser. No. 116,950, Jan. 30, 1980, Pat. No. 4,695,582, Ser. No. 64,897, Aug. 14, 1979, Ser. No. 64,898, Aug. 14, 1979, Ser. No. 64,899, Aug. 14, 1979, Ser. No. 64,900, Aug. 14, 1979, Ser. No. 64,901, Aug. 14, 1979, Ser. No. 64,902, Aug. 14, 1979, and Ser. No. 64,903, Aug. 14, 1979, said Ser. No. 295,589, is a continuation of Ser. No. 116,951, Jan. 30, 1980, abandoned, which is a continuation of Ser. No. 958,180, Nov. 6, 1978, abandoned, said Ser. No. 156,749, and Ser. No. 121,188, each is a continuation-in-part of Ser. No. 116,950, , Ser. No. 116,951, , Ser. No. 64,897, , Ser. No. 64,898, , Ser. No. 64,899, , Ser. No. 64,900, , Ser. No. 64,901, , Ser. No. 64,902, , Ser. No. 64,903, , Ser. No. 958,180, , and Ser. No. 941,289, Sep. 11, 1978, abandoned, said Ser. No. 156,749, is a continuation-in-part of Ser. No. 121,188, , said Ser. No. 116,950, is a continuation of Ser. No. 941,289.

[51] Int. Cl.[4] .................... A61K 31/40; A61K 31/41; C07D 207/00; C07D 211/72

[52] U.S. Cl. .................................. 514/362; 514/255; 514/308; 514/363; 514/423; 546/310; 548/531; 548/535

[58] Field of Search ............... 548/531, 535; 546/310; 514/362, 255, 308, 363, 423; 424/274

[56] References Cited

U.S. PATENT DOCUMENTS 4,483,861 11/1984 Iwao et al. ..................... 514/333

FOREIGN PATENT DOCUMENTS 0009898 4/1980 European Pat. Off. ........... 548/531

Primary Examiner—Delbert R. Phillips

[57] ABSTRACT

Novel thiolester compounds are disclosed which are orally effective angiotensin converting enzyme inhibitors useful in the treatment of mammalian hypertension. They have the formula, $$R_1-A_1-S-Z,$$

wherein Z denotes $-B-A_2$, $R_1$ is H or an acyl group, $A_1$ is a carboxylic acid containing at least one amino or imino -N-, $A_2$ is a carboxylic acid containing at least one amino or imino -N- or a lower alkyl ester or amide thereof, B is a 2-4 carbon backbone chain in mercapto linkage to S which includes a carbonyl or sulfonyl group joined in carboxamido or sulfonamido linkage, respectively, to $A_2$.

Preferably $A_2$ includes a 4-6 membered C-N ring or a 5 membered ring of one N, one S and 3 C atoms.

2 Claims, No Drawings

ORALLY EFFECTIVE ANTI-HYPERTENSIVE AGENTS

IDENTIFICATION OF PATENT APPLICATIONS

The present application is a continuation-in-part and consolidation of each of (a) our U.S. application Ser. No. 116,950, filed Jan. 30, 1980 now U.S. Pat. No. 4695582 which is a continuation of our U.S. application Ser. No. 941,289, filed Sept. 11, 1978, now abandoned;

(b) our U.S. application Ser. No. 295,589, filed Aug. 24, 1981 which is a continuation of our U.S. application Ser. No. 116,951, filed Jan. 30, 1980, now abandoned, which is in turn a continuation of our U.S. application Ser. No. 958,180, filed Nov. 6, 1978, now abandoned;

(c) each of our U.S. application Ser. Nos. 064,897; 064,898; 064,899; 064,900; 064,901; 064,902 and 064,903 which were filed Aug. 14, 1979;

(d) our U.S. application Ser. No. 121,188, filed Mar. 3, 1980, which is a continuation-in-part of all our applications identified in subparagraphs (a) and (c) hereof and both now abandoned applications identified in subparagraph (b) hereof;

(e) our U.S. application Ser. No. 127,472, filed Mar. 5, 1980;

(f) each of our U.S. application Ser. Nos. 145,772, 145,773 and 146,107, filed May 2, 1980, and (g) our U.S. application Ser. No. 156,749, filed June 5, 1980 which in its turn is a continuation-in-part of each of the applications identified in subparagraphs (a), (c) and (d) hereof, and of our applications Ser. No. 116,951 and Ser. No. 958,180 identified in subparagraph (b) above.

BACKGROUND OF THE INVENTION

As used herein, various symbols have the meaning assigned in the ensuing table:

Ala=alanine
Arg=arginine
Asp=aspartic acid
Boc=t-butyloxycarbonyl
Cpc=cyclopentane carbonyl
Cys=cysteine
Glu=glutamic acid
<Glu=pyro-L-glutamic acid
Gly=glycine
Hip=Hippuric acid (Benzoyl-glycine)
His=histidine
Ile=isoleucine
Leu=leucine
Lys=lysine
Met=methionane
Orn=ornithine
Phe=phenylalanine
Pro=proline
ΔPro=3,4-dehydroproline
Ser=serine
Thr=threonine
Thy=thyronine
Trp=tryptophan
Tyr=tyrosine
Val=valine
ACE=angiotensin converting enzyme
Hepes=N-2-hydroxyethylpiperazine-N'-2-enthanesulfonic acid Angiotensin converting enzyme (peptidyldipeptide hydrolase, hereinafter referred to as ACE) occupies a central role in the physiology of hypertension. The enzyme is capable of converting the decapeptide angiotensin I to an octapeptide, angiotensin II by removal of the carboxy-terminal. Angiotension I is formed by the action of the enzyme renin, an endopeptidase found in kidney, other tissues and plasma, on a serum alpha-2-globulin.

Blood pressure is affected by certain peptides found in the blood. One of these, angiotensin II, is a powerful pressor (blood pressure elevating) agent. Another bradykinin, a nonapeptide with the sequence ArgProProGlyPheSerProPheArg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors [Gavras, I., et al, *New Engl. J. Med.* 291, 817 (1974)].

ACE is a peptidyldipeptide hydrolase. It catalyzes the hydrolysis of the penultimate peptide bond at the C-terminal end of a variety of acylated tripeptides and larger polypeptides having an unblocked alpha-carboxyl group. The action of ACE results in hydrolytic cleavage of the penultimate peptide bond from the carboxyl-terminal end yielding as reaction products a dipeptide and a remnant.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., *Biochemistry*, 2nd Ed., Worth Publishers, Inc., New York, 1975, pp. 189–195. Many peptides which are called inhibitors of the enzymatic conversion of angiotensin I to angiotensin II are in fact substrates having a lower Km than angiotensin I. Such peptides are more properly termed competitive substrates. Examples of competitive substrates include bradykinin, and the peptide $BPP_{5a}$ (also called SQ20475) from snake venom, having the sequence <GluLysTrpAlaPro.

Numerous synthetic peptide derivatives have been shown to be ACE inhibitors by Ondetti et al in U.S. Pat. No. 3,832,337 issued Aug. 27, 1974.

The role of ACE in the pathogenesis of hypertension has prompted a search for inhibitors of the enzyme that could act as antihypertensive drugs. See, for example, U.S. Pat. Nos. 3,891,616, 3,947,575, 4,052,511 and 4,053,651. A highly effective inhibitor, with high biological activity when orally administered, is D-3-mercapto-2-methylpropanoyl-L-proline, designated SQ 14225, captopril, or capoten, disclosed in U.S. Pat. No. 4,046,889 to Ondetti et al, issued Sept. 6, 1977, and in scientific articles by Cushman, D. W. et al, *Biochemistry* 16, 5484 (1977), and by Ondetti, M. et al, *Science* 196, 441 (1977). The inhibitor SQ 14225 reportedly has an $I_{50}$ value of $2.3 \times 10^{-8}$M. The $I_{50}$ value reported by Cushman, et al, supra, is the concentration of inhibitor required to produce 50% inhibition of the enzyme under a standard assay system containing substrate at a level substantially above $K_m$. It will be understood that $I_{50}$ values are directly comparable when all potential factors affecting the reaction are kept constant. These factors include the source of enzyme, its purity, the substrate used and its concentration, and the composition of the assay buffer. All $I_{50}$ data reported herein have been performed with the same assay system and same enzyme (human urinary ACE) and with an approximately $\frac{1}{2}K_m$ level of substrate and are therefore internally consistent. Discrepancies with data obtained by other workers may be observed. Indeed, such discrepancies do exist in the literature, for unknown reasons. See, for example, the $I_{50}$ values for $BPP_{9a}$ reported by Cushman, D. W. et al, *Experientia* 29, 1032 (1973) and by Dorer, F. E. et al, *Biochim. Biophys. Acta* 429, 220 (1976).

The mode of action of SQ 14225 has been based upon a model of the active site of ACE developed by analogy with the better known related enzyme, carboxypeptidase A. The active site was postulated to have a cationic site for binding the carboxyl end group of the substrate and a pocket or cleft capable of binding the side chain of the C-terminal amino acid and providing especially tight binding for the heterocyclic ring of a terminal proline residue. A similar pocket for the penultimate amino acid residue was postulated, and the published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as a methyl group, and an S-acetyl derivative, substantially reduced potency of the inhibitor. See Cushman, D. W., et al, *Biochemistry*, supra.

In vitro study of the mechanism by which SQ 14225 and its analogs act to inhibit ACE has been somewhat hampered by the instability of these molecules under ambient conditions. For example, it has been observed that a fresh aqueous solution of concentration, e.g., 1 mg per ml of SQ 14225 at a pH of about 8 becomes substantially less active upon standing for as little as 30 minutes, and that activity continues to decrease as the solution stands for longer periods. It is believed that this loss in activity is mainly the result of dimerization of SQ 14225 occurring at the sulfhydryl end groups, whereby a disulfide is formed which is largely inactive as an inhibitor. Since the free sulfhydryl group is highly reactive and may be readily oxidized to polar acidic moieties such as sulfone and sulfoxide groups, it may also be that the observed in vitro loss of activity of aqueous solutions of SQ 14225 on standing is in some part a consequence of one or more such oxidation reactions, with formation of a sulfone or sulfoxide which does not function effectively as an inhibitor for ACE.

Reports of SQ 14225 clinical testing, some of which refer to the compound under the name "Captopril", suggest that the product is sufficiently stable in the normal gastric and intestinal environments of most patients to be an effective inhibitor for ACE when administered orally. It is not yet clear, however, whether there may be a group of patients for which SQ 14225 is substantially ineffective. Because of the high reactivity of the free sulfhydryl group, SQ 14225 could readily form mixed disulfides with serum, cellular proteins, peptides or other free sulfhydryl group-containing substances in the gastric or intestinal environments, in addition to the possibility for dimer formation or oxidative degradation reactions. A mixed disulfide with protein may be antigenic and, indeed, occasional allergic reactions have been clinically observed. See Gavras et al, *New England J. Med.* 298, 991 (1978). Disulfides and oxidative degradation products of SQ 14225, if formed, may at best be expected to be largely ineffective as inhibitors. It may be postulated accordingly that dose reponse to SQ 14225 may vary with conditions of administration and among individual patients. Moreover, in at least some patients, unwanted side effects may occur and maintenance of an effective concentration of the inhibitor in the body may be difficult to control.

Thioester compounds generally are thought to be highly reactive in that the thioester linkage is readily hydrolyzable to a sulfhydryl moiety and a carboxylic moiety. Thioesters are accordingly often used as active ester intermediates for acylation under mild conditions. Such groups as, e.g., acetylthio have been used as blocking groups in the above cited Ondetti et al patents. Thioester intermediates are also postulated to occur in the biosynthesis of cyclic peptides such as tyrocidin or gramicidin S. See Lipmann, F. in *Accounts Chem. Res.* 6, 361 (1973).

Compounds related to SQ 14225 have been disclosed by Ondetti et al, U.S. Pat. Nos. 4,046,889, 4,052,511, 4,053,651, 4,113,715 and 4,154,840. Of interest are disclosed analogs of SQ 14225 having the five-membered heterocyclic ring of proline replaced by a four- or a six-membered ring. The inhibitory potencies of such analogs relative to SQ 14225 are not disclosed. Substitution of D-proline for L-proline is reported to drastically reduce inhibitory potency of 3-mercaptopropanoyl amino acids (Cushman, D. W. et al, supra).

SUMMARY OF THE INVENTION

Novel compounds are disclosed which are orally effective inhibitors of ACE useful in treating mammals suffering from hypertension. They have the general formula:

$$R_1-A_1-S-Z \qquad (I)$$

wherein,

R is hydrogen or an acyl group such as formyl, acetyl, propanoyl, butanoyl, phenylacetyl, phenylpropanoyl, benzoyl, cyclopentane-carbonyl, tert-butyloxycarbonyl, cyclopentanecarbonyl-L-lysyl, L-arginyl, L-lysyl or pyro-L-glutamyl.

$A_1$ is (i) a residue of a compound having at least one carboxyl group and at least one alpha- or beta-amino or alpha-imino group, such as phenylalanine, alanine, tryptophan, tyrosin, isoleucine, leucine, histidine, valine, glycine, phenylglycine, beta-benzylaspartic acid, gamma-benzyl glutamic acid, S-benzyl-cysteine, O-benzyl-serine, O-benzyl tyrosine, O-benzyl threonine, betaphenyl serine, thyronine, beta-2-thienylserine, beta-2-thienylalanine, alpha-methyl-histidine, alpha-methyl tyrosine, alpha-methyl phenylalanine, alpha-methyl tryptophan, tyrosine having a halo, nitro, methoxy or hydroxy substitutent, phenylalanine having a halo, nitro, amino or methoxy substituent, tryptophan having a fluoro, methyl or methoxy substituent, methionine, cysteine, arginine, omega-nitro-arginine, lysine, ornithine, aspartic acid, asparagine, glutamic acid, glutamine, homocysteine, penicillamine, norleucine, serine, beta-alanine, ethionine, homoserine, isoserine, norvaline, threonine, alpha-aminobutyric acid, alpha-aminoisobutyric acid, beta-cyclohexanyl-alanine, O-phosphothreonine, S-ethylcysteine, vinyl glycine, the alpha-methyl derivative of any of valine, leucine, isoleucine, cysteine, methionine, threonine, aspartic acid, glutamic acid, asparagine, glutamine, lysine and arginine; proline alpha-methyl proline, 3,4-dehydroproline, thiazolidine-4-carboxylic acid, cycloleucine, pyroglutamic acid, 1-amino-1-cyclopropane-carboxylic acid, 1-amino-1-cyclobutane carboxylic acid, 1-amino-1 cyclohexane carboxylic acid, or proline having a halo or hydroxy substituent; (ii) is in amide or imide linkage with $R_1$ when $R_1$ is acyl, and (iii) is in thioester linkage through a carboxyl group with -S-.

S is a sulfur atom; and Z represents the grouping

-B-$A_2$ wherein
B is selected from, e.g.

| | | |
|---|---|---|
| (1)  | wherein m is 0 or 1 and $R_2$ is H or lower alkyl; | |
| (2) 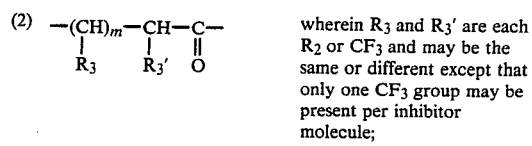 | wherein $R_3$ and $R_3'$ are each $R_2$ or $CF_3$ and may be the same or different except that only one $CF_3$ group may be present per inhibitor molecule; | |
| (3) 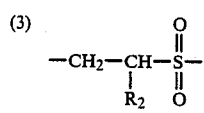 | | |
| (4) 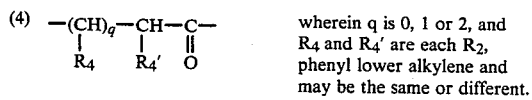 | wherein q is 0, 1 or 2, and $R_4$ and $R_4'$ are each $R_2$, phenyl lower alkylene and may be the same or different. | |
| (5) 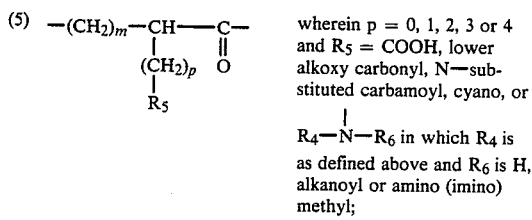 | wherein p = 0, 1, 2, 3 or 4 and $R_5$ = COOH, lower alkoxy carbonyl, N-substituted carbamoyl, cyano, or $R_4$—N—$R_6$ in which $R_4$ is as defined above and $R_6$ is H, alkanoyl or amino (imino) methyl; | |
| (6) 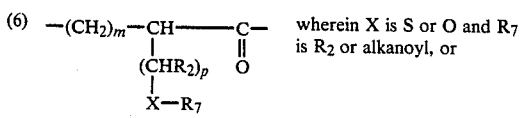 | wherein X is S or O and $R_7$ is $R_2$ or alkanoyl, or | |
| (7) 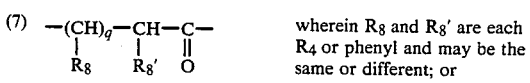 | wherein $R_8$ and $R_8'$ are each $R_4$ or phenyl and may be the same or different; or | |
| (8) 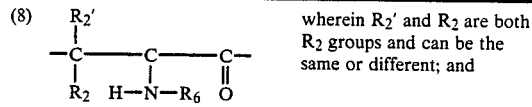 | wherein $R_2'$ and $R_2$ are both $R_2$ groups and can be the same or different; and | |

$A_2$ is selected from, e.g.

| | | |
|---|---|---|
| (9) 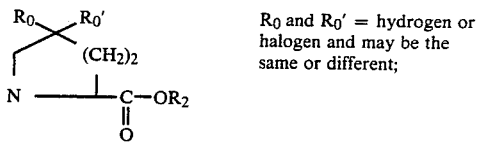 | $R_0$ and $R_0'$ = hydrogen or halogen and may be the same or different; | |
| (10) 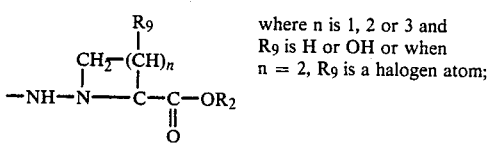 | where n is 1, 2 or 3 and $R_9$ is H or OH or when n = 2, $R_9$ is a halogen atom; | |
| (11) 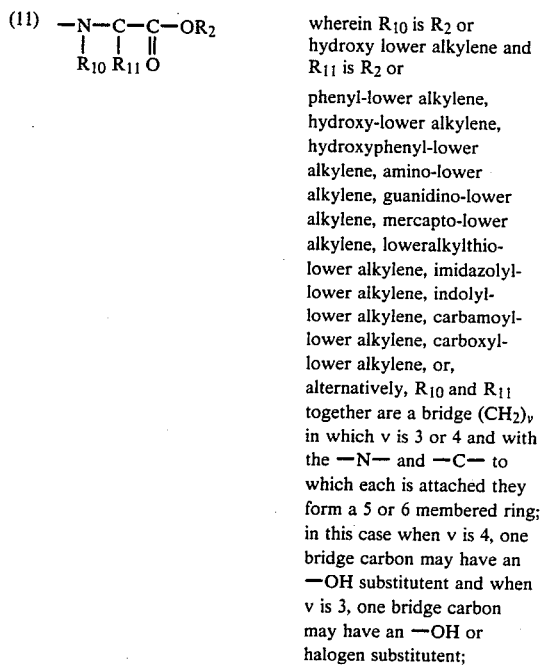 | wherein $R_{10}$ is $R_2$ or hydroxy lower alkylene and $R_{11}$ is $R_2$ or phenyl-lower alkylene, hydroxy-lower alkylene, hydroxyphenyl-lower alkylene, amino-lower alkylene, guanidino-lower alkylene, mercapto-lower alkylene, loweralkylthio-lower alkylene, imidazolyl-lower alkylene, indolyl-lower alkylene, carbamoyl-lower alkylene, carboxyl-lower alkylene, or, alternatively, $R_{10}$ and $R_{11}$ together are a bridge $(CH_2)_v$ in which v is 3 or 4 and with the —N— and —C— to which each is attached they form a 5 or 6 membered ring; in this case when v is 4, one bridge carbon may have an —OH substitutent and when v is 3, one bridge carbon may have an —OH or halogen substitutent; | |
| (12) 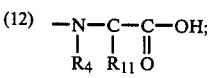 | | |
| (13) 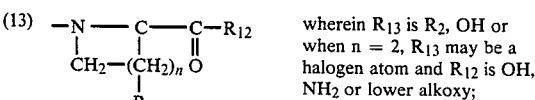 | wherein $R_{13}$ is $R_2$, OH or when n = 2, $R_{13}$ may be a halogen atom and $R_{12}$ is OH, $NH_2$ or lower alkoxy; | |
| (14) 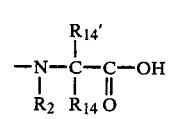 | wherein $R_{14}$ and $R_{14}'$ are each lower alkyl and need not be the same; alternatively, $R_{14}$ and $R_{14}'$ may be a $(CH_2)_4$ bridge which completes a 5-membered ring with carbon to which they are attached; or one of $R_{14}$ and $R_{14}'$ may be a $(CH_2)_3$ bridge which completes a 5-membered ring with the —N— and —C— atoms to which they are respectively attached; | |

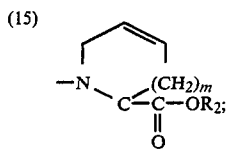
(15)

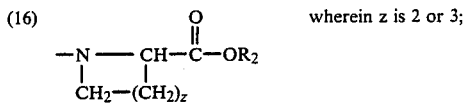
(16) wherein z is 2 or 3;

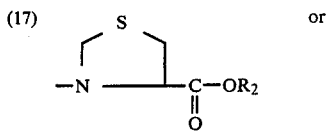
(17) or

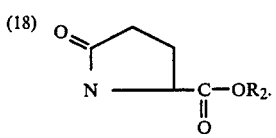
(18)

The physiologically acceptable salts of the above-described compounds are also within the scope of this invention.

Typically, Z is selected from:

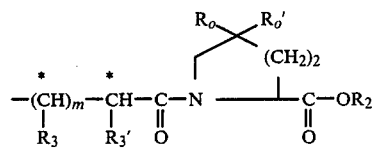
(II)

i.e., B(2) plus A$_2$(9); in this case either one of R$_3$ and R$_3'$ is CF$_3$ or else at least one of R$_o$ and R$_o'$ is halogen, or both;

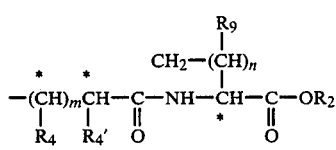
(III)

i.e., B(4) containing no more than 3 carbons in its backbone chain plus A$_2$(10)

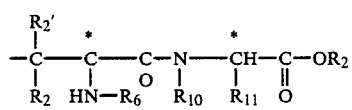
(IV-A)

i.e., B(8) plus A$_2$ (11);

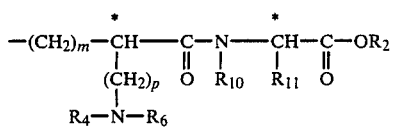
(IV-B)

i.e., B(5) wherein R$_5$ is

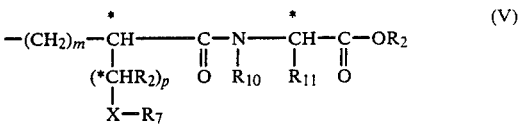

plus A$_2$ (11);

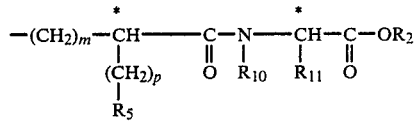
(V)

i.e. B(6) plus A$_2$ (11);

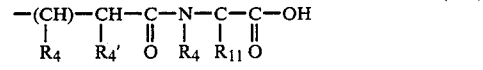
(VI)

with the proviso that R$_5$ is not R$_4$-N-R$_6$-, i.e., B(5) as so limited plus A$_2$(11);

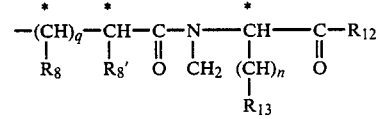
(VII)

i.e. B(4) plus A$_2$ (12);

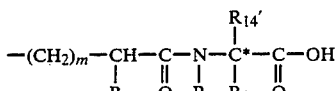
(VIII)

i.e. B(7) plus A$_2$ (13);

(IX)

−(CH$_2$)$_m$−CH−C−N−C*−C−OH
    | || | | ||
    R$_2$ O R$_2$ R$_{14}$ O
with R$_{14}'$ on the C* i.e. B(1) plus A$_2$ (14);

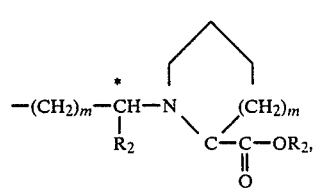
(X-A)

i.e. B(1) plus A$_2$ (17);

(X-B)

−(CH$_2$)$_m$−CH−N(CH$_2$)$_m$
    |    |
    R$_2$   C−C−OR$_2$
         ||
         O i.e. B(1) plus A$_2$ (15);

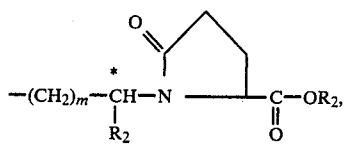

i.e., B(1) plus A₂ (18);

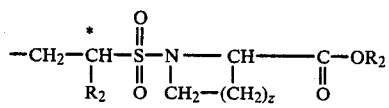

i.e., B(3) plus A₂ (16). Where, e.g., more than one "R₂" appears in the same molecule, the actual R₂ moieties may be the same or different unless otherwise stated and this applies in all cases to all "R" isonumeric groups within a given molecule. The asterisks in the Z formula I–XI indicate asymmetric carbon atoms.

The $A_1$ moiety of the compounds of this invention may be in any optically active form, i.e., D-, L- or racemized (D,L-). The $A_2$ moiety should be in the L-form.

Broadly speaking, -B- represents a backbone chain of 2–4 C atoms in mercapto linkage with -S-, which backbone includes at one end a carbonyl or sulfonyl group by which -B- is linked in amido relationship to a nitrogen atom of $A_2$. Also broadly, $A_2$ is a carboxylic acid, or amide or ester thereof which also contains at least one amino or imino nitrogen, preferably as a part of a 4–6 membered ring with carbon atoms or a 5 membered ring with C atoms and one S atom.

DETAILED DESCRIPTION OF THE INVENTION

The present invention encompasses thioester compounds which contain at least one amino acid or derivative or analog thereof as the $A_1$ moiety and another such acid or derivative or analog thereof as the B moiety. It is preferred that the R group of thioester compounds by an acyl group, most preferably benzoyl.

The $A_1$ portion of the thioester compounds may be a residue of any of the compounds listed. Suitable unsubstituted amino acids to which that residue may correspond include, among others: alanine, phenylalanine, glycine, leucine, isoleucine, valine, tryptophan, tyrosine, histidine, methionine, proline, threonine, ornithine and glutamic acid. Suitable substituted amino acids to which the residue $A_1$ may correspond include among others: cyclohexanyl-alanine, 3-hydroxyproline, 4-nitrophenylalanine, 5-fluorotryptophan, O-benzylthreonine, and vinylglycine. Suitable amino acid analogs to which the residue may correspond include, among others: alpha-aminobutyric acid, cycloleucine, thiazolidine-4-carboxylic acid, and penicillamine. The preferred acyl derivative R, described above, is in amide linkage with the alpha-amino group, alpha-imino or beta-amino group of $A_1$.

When $A_1$ is a halogen-substituted residue of tyrosine or phenylalanine, the halogen may be selected from the group consisting of F, Cl, Br or I. When the phenylalanine residue is mono-substituted by halo, nitro, amino or methoxy, the substituent is preferably at position 4 of the phenyl ring. It is preferred that a tyrosine residue be substituted at position 3 of the phenyl ring when the single substituent is halo, nitro, hydroxy or methoxy. The tyrosine residue may also be di-substituted with halogen atoms, preferably at positions 3 and 5 of the phenyl ring. When a tryptophan residue as $A_1$ is substituted with fluorine, it is preferably at either position 5 or 6 of the indole ring. When the substituent is methyl, however, it may be at any of position 4, 5, 6 or 7 of the indole ring. It is preferable that a methoxy mono-substituent on the tryptophan residue be at position 5 of the indole ring.

When $A_1$ is a proline residue substituted with a halogen, the halogen may be selected from the group consisting of F, Cl, Br or I. The proline residue is preferably mono-substituted at the 3 or 4 position of the pyrrolidine ring when the single substituent is halo or hydroxy. A proline residue as $A_1$ may also be di-substituted with halogen, preferably at positions 3 and 4 of the pyrrolidine ring.

In the thioester compounds of this invention the moiety Z in formula I is made from a moiety B and a moiety $A_2$ and is already described. Z is typically selected from the group of compounds having formulas II–XI. It is preferred that $A_2$ be proline, hydroxy-proline, 3,4-dehydroproline, 5-oxo-proline or a closely related structure such as thiazolidine-4-carboxylic acid.

The lower alkyl groups included in the numbered "R" substituents include straight and branched chain hydrocarbon radicals containing one to seven carbon atoms. The lower alkylene groups are of the same kind also having one to seven carbon atoms. Similarly, the lower alkoxy groups also may have one to seven carbon atoms with a link to oxygen. The lower alkanoyl groups are the acyl radicals of the lower fatty acids having one to seven carbon atoms. The amino(imino)-methyl group represented by $R_6$ is the residue of the guanidino radical

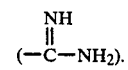

The N-substituted carbamoyl of $R_5$ has a lower alkyl or phenyl-lower alkylene radical attached to N. The halogen substituents in all instances may be selected from the group consisting of F, Cl, Br or I.

The compounds of formula I can be produced by various methods of synthesis. According to preferred method, $R_1$-$A_1$ and HS-Z are coupled to produce $R_1$-$A_1$-S-Z. For this coupling, any conventional coupling agent may be used, preferably in an anhydrous medium. In another preferred method, $R_1$-$A_1$-SH is coupled with halo-Z to produce $R_1$-$A_1$-S-Z using conventional coupling methods. In a third preferred method, $R_1$-$A_1$-SH is coupled with a vinyl-Z to produce $R_1$-$A_1$-S-Z by heating. For a particular desired thioester compound, one method may be more preferred than the others. Examples of suitable coupling agents are 1,1'-carbonyl-diimidazole, dicylohexylcarbodiimide, ethoxyacetylene or diphenylphosphoryl azide. Examples of suitable anhydrous media are tetrahydrofuran (THF), dichloromethane, dioxane or dimethylformamide (DMF), although any other suitable anhydrous medium may be used.

The group $R_1$-$A_1$ where $R_1$ is benzoyl may be obtained commercially or may be synthesized, using the procedures described in Examples 1 and 2 hereof. The group $R_1$-$A_1$ where $R_1$ is formyl, acetyl, propanoyl, butanoyl, phenylacetyl, phenylpropanoyl, or tert-butyloxycarbonyl (Boc) may be obtained commercially or may be synthesized, using the procedure described in Examples 1-3 hereof.

Reactants which are commercially available refer to those reactants which can be obtained from standard chemical and biochemical supply companies. Examples of such companies include Aldrich Chemical Company, Inc., Metuchen, N.J. and Sigma Chemical Co., St. Louis, Mo.

The group $R_1$-$A_1$ where $R_1$ is cyclopentanecarbonyl is synthesized using the procedure described in Examples 4 and 5 hereof. The group $R_1$-$A_1$ where R is cyclopentanecarbonyl-L-lysyl or pyro-L-glutamyl-L-lysyl is synthesized, using the procedure described in Examples 6-8 hereof. The group $R_1$-$A_1$ where $R_1$ is L-arginyl, L-lysyl or pyro-L-glutamyl is synthesized using the procedure described in Examples 9-11 hereof.

The HS-Z group can be produced by various methods of synthesis. For this description, the synthesis of HS-Z where Z is formula VIII will be utilized for illustration purposes only. The process of forming HS-Z where Z corresponds to any of the formulas II-XI is performed in a similar manner.

According to the preferred method, an amino compound corresponding to the $A_2$ group of formula VIII, i.e.,

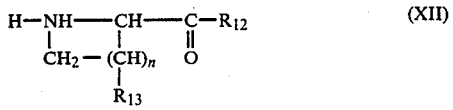

wherein $R_{13}$, $R_{12}$ and n are defined above, is acylated with an acid of the formula,

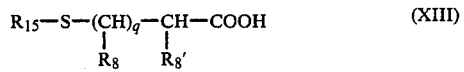

wherein $R_8$, $R_8'$ and q are defined above and $R_{15}$ is hydrogen, lower alkyl, phenyl, substituted phenyl wherein the phenyl substituent is halogen, lower alkyl or lower alkoxy, phenyl-lower alkylene, diphenyl-lower alkylene, triphenyl-lower alkylene, lower alkylthiomethyl, phenyl-lower alkylthiomethyl, lower alkanoyl-amidomethyl, formyl, hydroxycarbonyl lower alkyl carbonyl. Preferably $R_{15}$ is an acetyl group. The acylation of the amino compound XII with the acid XIII can be effected in the presence of a coupling agent in anhydrous medium. Any coupling agent and any anhydrous medium may be utilized as previously described.

Alternatively, the acid of formula XIII can first be activated prior to reaction with the amino group of formula XII to form a mixed anhydride, symmetrical anhydride, acid chloride, active ester, Woodward reagent K or the like. For a review of the methods for acylation see *Methoden der Organischen Chemie* (Houben-Weyl), Vol. XV, part II, page 1 et seq. (1974.) Deprotection, i.e., removal of $R_{15}$ when $R_{15}$ is not H, of the product of the acylation of formula XII with XIII can be effected by conventional means such as treatment with hot trifluoroacetic acid, cold trifluoromethanesulfonic acid, mercuric acetate, sodium in liquid ammonia or the like. For a review of these methods see *Methoden der Organischen Chemie* (Houben-Weyl), Vol. XV, part I, page 376 et seq. (1974). When $R_{15}$ is the preferred acetyl group or is formyl, hydroxycarbonyl or another lower alkyl carbonyl group, the product is preferably deprotected by ammonolysis.

Another method of forming HS-Z as illustrated with Z of formula VIII is to react the amino group of formula XII with an omega-haloalkanoic acid of the formula,

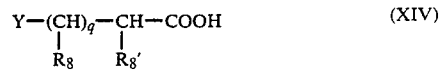

wherein Y is bromo, chloro or iodo to form,

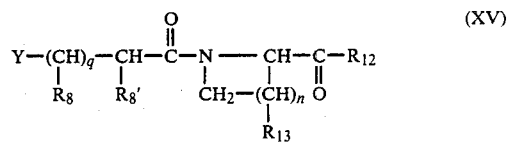

This product is then subjected to displacement or addition with the anion of a thiol or a thioacid of the formula $R_{15}$-SH. The acid of formula XIV is first activated as previously described. The reaction of XIV and XII is conducted in an alkaline medium, for example alkali metal hydroxide, alkali metal bicarbonate, or alkali metal carbonate. The reaction of XV with $R_{15}$-SH is also conducted in an alkaline medium, preferably alkali metal carbonate. Deprotection is accomplished as described above.

Another method of forming HS-Z, again as illustrated with Z of formula VIII is to react the amino group of formula XII with a thiolactone of the formula, e.g.

to yield the desired products HS-Z. This reaction is conducted in an anhydrous medium such as THF or the like.

A variation of this procedure involves the use of an acrylic acid of the formula

as starting material. This acrylic acid is first converted to the acid halide and reacted with the amino group XII to obtain the following product,

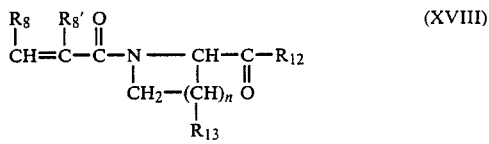

This product is then subjected to the addition of a thiol or a thioacid of the formula $R_{15}$-SH as described above. The reaction of the acrylic acid with the amino group of formula XII is conducted in an alkaline medium, preferably an alkali metal carbonate.

Alternatively, the acrylic acid of formula XVII can be reacted with a thioacid of the formula $R_{15}$-SH to form,

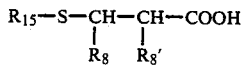 (XIX)

which is converted to the acid halide and reacted with the amino group of formula XII.

When a compound of formula XII, having a free acid group, i.e., when $R_{12}$ is hydroxy, is used as starting material, the final product obtained in the form of a free carboxylic acid can then be converted to its ester, for example by esterification with a diazoalkane, such as diazomethane, or a 1-alkyl-3-p-tolyltriazene, such as 1-n-butyl-3-p-tolyltriazene or the like. Treatment of the ester, preferably the methyl ester, with an alcoholic ammonia solution, converts the free acid to the amide, i.e., $R_{12}$ is then $NH_2$. When a compound of formula XII having an ester group (e.g., $R_{12}$ is an alkoxy group) is used as starting material, the final product obtained can be treated with trifluoroacetic acid and anisole to remove the ester group ($R_{12}$) to yield the free carboxylic acid.

The thioester compounds of the formula $R_1$-$A_1$-S-Z, where $R_1$ is hydrogen, are prepared preferably by deprotecting the N-alkoxycarbonyl derivatives, such as N-alpha-tertbutyloxycarbonyl-$A_1$-S-Z. One method of deprotecting these compounds is described in Example 140 hereof.

Where Z is as defined by formula XI, the HS-Z compounds are preferably synthesized by reacting the amino group with a haloalkylsulfonyl halide in an organic base such as N,N-dimethylaniline, N-methylmorpholine or the like in an inert organic solvent such as THF, dioxane, dichloromethane or the like. The product from this reaction is reacted with $R_{15}$-SH in the presence of an organic base and organic solvent as described above to yield the compound HS-Z corresponding to formula XI.

When Z is defined as in formula III, it is derived from nitrosoazetidine-2-carboxylic acid, nitrosoprolines or nitrosopipecolic acids which have the formula,

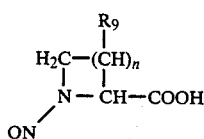 (XX)

Such compounds are prepared from the corresponding azetidine-2-carboxylic acid, -proline or -pipecolic acid, respectively, by means of nitrosyl tetrafluoroborate according to the method of Lijinsky et al, *Tetrahedron* 26, 5137 (1970). They can also be produced by the method described by Nagasawa et al, *J. Med. Chem.* 16, 583 (1973).

The nitroso amino acid of formula XX is next reduced to the N-amino derivative which has the formula,

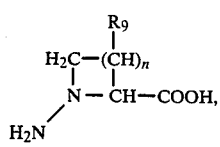 (XXI)

e.g., with zinc-acetic acid by the method described by Klosterman et al, *Biochemistry* 6, 173 (1967).

The $R_1$-$A_1$-S group can be synthesized by various methods. For this description, the synthesis of $R_1$-$A_1$-S, where $R_1$ is benzoyl and $A_1$ is phenylalanyl will be utilized for illustration purposes only.

According to the preferred method thiophenoyl is coupled to N-alpha-tert-butyloxycarbonylphenylalanine using conventional coupling agents to give

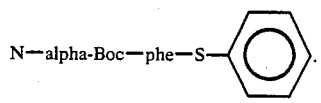

It is preferred that this be done by the mixed anhydride method in ethyl acetate. This compound is deprotected by reacting the compound in TFA and anisole followed by hydrogen chloride in ethanol to produce the hydrogen chloride salt of

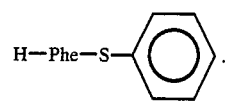

This latter compound is preferably reacted with benzoyl chloride in sodium carbonate and ethyl acetate to produce

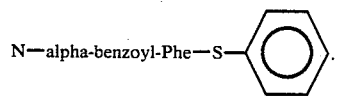

The thiophenol group is removed by reacting with NaSH in ethanol under nitrogen to produce H-alpha-benzoyl-Phe-SH.

Another method of producing N-alpha-benzoyl-Phe-SH is to react N-alpha-benzoyl-Phe with $H_2S$ in a mixed anhydride reaction to produce the desired product. A third method includes the reaction of N-alpha-Boc-Phe with $H_2S$ in a mixed anhydride reaction as described above. This is then followed by a reaction with hydrogen chloride in ethanol and by a reaction with benzoyl chloride as described above.

The N-alpha-benzoyl-Phe-SH is then reacted with a compound such as, e.g., Formula XVIII, for example by heating, preferably in toluene, to produce N-alpha-benzoyl-Phe-S-Z. In addition, the N-alpha-benzoyl-Phe-SH can be reacted with the compound of Formula XV to produce N-alpha-benzoyl-Phe-S-Z. For a more detailed description of the above described methods, see Ryan and Chung applications Ser. No. 128,953, filed Mar. 10, 1980, now abandoned, and Ser. No. 158,278, filed June 10, 1980, now abandoned.

The thioester compounds of formula I have one or more asymmetric carbons. The following compound using $R_1$=benzoyl, $A_1$=Phe and Z of formula VIII is used for illustration purposes only. In the compound

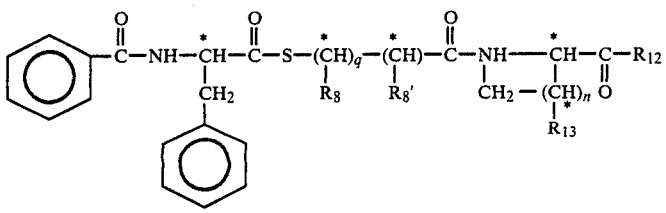

the possible asymmetric carbons are indicated by an asterisk. Thus, when $R_8$, $R_8'$ or $R_{13}$ is other than hydrogen, the carbon to which it is attached is asymmetric. The other carbons marked by an asterisk above are always asymmetric. The compounds accordingly exist in stereoisomeric forms or in racemic mixtures thereof. All of these are within the scope of the invention. The above described syntheses can utilize the racemate or one of the enantiomers as starting material. When the racemic starting material is used in the synthetic procedure or a racemic mixture results from the synthesis, the stereoisomers obtained in the product can be separated by conventional chromatographic or fractional crystallization methods. In general, the L-isomer of the group $A_2$ is the preferred isomeric form. The D-isomer is preferred in the group B for a group attached to the carbon alpha to the carbonyl group (e.g. the carbon bearing $R_8'$ in the above example) is preferred.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product, as illustrated in the examples in the case of the dicyclohexylamine salt.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the

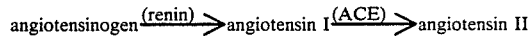

sequence by inhibiting angiotensin converting enzyme and reducing or eliminating the formation of the pressor substance angiotensin II. Thus by the administration of a composition containing one or a combination of compounds of formula I, including the physiologically acceptable salts thereof, angiotensin dependent hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day is appropriate to reduce blood pressure as indicated in the animal model experiments described by S. L. Engel, T. R. Schaeffer, M. H. Waugh and B. Rubin, *Proc. Soc. Exp. Biol. Med.* 143, 483 (1973). The substance is preferably administered orally, but parenteral routes such as subcutaneous, intramuscular, intravenous or intraperitoneal can also be employed.

The compounds of this invention can be utilized to achieve the reduction of blood pressure by formulating them in compositions such as tablets, capsules or elixirs for oral administration or in sterile solutions or suspensions for parenteral administration. About 10 to 500 mg of a compound or mixture of compounds of formula I, including their physiologically acceptable salts, is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

A sterile composition for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, and the like can be incorporated as required.

The present invention is further described by reference to the ensuing examples. In the examples, all temperatures are in degrees Celsius unless otherwise stated and molar equivalents of reactants are usually utilized. The symbol "g" denotes gram(s).

Unless otherwise stated, in these examples the thin-layer chromatography (TLC) was performed using silica gel plates. The numerical solvent systems for use in the TLC procedures are as follows:

(1) is methanol:chloroform, 1:1 (parts by volume). (2) is benzene:water:acetic acid, 9:1:9 (parts by volume). (3) is acetic acid:water:n-butanol, 26:24:150 (parts by volume). (4) is n-butanol:pyridine:acetic acid:water, 15:10:3:12 (parts by volume). (5) is chloroform:methanol:ammonium hydroxide, 60:45:20 (parts by volume. Also, unless otherwise stated, the buffers for paper electrophoresis were pH 1.9—formic acid:acetic acid:water, 3:2:25 (parts by volume); pH 5.0—diethylene glycol:acetic acid:pyridine:water, 100:6:8.5:885 (parts by volume).

Examples 1–28 hereof deal with the synthesis of the compound $R_1$-$A_1$, one precursor of $R_1$-$A_1$-S-Z.

EXAMPLE 1

Preparation of N-Alpha-Benzoylphenylalanine

A mixture containing 8.21 g of phenylalanine, 5.565 g of $Na_2CO_3$ in 40 ml of water and 20 ml of tetrahydrofuran (THF) was stirred at room temperature. Benzoyl chloride, 7.73 g, dissolved in 20 ml of anhydrous THF, was added gradually over a period of 45 minutes with continued stirring at room temperature. Stirring was allowed to continue for an additional hour, at which time the reaction mixture was transferred to a rotary evaporator at 30° C. to remove the THF. An excess of water was then added and the reaction mixture extracted four times with ethyl acetate. The aqueous phase was then titrated to pH 2 with 3N HCl. A white crystalline precipitate formed which was recovered by filtration, washed three times with cold dilute HCl and three times with cold water, and dried in a vacuum oven over $P_2O_5$ at about 50° C. The product was recrystallized from aqueous ethanol, yielding 8.37 g, m.p. 183° C.—184° C., which migrated as a single compound on thin layer chromatography in five separate solvent systems. In this reaction sequence the racemate is obtained.

If a NaOH solution is used in place of the $Na_2CO_3$ in this example and the procedure set forth in Carter, H. E. et al, *J. Biol. Chem.* 138, 627 (1941) is substantially followed, optical activity is maintained. Thus, if L-Phe or D-Phe is the starting material, N-alpha-benzoyl-L-phe, or N-alpha-benzoyl-D-Phe, respectively, is produced.

Similarly, when benzoyl N-hydroxysuccinimide ester is used in place of benzoyl chloride in this example and the same procedure is followed, the optical activity of D-Phe or D-Phe is maintained in the N-alpha-benzoyl derivative.

EXAMPLE 2

By substituting glycine, alanine, tryptophan, tyrosine, isoleucine, leucine, histidine or valine for Phe in Example 1 and substantially following the procedures set forth in Example 1, the N-alpha-benzoyl derivatives of these amino acids are obtained.

EXAMPLE 3

Although the formyl, acetyl, propanoyl, butanoyl, phenylacetyl, phenylpropanoyl or tert-butyloxycarbonyl derivatives of the Phe, Gly, Ala, Trp, Tyr, Ile, Leu, His or Val are commercially available, they are also obtained by substituting the analogous acid chloride or acyl N-hydroxy succinimide ester for the benzoyl chloride in either of Examples 1 or 2 and substantially following the procedures of Example 1.

EXAMPLE 4

Synthesis of N-Alpha-Cyclopentanecarbonylphenylalanine

A cool solution of 2.06 g of dicyclohexylcarbodiimide in 10 ml of dichloromethane was added to a solution of 1.4114 g of cyclopentanecarboxylic acid in 5 ml of dichloromethane at −5° C. It was followed by the addition of 4.28 g of phenylalanine benzyl ester toluenesulfonate salt in 10 ml of DMF which was neutralized with 1.36 ml of N-ethyl morpholine. The reaction mixture was stirred at 0° C. for one hour and then at room temperature for three hours. Dicyclohexylurea was removed by filtration and 50 ml of ethyl acetate was added to the filtrate. The organic phase was washed until neutral, dried over anhydrous $MgSO_4$ and filtered. The solvent was removed with a rotary evaporator. The residue was crystallized from isopropanol and hexane yielding 2.35 g of white crystals having a melting point of 88°–89° C. Elemental analysis of these crystals yielded the following:

Calculated: C=75.19; H=7.17; N=3.9855;
Found: C=74.96; H=7.17; N=4.09.

The benzyl ester group was removed by hydrogenolysis with 2 g of 10% palladium on carbon in absolute alcohol. The catalyst was removed by filtration and the ethanol was removed with a rotary evaporator. The residue was crystallized from ether and hexane yielding 1.15 g white crystals of the named product having a melting point of 107°–108° C. Elemental analysis of these crystals yielded the following:

Calculated: C=68.94; H=7.33; N=5.36;
Found: C=68.90; H=7.32; N=5.34.

The product was found to be homogeneous by paper electrophoresis and by TLC in solvent systems 1, 2 and 3. The named product may be abbreviated as N-alpha-Cpc-L-Phe.

EXAMPLE 5

By substituting each of Gly, Ala, Trp, Tyr, Ile, Leu, His, or Val for the Phe of Example 4, and substantially following the procedure of Example 4 each time, the N-alpha-Cpc derivatives of these amino acids are obtained.

EXAMPLE 6

(a) Synthesis of the N-hydroxysuccinimide ester of cyclopentane carboxylic acid

A cool solution of 11.4 g of dicyclohexylcarbodiimide in dimethylformamide (DMF) was added dropwise to a mixture of 5.71 g of cyclopentanecarboxylic acid and 5.76 g of N-hydroxysuccinimide in DMF at 0° C. The reaction mixture was stirred at 0° C. for 30 minutes and then at 4° C. overnight. Crystalline dicyclohexylurea was removed by filtration and the precipitate was washed with ethyl acetate. Solvents from the combined filtrate were removed under reduced pressure and the residue was crystallized from benzene and hexane yielding 5.77 g of white crystals having a melting point of 72.5°–73° C. The infrared absorption spectrum in chloroform gave a typical spectrum of N-hydroxysuccinimide esters. Elemental analysis of the crystals yielded the following results:

Calculated: C=56.86; H=6.20; N=6.63;
Found: C=56.77; H=6.07; N=6.66.

(b) Synthesis of N-Alpha-Cyclopentanecarbonyl-N-Epsilon-Tert-Butyl-Oxycarbonyl-L-Lysine A solution of 1.2316 g of N-epsilon-tert-butyloxycarbonyl-L-lysine and 420 mg of $NaHCO_3$ in 10 ml of water and 5 ml of THF was cooled in an ice bath with stirring. To this solution was added a cold solution of 1.19 g of the product from step (a) in 10 ml of THF. The THF was removed with a rotary evaporator at 35° C. after the reaction mixture had been stirred overnight at room temperature. About 20 ml of water was added to the reaction mixture and the pH was adjusted to 9 with solid $NaHCO_3$. The aqueous phase was extracted three times with ethyl acetate and the organic phase was discarded. The aqueous solution was cooled in an ice bath and then acidified to pH 2 with 1N HCl in the presence of ethyl acetate. The organic phase was washed twice with ice water and then twice with a solution of saturated NaCl. The organic solution was dried over anhydrous $MgSO_4$ and then filtered. The solvent was removed with a rotary evaporator and the residue was crystallized from ether and hexane yielding 1.135 g of white crystals having a melting point of 104.5°–105.5° C. Elemental analysis of the crystals yielded the following:

Calculated: C=59.63; H=8.83; N=8.18;
Found: C=59.74; H=8.85; N=8.24.

The product was shown to be homogeneous by paper electrophoresis and by TLC with solvent systems 1–3.

(c) Synthesis of N-alpha-cyclopentanecarbonyl-N-epsilon-tert-butyloxy-carbonyl-L-lysine-N-hydroxysuccinimide ester A solution of 1.027 g of the product from step (b) and 346 mg of N-hydroxysuccinimide in 10 ml of $CH_2Cl_2$ was cooled to −5° C. To this solution was added with stirring a cold solution of 680 mg of dicyclohexylcarbodiimide in 5 ml of $CH_2Cl_2$. The reaction mixture was stirred at 0° C. for 30 minutes and then at 4° C. overnight. Crystalline dicyclohexylurea was removed by filtration and was washed with ethyl acetate. The combined filtrate was washed twice with a 1.0N $NaHCO_3$, twice with water and finally with a solution of saturated NaCl. The organic phase was dried over anhydrous $MgSO_4$, filtered, and the solvent was removed with a rotary evaporator. The residue was crystallized from isopropanol yielding 0.844 g of white crystals having a melting point of 140.5° C. The infrared absorption spectrum in chloroform gave a spectrum typical of N-hydroxysuccinimide esters. Elemental analysis of the crystals yielded the following:

Calculated: C=57.39; H=7.57; N=9.56;
Found: C=57.10; H=7.57; N=9.61.

(d) Synthesis of N-alpha-cyclopentanecarbonyl-N-epsilon-tert-butyl-oxycarbonyl-L-lysylphenylalanine A solution of 220 mg of the product from step (c) hereof in 2 ml of dioxane was added drop-wise to a mixture of 99.1 mg of phenylalanine and 51 mg of $NaHCO_3$ in a mixture of 2 ml of water and 1 ml of DMF. The reaction mixture was stirred at room temperature overnight and dioxane was removed with a rotary evaporator at 35° C. Ethyl acetate (10 ml) was added to the reaction mixture, cooled, acidified to pH 2 with 0.1N HCl and the aqueous solution was discarded. The organic phase was washed with ice water, a solution of saturated NaCl and dried over anhydrous $MgSO_4$; and the solvent was removed with a rotary evaporator. The residue was crystallized from ether and petroleum ether (b.p. 30°–60° C.) yielding 95 mg of white solid having a melting point of 90°–92° C. The product was shown to be homogeneous by paper electrophoresis at pH 1.9 and 5.0 and by TLC in the separate solvent systems 1, 2, 3 and 4. Elemental analysis yielded the following results:

Calculated: C=63.78; H=8.03; N=8.58;
Found: C=63.40; H=8.07; N=8.34.

The named compound can be abbreviated N-alpha-Cpc-N-epsilon-Boc-L-Lys-L-Phe.

EXAMPLE 7

By substituting Gly, Ala, Trp, Tyr, Ile, Leu, His or Val for the Phe in step (d) of Example 6, and substantially following the procedure of that step, the N-alpha-Cpc-N-epsilon-Boc-L-Lys derivatives of these amino acids are obtained.

EXAMPLE 8

By substituting pyro-L-glutamic acid for the cyclopentane carboxylic acid in Example 6 and substantially following the procedures of steps (a)–(c) thereof, N-alpha-pyro-L-glutamyl-N-epsilon-tert-butyloxycarbonyl-L-lysine-N-hydroxysuccinimide ester es obtained. By substituting this product for the N-alpha-Cpc-N-epsilon-Boc-L-Lys-N-hydroxysuccinimide ester in step (d) of Example 6 or Example 7 and substantially following the procedure of Example 6, step (d), the N-alpha-pyro-L-glutamyl-N-epsilon-Boc-L-Lys derivatives of the amino acids are obtained.

To prepare N-benzoyl-phenylalanyl-N-hydroxy-succinimide ester, 1.347 g of benzoyl-phenylalanine and 0.576 g of N-hydroxy succinimide were mixed in a 1:1 (by volume) mixture of THF and dimethylformamide (DMF). The mixture was incubated at 4° C. overnight in the presence of 1.133 g of dicyclohexylcarbodiimide.

The reaction mixture was filtered and the solvent was removed under reduced pressure at 30° C. A white residue remained which was recrystallized from THF-isopropyl alcohol to yield 1.194 g (65.2%) of a white solid, m.p. 156° C.–157° C. The infrared absorption spectrum in chloroform showed bands at 3440 $cm^{-1}$ indicating an NH group, at 1818 $cm^{-1}$, 1790 $cm^{-1}$, and 1744 $cm^{-1}$, characteristic of the N-carboxy succinimide group and at 1669 $cm^{-1}$, characteristic of the N-benzoyl moiety.

This product can also be subjected to steps (c) and (d) to remove the protecting group.

EXAMPLE 9

(a) Preparation of pyro-L-glutamylphenylalanine benzyl ester

A solution of 0.52 g of pyro-L-glutamic acid, 1.72 g of phenylalanine benzyl ester toluene sulfonic acid and 0.55 mg of N-ethylmorpholine in 5 ml of dimethylformamide (DMF) and 20 ml of dichloromethane was cooled in an ice bath with stirring. A solution of 0.826 g of dicyclohexylcarbodiimide in 2 ml dichloromethane was added to the above reaction mixture. The reaction mixture was stirred in an ice water bath for 1 hour and then at room temperature overnight. Dicyclohexylurea was removed by filtration and the product was washed in ethyl acetate. Solvents of the combined filtrates were removed under reduced pressure with a rotary evaporator at 40° C. Ethyl acetate (25 ml) was added to the residue and the organic solution was washed until neutral. The organic phase was dried over anhydrous MgSO$_4$, filtered and then the solvent was removed with a rotary evaporator. The material was crystallized from isopropanol and ether, yield: 1.01 g of white needles, m.p. 103°–104.5° C. The material was shown to be honogeneous by paper electrophoresis and by TLC with the five separate solvent systems described. Elemental analysis yielded the following results:
Calculated: C=68.84; H=6.05; N=7.64;
Found: C=68.58; H=6.05; N=7.56.

(b) Preparation of pyro-L-glutamylphenylalanine

The benzyl ester protecting group of the compound of step (a) (1.0 g) was removed by catalytic hydrogenolysis with 150 mg of 10% (by weight) Pd on carbon in 0.15 ml of glacial acetic acid and 15 ml of ethanol at 20 psi of H$_2$ at room temperature overnight. The catalyst was removed by filtration. Solvent was removed with a rotary evaporator. The material was crystallized from isopropanol and benzene, to yield a total of 402 mg of white crystals, m.p. 147°–149° C. The material was shown to be homogeneous by paper electrophoresis and TLC with solvent systems 1–3. Elemental analysis yielded the following results:
Calculated: C=60.86; H=5.84; N=10.14;
Found: C=60.37; H=5.85; N=9.98.

EXAMPLE 10

By substituting N-alpha N-epsilon-bis-t-butyloxycarbonyl-L-lysine (hereinafter bis-Boc-L-Lys) or N-alpha N-alpha N-omegatriadamantyloxycarbonyl-L-arginine (hereinafter tri-Adoc-L-arginine) for pyro-L-glutamic acid in Example 9, step (a), and by following substantially the procedure of Example 9, step (a), the corresponding bis-Boc-L-Lys or tri-Adoc-L-Arg derivatives of L-Phe benzyl ester will be synthesized. Bis-Boc-L-Lys is commercially available. Tri-Adoc-L-Arg is prepared according to Jager, G. and Geiger, R., *Chem Ber.* 102, 1727 (1970).

EXAMPLE 11

By substituting the benzyl esters of Gly, Ala, Trp, Tyr, Ile, Leu, His or Val, for Phe in Examples 9 and 10, and substantially following the procedures of Examples 9 and 10, the corresponding pyro-L-glutamyl, bis-Boc-L-Lys and tri-Adoc-L-Arg derivatives of these amino acids are obtained.

EXAMPLE 12

Synthesis of N-alpha-benzoyl-norleucine

A mixture containing 10 mmoles of norleucine, 10 mmoles of Na$_2$CO$_3$ in water and tetrahydrofuran (THF) is stirred at room temperature. Benzoyl chloride (10 mmoles), dissolved in anhydrous THF, is added gradually with continued stirring at room temperature. The reaction mixture is stirred until the reaction is completed as judged by thin layer chromatography (TLC). The solvent is removed by a rotary evaporator at 30° C. An excess of water is added and the reaction mixture extracted several times with ethyl acetate. The aqueous phase is adjusted to pH 2 with 1N HCl. The precipitate is recovered by filtration and washed with diluted HCl and then with cold water. The precipitate is dried over P$_2$O$_5$ in a vacuum desiccator. The precipitate is homogeneous as judged by TLC. In this reaction sequence, the racemate is obtained.

The optical activity can be maintained by reacting molar equivalents of benzoyl chloride and norleucine in a sodium hydroxide solution as described in Carter, H. E., et al, *J. Biol. Chem.* 138,627 (1941). That is, if L-norleucine or D-norleucine is the starting material, N-alpha-benzoyl-L-norleucine or N-alpha-benzoyl-D-norleucine, respectively, is produced.

Similarly, if benzoyl N-hydroxysuccinimide ester or other active ester of benzoic acid is used in place of benzoyl chloride in Example 1, the optical activity is maintained.

EXAMPLE 13

By substituting a particular A$_1$ group or protected A$_1$ group for norleucine in Example 12, and substantially following the procedure described therein, the N-alpha-benzoyl derivatives of the A$_1$ compounds are obtained.

EXAMPLE 14

Synthesis of N-alpha-cyclopentanecarbonyl-norvaline

A cool solution of 15 mmoles of dicyclohexylcarbodiimide in dichloromethane is added to a solution of 15 mmoles of cyclopentanecarboxylic acid in dichloromethane at −5° C. 15 mmoles of norvaline benzyl ester toluenesulfonate salt in dimethylformamide (DMF), which is neutralized with N-ethyl morpholine, is then added. The reaction mixture is stirred at 0° C. initially and then at room temperature until the reaction is completed as judged by TLC. Dicyclohexylurea is removed by filtration and 50 ml of ethyl acetate is added to the filtrate. The organic phase is washed until neutral, dried over anhydrous MgSO$_4$ and filtered. The solvent is removed with the rotary evaporator. The residue is crystallized from isopropanol and hexane.

The benzyl ester is removed by catalytic hydrogenolysis with 10% palladium on carbon in absolute ethanol. The catalyst is removed by filtration and the ethanol is removed by a rotary evaporator. The residue is crystallized from ether and hexane yielding the named compound.

EXAMPLE 15

By substituting a particular A$_1$ group or protected A$_1$ group for norvaline in Example 14 and substantially following the procedures described therein, the N-alpha-cyclopentanecarbonyl (Cpc) derivatives of the A$_1$ compounds are obtained.

EXAMPLE 16

(a) Synthesis of the N-hydroxysuccinimide ester of cyclopentane carboxylic acid A cool solution of 20 mmoles of dicyclohexylcarbodiimide in dimethylformamide (DMF) is added drop-wise to a mixture of 20 mmoles of cyclopentanecarboxylic acid and 20 mmoles of N-hydroxysuccinimide in DMF at 0° C. The reaction mixture is stirred at 0° C. for 30 minutes and then at 4° C. overnight. Crystalline dicyclohexylurea is removed by filtration and the precipitate was washed with ethyl acetate. Solvents from the combined filtrates are removed under reduced pressure and the residue is crystallized from benzene and hexane yielding the named product.

(b) Synthesis of N-alpha-cyclopentanecarbonyl-N-epsilon-tert-butyloxycarbonyl-L-lysine A solution of 10 mmoles of N-epsilon-tert-butyloxycarbonyl-L-lysine and 10 mmoles of $NaHCO_3$ in water and THF is cooled in an ice bath with stirring. To this solution is added a cold solution of 10 mmoles of the product from Example 6 in THF. The THF is removed with a rotary evaporator at 35° C. after the reaction mixture is stirred overnight at room temperature. Water is added to the reaction mixture and the pH is adjusted to 9 with solid $NaHCO_3$. The aqueous phase is extracted three times with ethyl acetate and the organic phase is discarded. The aqueous solution is cooled in an ice bath and then acidified to pH 2 the 1N HCl in the presence of ethyl acetate. The organic phase is washed twice with ice water and then twice with a solution of saturated NaCl. The organic solution is dried over anhydrous $MgSO_4$ and then filtered. The solvent is removed with a rotary evaporator and the residue is crystallized from ether and hexane yielding the named product.

(c) Synthesis of N-alpha-cyclopentanecarbonyl-N-epsilon-tert-butyloxy-carbonyl-L-lysine-N-hydroxysuccinimide ester A solution of 10 mmoles of the product from step (b) and 10 mmoles of N-hydroxysuccinimide in $CH_2Cl_2$ is cooled to −5° C. To this solution is added with stirring a cold solution of 10 mmoles of dicyclohexylcarbodiimide in $CH_2Cl_2$. The reaction mixture is stirred at 0° C. for 30 minutes and then at 4° C. overnight. Crystalline dicyclohexylurea is removed by filtration and is washed with ethyl acetate. The combined filtrate is washed twice with a 1.0N $NaHCO_3$, twice with water and finally with a solution of saturated NaCl. The organic phase is dried over anhydrous $MgSO_4$, filtered, and the solvent is removed with a rotary evaporator. The residue is crystallized from isopropanol yielding the named product.

(d) Synthesis of N-alpha-(N-alpha-cyclopentanecarbonyl-N-epsilon-tert-butyloxycarbonyl-L-lysyl)-methionine A solution of 10 mmoles of the product from step (c) in dioxane is added drop-wise to a mixture of 10 mmoles of methionine and 10 mmoles of $NaHCO_3$ in a mixture of water and DMF. The reaction mixture is stirred at room temperature overnight and the dioxane is removed with a rotary evaporator at 35° C. Ethyl acetate is added to the mixture which is then cooled and acidified to pH2 with 0.1N HCl. The aqueous phase is discarded. The organic phase is washed with cold water, saturated NaCl and dried over anhydrous $MgSO_4$. The solvent is removed with a rotary evaporator and the residue is crystallized from ether-hexane yielding the named product.

EXAMPLE 17

By substituting a particular $A_1$ group or protected $A_1$ group for methionine in Example 16 and substantially following the procedure described therein, the N-alpha-Cpc-N-epsilon-Boc-L-Lys derivatives of the $A_1$ compounds are obtained. For example, if $A_1$=proline, its N-alpha-Cpc-N-epsilon-Boc-L-Lys derivative is obtained.

EXAMPLE 18

The substituting pyro-L-glutamic acid for the cyclopentane carboxylic acid in Example 16, and substantially following the procedures of Example 16, steps (a)–(c), N-alpha-pyro-L-glutamyl-N-epsilon-tert-butyloxycarbonyl-L-lysine-N-hydroxysuccinimide ester is obtained. By substituting this product for the N-alpha-Cpc-N-epsilon-Boc-L-Lys-N-hydroxysuccinimide ester in Example 16, step (d) and Example 17, and substantially following the procedures of Example 16, step (d), the N-alpha-pyro-L-glutamyl-N-epsilon-Boc-L-Lys derivatives of the $A_1$ compounds are obtained.

EXAMPLE 19

(a) Synthesis of N-alpha-pyro-L-glutamyl-S-acetyl-penicillamine-t-butyl ester A solution of 20 mmoles of pyro-L-glutamic acid and 20 mmoles S-acetyl-penicillamine t-butyl ester toluene sulfonic acid, neutralized with N-ethyl morpholine, in dichloromethane: DMF (4:1) is cooled in an ice bath with stirring. A solution of 20 mmoles of dicyclohexylcarbodiimide in dichloromethane is added to the above reaction mixture. The reaction mixture is stirred in an ice water bath for 1 hour and then at room temperature overnight. Dicyclohexylurea is removed by filtration and the product is washed in ethyl acetate. Solvents of the combined filtrates are removed under reduced pressure with a rotary evaporator at 40° C. Ethyl acetate is added to the residue and the organic solution is washed until neutral. The organic phase is dried over anhydrous $MgSO_4$, filtered and then the solvent is removed with a rotary evaporator. The material is crystallized from isopropanol and ether, yielding the named product.

(b) Synthesis of N-alpha-pyro-L-glutamyl-S-acetyl-penicillamine

The tbutyl ester protecting group of the compound of Example 12 is removed by treatment with anhydrous trifluoroacetic acid in the presence of anisole. The solvents are removed by a rotary evaporator. The residue is crystallized from isopropanol and benzene yielding the named product.

EXAMPLE 20

By substituting N-alpha, N-epsilon-bis-t-butyloxycarbonyl-L-lysine (hereinafter bis-Boc-L-Lys) or N-alpha, N-alpha, N-omega-triadamantyloxycarbonyl-L-arginine (hereinafter tri-Adoc-L-arginine) for pyro-L-glutamic acid in Example 19 and by following substantially the procedure of Example 19, steps (a) and (b), the corresponding L-Lys or L-Arg derivatives of S-acetyl penicillamine will be synthesized. Bis-Boc-L-Lys is commercially available. Tri-Adoc-L-Arg is prepared according to Jager, G. and Geiger, R., *Chem. Ber.* 102, 1727 (1970).

EXAMPLE 21

By substituting the t-butyl esters of a particular $A_1$ group or protected $A_1$ group for the S-acetyl-penicillamine in Examples 19, step (a) and 20, and substantially following the procedures of Examples 19 and 20, the corresponding pyro-L-glutamyl, bis-Boc-L-Lys and tri-Adoc-L-Arg derivatives of the $A_1$ groups are obtained.

EXAMPLE 22

Synthesis of N-alpha-benzoyl-thiazolidine-4-carboxylic acid

A mixture containing 10 mmoles of thiazolidine-4-carboxylic acid, 10 mmoles of $Na_2CO_3$ in water and tetrahydrofuran (THF) is stirred at room temperature. Benzoyl chloride (10 mmoles), dissolved in anhydrous THF, is added gradually with continued stirring at room temperature. The reaction mixture is stirred until the reaction is completed as judged by thin layer chromatography (TLC). The solvent is removed by a rotary evaporator at 30° C. An excess of water is added and the reaction mixture extracted several times with ethyl acetate. The aqueous phase is adjusted to pH 2 with 1N HCl. The precipitate is recovered by filtration and washed with dilute HCl and then with cold water. The precipitate is dried over $P_2O_5$ in a vacuum desiccator. The precipitate is homogeneous as judged by TLC. In this reaction sequence the racemate is obtained.

The optical activity can be maintained by reacting molar equivalents of benzoyl chloride and thiazolidine-4-carboxylic acid in a sodium hydroxide solution as described in Carter, H. E., et al., *J. Biol. Chem.* 138, 626 (1941). That is, if L-thiazolidine-4-carboxylic acid or D-thiazolidine-4-carboxylic is the starting material, N-alpha-benzoyl-L-thiazolidine-4-carboxylic acid or N-alpha-benzoyl-D-thiazolidine-4-carboxylic acid respectively is produced.

Similarly, if benzoyl N-hydroxysuccinimide ester or other active ester of benzoic acid is used in place of benzoyl chloride in this Example 22, the optical activity is maintained.

EXAMPLE 23

By substituting a particular $A_1$ group or protected $A_1$ group for thiazolidine-4-carboxylic acid in Example 22, and substantially following the procedure described therein, the N-alpha-benzoyl derivatives of the $A_1$ compounds are obtained.

EXAMPLE 24

The formyl, acetyl, propanoyl, butanoyl, phenylacetyl, phenylpropanoyl or tert-butyloxycarbonyl (Boc) derivatives of the $A_1$ compounds are obtained by substituting the appropriate acyl chloride, acyl N-hydroxysuccinimide ester or other acyl active ester for the benzoyl chloride in Examples 22 and 23 and substantially following the procedure of Example 23.

EXAMPLE 25

Synthesis of N-alpha-cyclopentanecarbonyl-cycloleucine

A cool solution of 15 mmoles of dicyclohexylcarbodiimide in dichloromethane is added to a solution of 15 mmoles of cyclopentanecarboxylic acid in dichloromethane at $-5°$ C. 15 mmoles of cycloleucine benzyl ester toluenesulfonate salt in dimethylformamide (DMF), which is neutralized with N-ethyl morpholine, is then added. The reaction mixture is stirred at 0° C. initially and then at room temperature until the reaction is completed as judged by TLC. Dicyclohexylurea is removed by filtration and 50 ml of ethyl acetate is added to the filtrate. The organic phase is washed until neutral, dried over anhydrous $MgSO_4$ and filtered. The solvent is removed with a rotary evaporator. The residue is crystallized from isopropanol and hexane.

The benzyl ester is removed by catalytic hydrogenolysis with 10% palladium on carbon in absolute ethanol. The catalyst is removed by filtration and the ethanol is removed by a rotary evaporator. The residue is crystallized from ether and hexane yielding the named compound.

EXAMPLE 26

By substituting a particular $A_1$ group or protected $A_1$ group for cycloleucine in Example 25 and substantially following the procedure described therein, the N-alpha-cyclopentanecarbonyl (Cpc) derivatives of the $A_1$ compounds are obtained.

EXAMPLE 27

(a) Synthesis of N-alpha-pyro-L-glutamyl-3-bromo-proline benzyl ester

A solution of 20 mmoles of pyro-L-glutamic acid and 20 mmoles of 3-bromo-proline benzyl ester toluene sulfonic acid, neutralized with N-ethyl morpholine, in dichloromethane: DMF(4:1) is cooled in an ice bath with stirring. A solution of 20 mmoles of dicyclohexylcarbodiimide in dichloromethane is added to the above reaction mixture. The reaction mixture is stirred in an ice water bath for one hour and then at room temperature overnight. Dicyclohexylurea is removed by filtration and the product is washed in ethyl acetate. Solvents of the combined filtrates are removed under reduced pressure with a rotary evaporator at 40° C. Ethyl acetate is added to the residue and the organic solution is washed until neutral. The organic phase is dried over anhydrous $MgSO_4$, filtered and then the solvent is removed with a rotary evaporator. The material is crystallized from isopropanol and ether yielding the named product.

(b) Synthesis of N-alpha-pyro-L-glutamyl-3-bromo-proline

The benzyl ester protecting group of the compound of step a is removed by catalytic hydrogenolysis with 10% palladium on carbon in absolute ethanol. The catalyst is removed by filtration and the ethanol is removed by a rotary evaporator. The residue is crystallized from isopropanol and benzene yielding the named product.

EXAMPLE 28

Synthesis of N-alpha-benzoyl-O-threonine

A mixture containing 10 mmoles of O-benzyl-threonine, 10 mmoles of $Na_2CO_3$ in water and tetrahydrofuran (THF) is stirred at room temperature. Benzoyl chloride (10 mmoles), dissolved in anhydrous THF, is added gradually with continued stirring at room temperature. The reaction mixture is stirred until the reaction is completed as judged by thin layer chromatography (TLC). The solvent is removed by a rotary evaporator at 30° C. An excess of water is added and the reaction mixture extracted several times with ethyl acetate. The aqueous phase is adjusted to pH 2 with 1N HCL. The precipitate is recovered by filtration and washed with dilute HCl and then with cold water. The precipitate is dried over $P_2O_5$ in a vacuum desiccator. The precipitate is homogeneous as judged by TLC. In this reaction sequence, the racemate is obtained.

The optical activity can be maintained by reacting molar equivalents of benzoyl chloride and O-benzyl-threonine in a sodium hydroxide solution as described in Carter, H. E., et al., *J. Biol. Chem.* 138, 627 (1941). That is, if O-benzyl-L-threonine or O-benzyl-D-threonine is the starting material, N-alpha-benzoyl-O-benzyl-D-threonine or N-alpha-benzoyl-O-benzyl-D-threonine respectively is produced.

Similarly, if benzoyl N-hydroxysuccinimide ester or other active ester of benzoic acid is used in place of benzoyl chloride in this example, the optical activity is maintained.

Examples 29 to 36 hereof describe the synthesis of HS-Z wherein Z is as defined by formula VIII. Similar procedures are described in U.S. Pat. Nos. 4,046,889 and 4,105,776.

EXAMPLE 29

(a) Synthesis of N-(2-Benzoylthioacetyl)-L-Proline

L-Proline (5.75 g) is dissolved in 1.0N sodium hydroxide (50 ml) and the solution is chilled in an ice-water bath. Sodium hydroxide 2N (26 ml) and chloroacetyl chloride (5.65 g) are added and the mixture is stirred vigorously at room temperature for 3 hours. A suspension of thiobenzoic acid (7.5 g) and potassium carbonate (4.8 g) in water (50 ml) is added. After 18 hours stirring at room temperature, the reaction mixture is acidified and extracted with ethyl acetate. The ethyl acetate layer is washed with water, dried over magnesium sulfate and concentrated to dryness in vacuo. The residue (14.6 g) is dissolved in ethyl acetate (150 ml) and dicyclohexylamine (11 ml) is added. The crystals are filtered and recrystallized from ethyl acetate, yield 5.7 g.m.p. 151°–152°. To convert the salt to the acid, the crystals are dissolved in a mixture of 5% aqueous potassium bisulfate (100 ml) and ethyl acetate (300 ml). The organic phase is washed once with water, dried over magnesium sulfate and concentrated to dryness in vacuo, yield 3.45 g.

(b) Synthesis of N-(2-Mercaptoacety)-L-Proline

N-(2-Benzoylthioacetyl)-L-proline (3.4 g) is dissolved in a mixture of water (10.5 ml) and concentrated ammonia (6.4 ml). After 1 hour, the reaction mixture is diluted with water and filtered. The filtrate is extracted with ethyl acetate and then acidified with concentrated hydrochloric acid, saturated with sodium chloride and extracted twice with ethyl acetate. The ethyl acetate extracts are washed with saturated sodium chloride and concentrated to dryness, yield 1.5 g. The product, N-(2-mercaptoacetyl)-L-proline is crystallized from ethyl acetate (m.p. 133°–135°).

EXAMPLE 30

Synthesis of N-(2-Benzoylthioacetyl)-L-Proline Methyl Ester

N-(2-Benzoylthioacetyl)-L-proline obtained in Example 29, step (a) is dissolved in methanol and an ethereal solution of diazomethane is added until there is a persistent yellow color. After 15 minutes, a few drops of acetic acid are added and the solvent is removed in vacuo to obtain N-(2-benzoylthioacetyl)-L-proline methyl ester.

EXAMPLE 31

Synthesis of N-(2-Mercaptoacetyl)-L-Proline Amide

The product of Example 30 is dissolved in 10% methanolic ammonia and the solution is stored at room temperature in a pressure bottle. When thin layer chromatographic analysis indicates that the two ester functions have been ammonolyzed, the reaction mixture is concentrated to dryness to obtain N-(2-mercaptoacetyl)-L-proline amide.

EXAMPLE 32

Synthesis of N-(3-Mercaptopropanoyl)-L-proline tert-butyl Ester

To a solution of L-proline tert-butyl ester (3.42 g) in dry tetrahydrofuran (10 ml) chilled in an ice bath, propiothiolactone (1.76 g) is added. After 5 minutes storage in the ice bath and 3 hours at room temperature, the reaction mixture is diluted with ethyl acetate (200 ml) and washed with 5% potassium bisulfate, and water. The organic layer is dried over magnesium sulfate and concentrated to dryness in vacuo. The residue N-(3-mercaptopropanoyl)-L-proline tert-butyl ester is crystallized from ether-hexane, yield 3.7 g, m.p. 57°–58°.

EXAMPLE 33

(a) Synthesis of 3-Acetylthio-2-Methylpropanoic Acid

A mixture of thioacetic acid (50 g) and methacrylic acid (40.7 g) is heated on the steam bath for 1 hour and then stored at room temperature for 18 hours. After confirming by nmr spectroscopy that complete reaction of the methacrylic acid has been achieved, the reaction mixture is distilled in vacuo and the desired 3-acetylthio-2-methylpropanoic acid is separated in the fraction with boiling point 128.5°–131° (2.6 mmHg.), yield 64 g.

(b) Synthesis of N-(3-Mercapto-2-methylpropanoyl)-L-Proline tert-butyl Ester L-Proline tert-butyl ester (5.1 g) is dissolved in dichloromethane (40 ml) and the solution stirred and chilled in an ice bath. Dicyclohexylcarbodiimide (6.2 g) dissolved in dichloromethane (15 ml) is added followed immediately by a solution of 3-acetylthio-2-methylpropanoic acid (4.9 g) in dichloromethane (5 ml). After 15 minutes stirring in the ice bath and 16 hours at room temperature, the precipitate is filtered off and the filtrate is concentrated to dryness in vacuo. The residue is dissolved in ethyl acetate and washed neutral. The organic phase is dried over magnesium sulfate and concentrated to dryness in vacuo. The residue, N-(3-acetylthio-2-methylpropanoyl)-L-proline tert-butyl ester, is purified by column chromatography (silica gel, chloroform), yield 7.9 g. The named product is obtained by following the procedure of Example 29, step (b).

EXAMPLE 34

Synthesis of N-(3-mercapto-2-D, L-methylpropanoyl)-L-proline

Methacryloyl chloride (4.16 g) is added to a solution of L-proline (3.45 g) in a mixture of water (100 ml) and sodium bicarbonate (12 g) chilled in an ice water bath, with vigorous stirring. When the addition is completed, the mixture is stirred at room temperature for two hours, and then extracted with ether. The aqueous phase is acidified with 1.0N hydrochloric acid and extracted with ethyl acetate. The organic phase is concentrated to dryness in vacuo, the residue is mixed with thiolacetic acid (3.5 g), a few crystals of azobisisobutyronitrile are added and the mixture is heated on the steam bath for two hours. The reaction mixture is dissolved in benzene acetic acid (75:25), and applied to a column of silica gel. Elution with the same solvent mixture yields the N-(3-acetylthio-2-D,L-methylpropanoyl)-L-proline. The named product is obtained by following the procedure of Example 29, step (b).

EXAMPLE 35

(a) Synthesis of N-[3-(Acetylthio-2-methylpropanoyl]-D,L-Pipecolic Acid 6.5 g (0.05 mole) of pipecolic acid are suspended in dimethylacetamide (200 mg), 9.0 g. (0.05 mole) of 3-acetylthio-2-methylpropanoul chloride is added dropwise. The temperature rises to 29° and a clear solution forms. Then 10.1 g of N-methylmorpholine is added all at once and the temperature rises to 34°. The mixture is heated on a steam bath for 1 hour when a clear solution forms. This is allowed to stand at room temperature overnight and the solid which precipitates is filtered to yield 6.1 g, m.p. 203°-204°. The solvent is removed and the viscous residue is triturated with water and 20% HCl. The yellow oil is extracted with 3×150 ml of ethyl acetate. The ethyl acetate extracts are dried over magnesium sulfate and removed to yield 14 g of N-[3-(acetylthio-2-methylpropanoly]-D,L-pipecolic acid as a viscous oil.

(b) Synthesis of N-[3-Mercapto-2-methylpropanoyl]-D,L-Pipecolic Acid.

Aqueous NH4OH (30 ml water and 20 ml conc. NH4OH) is stirred under nitrogen at 10° for 15 minutes. This is added to 13.0 g (0.05 m) of N-[3-(acetylthio)-2-methylpropanoyl]-D,L-pipecolic acid and the resulting solution is stirred for 10 minutes under nitrogen; then at room temperature for 50 minutes. It is then treated with water and 20% NaCl and the yello oil extracted with 3 z 150 ml of ethyl acetate. The ethyl acetate extract is dried over magnesium sulfate and removed to yield 11.1 g N-(3-mercapto-2-methyl-propanoyl)-D,L-pipecolic acid as a viscous oil. $R_f$ 0.62 [silica gel, benzene acetic acid (7:2)].

EXAMPLE 36

By substituting the appropriate activated acyl group for the chloroacetyl chloride of Example 29, step (a) and by substituting the appropriate chloride amino group for L-Pro of Example 29, step (a) and substantially following the procedures of Example 29, steps (a) and (b) and Examples 30 and 31, the mercapto compounds, HS -Z VIII, defined in Table 1 are obtained.

TABLE 1

| | $R_8$ | $R_8^1$ | $R_{13}$ | $R_{12}$ | q | n |
|---|---|---|---|---|---|---|
| (1) | H | H | H,3-OH | OH | 1 | 2 |
| (2) | H | H | H | OH | 1 | 1 |
| (3) | H | H | H | OH | 1 | 3 |
| (4) | H | H | OH | OH | 1 | 1 |
| (5) | H | $C_2H_5$ | H | OH | 1 | 2 |
| (6) | $CH_3$ | H | Cl | $OC_2H_5$ | 1 | 2 |
| (7) | $CH_3$ | $CH_3$ | H | OH | 1 | 2 |
| (8) | $CH_3$ | $C_6H_5CH_2$ | H | OH | 1 | 2 |
| (9) | $C_2H_5$ | H | H | OH | 1 | 1 |
| (10) | H | $C_4H_9$ | H | OH | 1 | 3 |
| (11) | H | H | H | $NH_2$ | 1 | 2 |
| (12) | H | H | H, 3-F | OH | 2 | 2 |
| (13) | H, $CH_3$ | H | H, 3-OH | OH | 2 | 2 |
| (14) | $CH_3, CH_3$ | H | H | OH | 2 | 1 |
| (15) | H | $C_2H_5$ | H | OH | 2 | 3 |
| (16) | H, $C_2H_5$ | $CH_3$ | H | $OCH_3$ | 2 | 2 |
| (17) | H | $CH_3$ | H, H, 3-OH | $OCH_3$ | 2 | 3 |
| (18) | — | H | H | OH | 0 | 2 |
| (19) | — | H | H, H, 4-OH | OH | 0 | 3 |
| (20) | — | $CH_3$ | H | $OC_2H_5$ | 0 | 1 |
| (21) | — | $CH_3$ | H | $NH_2$ | 0 | 3 |
| (22) | — | $C_4H_9$ | H, 4-Br | OH | 0 | 2 |
| (23) | — | H | H, 4-$CH_3$ | OH | 0 | 2 |
| (24) | — | $CH_3$ | OH | OH | 0 | 1 |
| (25) | $C_3H_7$ | H | H | $NH_2$ | 1 | 2 |
| (26) | H | $CH_3$ | H, H, 5-OH | OH | 1 | 3 |
| (27) | H | $CH_3$ | H | OH | 2 | 2 |
| (28) | $C_6H_5$-$C_2H_5$ | H | H, 4-OH | $OC_3H_7$ | 1 | 2 |
| (29) | $CH_3$ | H | $C_2H_5$ | $NH_2$ | 1 | 1 |
| (30) | H, $C_5H_{11}$ | $CH_3$ | H, 3-$C_4H_9$ | OH | 2 | 2 |

Examples 37–38 describe the synthesis of HS-Z where Z corresponds to formula XI. The procedures followed in these examples correspond to those in U.S. Pat. No. 4,070,361.

EXAMPLE 37 Synthesis of N-[[2-(Acetylthio)ethyl]sulfonyl]L-proline (a) N-(Vinylsulfonyl)-L-proline t-butyl ester L-Proline t-butyl ester (6.9 g 0.04 mole) and triethylamine (14 ml, 0.1 mole) are dissolved in 200 ml of dichloromethane and stirred in an ice bath while 2-chloroethanesulfonyl chloride (8.2 g, 0.05 mole) in 100 ml of dichloromethane is added over 20 minutes. After stirring 2 hours, the mixture is washed with 5% potassium bisulfate solution, saturated sodium bicarbonate solution and brine, then evaporated in vacuo. The semi-solid residue is chromatographed on 350 ml. silica gel using 1:1 ethyl acetate/hexane as eluant. The main fraction, comprising N-(vinylsulfonyl)-L-proline t-butyl ester is crystallized from ether/hexane, m.p. 84°-87° (7.1 g, 68%).

(b) N-[[2-(Acetylthio)ethyl]sulfonyl]-L-proline t-butyl ester

N-(Vinylsulfonyl)-L-proline t-butyl ester (5.0 g, 0.0192 mole), triethylamine (2.8 ml, 0.02 mole) and thiolacetic acid (1.43 ml, 0.02 mole) are mixed in 100 ml of ether and allowed to stand overnight. The mixture is washed with 5% potassium bisulfate solution, saturated sodium bicarbonate solution and brine, then evaporated in vacuo to a yellow oil. The procedure is repeated using half of the above quantities of triethylamine and thiolacetic acid. Workup as in part (a) affords the crude product, N-[[2-(acetylthio)ethyl]sulfonyl]-L-proline t-butyl ester, which is filtered through a short silical gel column and crystallized from ether/hexane, m.p. 46°–50° (2.9 g, 45%).

(c) N-[[2-Acetylthio)ethyl]sulfonyl]-L-proline

The t-butyl ester from part (b) (2.9 g, 0.0086 mole) is dissolved in 15 ml of anisole and 45 ml of trifluoroacetic acid and let stand 1 hour. The mixture is evaporated in vacuo to a gummy residue which is taken up in ethyl acetate and treated with a large volume of hexane. The supernatant is decanted, and the procedure repeated. The resulting semi-solid is crystallized from ethyl acetate-hexane, m.p. 63°–67°.

(d) Synthesis of N-[(2-Mercaptoethyl)sulfonyl]-L-proline

N-[[2-(Acetylthio)ethyl]sulfonyl]-L-proline (640 mg, 0.0023 mole) is dissolved in 5 ml of water and 5 mg of concentrated ammonia and stirred 1 hour under nitrogen. The solution is acidified with concentrated hydrochloric acid, extracted with ethyl acetate, and the extracts are washed with brine, dried (MgSO$_4$) and evaporated to an oily residue which is applied to a 75 ml silica gel column. Elution with 10% acetic acid/benzene affords a main fraction which is crystallized from chloroform/hexane, to obtain 440 mg (81%) of 1-[(2-mercaptoethyl)sulfonyl]-L-proline, m.p. 99°–101°.

EXAMPLE 38

By substituting the appropriate haloalkylsulfonyl halide for the 2-chloroethanesulfonyl chloride of Example 37 and by substituting the appropriate amino group for the L-Pro-t-butyl ester of Example 37 and substantially following the procedures of Examples 37, the mercapto compounds, HS-Z of formula XI, as set forth in Table 2 are obtained.

TABLE 2

| | $R_2$ of part B | | z |
|---|---|---|---|
| | | $R_2$ of part A$_2$ | |
| (1) | CH$_3$ | H | 2 |
| (2) | H | CH$_3$ | 2 |
| (3) | C$_3$H$_7$ | H | 2 |
| (4) | C$_2$H$_5$ | C$_2$H$_5$ | 2 |
| | | $R_2$ of A$_2$ radical | |
| (5) | C$_4$H$_9$ | H | 2 |
| (6) | H | H | 3 |
| (7) | CH$_3$ | C$_5$H$_{11}$ | 3 |
| (8) | CH$_3$ | H | 3 |
| (9) | C$_4$H$_9$ | CH$_3$ | 3 |
| (10) | CH$_3$ | CH$_3$ | 3 |

Examples 39–41 describe the synthesis of HS-Z where Z corresponds to formula II. The procedures followed in these examples are similar to those in U.S. Pat. No. 4,154,935.

EXAMPLE 39

(a) Synthesis of 3 Acetylthio-2-trifluoromethylpropanoic acid

A mixture of thiolactic acid (50 g) and 2-(trifluoromethyl)acrylic acid [M. W. Buxton, et al., *J. Chem Soc.*, 366 (1954)] (66 g) is heated on the steam bath for one hour and then stored at room temperature for eighteen hours. The reaction mixture is distilled in vacuo to give 3-acetylthio-2-trifluoromethylpropanoic acid.

(b) Synthesis of N-(3-Acetylthio-2-trifluoromethylpropanoyl-L-proline tert-butyl ester L-proline tert-butyl ester (5.1 g) is dissolved in dichloromethane (40 ml) and the solution is stirred and chilled in an ice bath. Dicyclohexylcarbodiimide (6.2 g) dissolved in dichloromethane (15 ml) is added followed immediately by a solution of 3-acetylthio-2-trifluoromethylpropanoic acid (6.5 g) in dichloromethane (5 ml). After fifteen minutes stirring in the ice bath and sixteen hours at room temperature, the precipitate formed is filtered off and the filtrate is concentrated to dryness in vacuo. The residue is dissolved in ethyl acetate and washed neutral. The organic phase is dried over magnesium sulfate and concentrated to dryness in vacuo to give N-(3-acetylthio-2-trifluoromethylpropanoyl)-L-proline tertbutyl ester.

(c) Synthesis of N-(3-Acetylthio-2-trifluoromethylpropanoyl)-L-proline

N-(3-Acetylthio-2-trifluoromethylpropanoyl)-L-proline tertbutyl ester (8 g) is dissolved in a mixture of anisole (55 ml) and trifluoroacetic acid (110 ml). After one hour storage at room temperature the solvent is removed in vacuo and the residue is precipitated several times from ether-hexane to give N-(3-acetylthio-2-trifluoromethylpropanoyl)-L-proline.

(d) Synthesis of N-(3-Mercapto-2-trifluoromethylpropanoyl)-L-proline

N-(3-Acetylthio-2-trifluoromethylpropanoyl)-L-proline (4 g) is dissolved in a mixture of water (8 ml) and concentrated ammonia (8 ml) under a blanket of nitrogen. After twenty-five minutes stirring at room temperature, the reaction mixture is chilled, acidified and extracted with ethyl acetate. The organic layer is concentrated to dryness in vacuo to yield N-(3-mercapto-2-trifluoromethylpropanoyl)-L-proline.

EXAMPLE 40

Synthesis of N-(2-mercapto-3,3,3-trifluoropropanoyl)-L-proline

To a solution of L-proline (5.75 g) in 1N sodium hydroxide (50 ml), chilled in an ice water bath, 2-bromo-3,3,3-trifluoropropanoic acid chloride (12 g) is added and the mixture is vigorously stirred at room temperature for three hours. A solution of thiolacetic acid (4 ml) and potassium carbonate (4.8 g) in water (50 ml) is added and the mixture is stirred at room temperature for sixteen hours. After extraction with ethyl acetate, the aqueous layer is acidified with concentrated hydrochloride acid and extracted again with ethyl acetate. This last organic phase is dried over magnesium sulfate and concentrated to dryness in vacuo. The residue is chromatographed on a silica gel column with a mixture of benzene-acetic acid (7:2) to yield N-(2-acetylthio-3,3,3-trifluoropropanoyl)-L-proline. The named product is obtained by following the procedure of step (d), Example 39.

EXAMPLE 41

By substituting the appropriate activated acyl group for the 2-bromo-3,3,3-trifluoropropanoic acid chloride in Example 40 or by substituting the appropriate thioacyl group for the 3-acetylthio-2-trifluoromethyl-propanoic acid in Example 39 and by substituting the appropriate amino group for the L-Pro of Example 40 or for the L-Pro-t-butyl ester of Example 39, and substantially following the procedures respectively of Example 40 or Example 39, the mercapto compounds, HS-Z(II), as set forth in Table 3 are obtained.

|      | $R_3$ | $R_3^1$ | $R_0$ | $R_0^1$ | $R_2$ | m |
|------|-------|---------|-------|---------|-------|---|
| (1)  | —     | H       | F     | F       | H     | 0 |
| (2)  | —     | F       | F     | F       | $C_2H_5$ | 0 |
| (3)  | —     | $CF_3$  | F     | H       | H     | 0 |
| (4)  | —     | $C_2H_5$ | F    | F       | $CH_3$ | 0 |
| (5)  | —     | $CH_3$  | F     | H       | H     | 0 |
| (6)  | —     | $C_4H_9$ | F    | F       | H     | 0 |
| (7)  | —     | $CF_3$  | F     | H       | $C_3H_7$ | 0 |
| (8)  | $CF_3$ | H      | H     | F       | H     | 1 |
| (9)  | $CF_3$ | $C_3H_7$ | F   | F       | $CH_3$ | 1 |
| (10) | $C_2H_5$ | $CH_3$ | F   | F       | H     | 1 |
| (11) | H     | H       | F     | F       | H     | 1 |
| (12) | $CF_3$ | H      | H     | H       | $C_4H_9$ | 1 |
| (13) | $C_5H_{11}$ | $CF_3$ | F | H     | H     | 1 |
| (14) | H     | $CH_3$  | F     | H       | H     | 1 |
| (15) | $CH_3$ | $C_2H_5$ | F   | H       | $CH_3$ | 1 |

Examples 42–43 describe the synthesis of HS-Z where Z corresponds to formula III. The procedures followed in these examples are similar to those set forth in U.S. Pat. No. 4,154,934.

EXAMPLE 42

(a) Synthesis of N-nitroso-L-proline

To a cooled suspension of 28.2 g of nitrosyl tetrafluoroborate in 300 ml of dry acetonitrile there is added, with vigorous stirring, over the course of 10 minutes, 18.4 g of L-proline, followed by a solution of 19 g of pyridine in 50 ml of acetonitrile during 15 minutes. The stirring is continued for an hour and the reaction mixture is then concentrated to dryness under reduced pressure. The residue is extracted with 3×200 ml of ethyl acetate, the ethyl acetate extracts are combined, washed twice with saturated sodium chloride solution that has been made slightly acidic with concentrated hydrochloric acid. The ethyl acetate solution is dried over anhydrous sodium sulfate, filtered and concentrated to dryness at room temperature under reduced pressure. The product, N-nitroso-L-proline melts at 108°–109° (dec.) after crystallization from a mixture of ether and petroleum ether (30°–60°).

(b) Synthesis of N-amino-L-proline

A solution of 10 g of N-nitroso-L-proline in 500 ml of 50% acetic acid is cooled in an ice bath and 40 g of zinc dust is added gradually, with vigorous stirring, at a rate that the temperature of the reaction mixture is maintained below 10°. The addition requires about 15 minutes. The unreacted zinc dust is removed by filtration and the filtrate treated with hydrogen sulfide to precipitate the zinc as zinc sulfide. The precipitated zinc sulfide is removed by filtration and the filtrate evaporated to dryness. The residue is dissolved in 30 ml of absolute ethanol and the solution allowed to remain overnight at 5°. The N-amino-L-proline, a yellow crystalline solid, is removed by filtration and melts at 153°–154° after drying.

(c) Synthesis of N-[[3-(Acetylmercapto)-1-oxopropyl]amino]-L-proline

To a suspension of 3.9 g of N-amino-L-proline and 6.06 g of N-methylmorpholine in 200 ml of dimethylacetamide is added 4.98 g of 3-acetylthiopropionyl chloride. The temperature of the reaction mixture rises to 34° spontaneously. The reaction mixture is then heated at 90° for 5 hours and allowed to cool to room temperature overnight. The crystalline solid, N-methylmorpholine hydrochloride, is removed by filtration and the filtrate concentrated under reduced pressure. The residue is dissolved in a minimum amount of 20% hydrochloric acid and the aqueous solution is then extracted with 3×150 ml of ethyl acetate. The ethyl acetate extracts are combined, dried over anhydrous magnesium sulfate, and then concentrated under reduced pressure to yield the desired N-[[3-(acetylmercapto)-1-oxopropyl]amino]-L-proline.

(d) Synthesis of N-[(3-Mercapto-1-oxopropyl)amino]-L-proline

Nitrogen is bubbled into a solution of 12 ml of concentrated aqueous ammonia in 25 ml of water at 10° for 15 minutes. To this solution there is added 5.8 g of N-[[3-acetylmercapto)-1-oxopropyl]amino]-L-proline and the resulting solution is stirred for 2-½ hours under nitrogen. It is then cooled in an ice bath and made strongly acidic with 20% hydrochloric acid. The mixture is extracted with 3×150 ml of ethyl acetate, the ethyl acetate extracts are dried over anhydrous magnesium sulfate and then concentrated under reduced pressure. The oily residue is triturated with ether, the ether decanted and the last traces of ether removed under reduced pressure. The oily residue is dissolved in water and lyophilized to yield N-[(3-mercapto-1-oxopropyl)amino]-L-proline hemihydrate as a viscous oil.

Analysis calcd. for $C_8H_{14}N_2O_3S.\frac{1}{2}H_2O$: C, 42.27; H, 6.65; N, 12.32, S, 14.11 Found: C, 42.59; H, 6.68; N, 12.29; S, 14.29.

EXAMPLE 43

By substituting the appropriate starting materials into Examples 42 and substantially following the procedures of Examples 42, the mercapto compound HS-Z (III), as set forth in Table 4 are obtained.

TABLE 4

|      | $R_4$ | $R_4^1$ | $R_9$ | $R_2$ | m | n |
|------|-------|---------|-------|-------|---|---|
| (1)  | —     | $C_2H_5$ | H    | H     | 0 | 1 |
| (2)  | —     | $CH_3$  | OH    | $CH_3$ | 0 | 1 |
| (3)  | —     | H       | H     | $C_3H_7$ | 0 | 1 |
| (4)  | —     | H       | H     | H     | 0 | 2 |
| (5)  | —     | $CH_3$  | H, 3-OH | H   | 0 | 2 |
| (6)  | —     | H       | H, 4-OH | $CH_3$ | 0 | 2 |
| (7)  | —     | $C_6H_5CH_2$ | H | H     | 0 | 2 |
| (8)  | —     | H       | H     | $C_4H_9$ | 0 | 3 |
| (9)  | —     | $C_3H_7$ | H, H, 5-OH | H | 0 | 3 |
| (10) | H     | H       | H     | H     | 1 | 1 |
| (11) | H     | H       | OH    | $CH_3$ | 1 | 1 |
| (12) | $C_2H_5$ | H    | $CH_3$ | H   | 1 | 1 |
| (13) | H     | H       | $CH_3$ | H, 3-I | H | 1 | 2 |
| (14) | H     | H       | H, 3-OH | $C_2H_5$ | 1 | 2 |
| (15) | $C_2H_5$ | $C_2H_5$ | H | H   | 1 | 2 |
| (16) | $C_6H_5CH_2CH_2$ | H | H, 4-OH | $CH_3$ | 1 | 2 |
| (17) | $CH_3$ | H      | H     | H     | 1 | 3 |
| (18) | H     | H       | H, H, 3-OH | $C_3H_7$ | 1 | 3 |
| (19) | H     | $C_4H_9$ | H, H, 4-OH | H | 1 | 3 |
| (20) | $CH_3$ | $C_2H_5$ | H   | H     | 1 | 3 |

Examples 44-46 describe the synthesis of HS-Z where Z is defined by formulae XA, XB or XC. The procedures followed in these examples are akin to those set out in U.S. Pat. No. 4,129,566.

EXAMPLE 44

(a) Synthesis of N-(3-Acetylthio-2-ethylpropanoyl)-L-3,4-dehydroproline

L-3,4-dehydroproline (3.4 g) is dissolved in 1.0N sodium hydroxide (30 ml) and the solution is chilled in an ice-water bath. 3-Acetylthio-2-ethylpropanoyl chloride (5.84 g) and 2N sodium hydroxide (15 ml) are added and the solution is stirred at room temperature for 3 hours. The mixture is extracted with ether, acidified and extracted with ethyl acetate. The organic phase is dried over magnesium sulfate and evaporated to dryness to yield N-(3-acetylthio-2-ethylpropanoyl)-L-3,4-dehydroproline.

(b) Synthesis of N-(2-Ethyl-3-mercaptopropanoyl)-L-3,4-dehydroproline

N-(3-Acetylthio-2-ethylpropanoyl)-L-3,4-dehydroproline (3 g) is dissolved in a mixture of water (10 ml) and concentrated ammonia (10 ml) under a blanket of nitrogen. After 25 minutes, the reaction mixture is acidified and extracted with ethyl acetate. The organic layer is dried over magnesium sulfate and evaporated to dryness to yield N-(2-ethyl-3-mercaptopropanoyl)-L-3,4-dehydroproline.

EXAMPLE 45

Synthesis of N-(2-mercaptopropanoyl)-D,L-4,5-dehydropiperidine-2-carboxylic acid D,L-4,5-dehydropiperidine-2-carboxylic acid (5.65 g) is dissolved in 1.0N aqueous sodium hydroxide (50 ml) and the solution is chilled in an ice-water bath with stirring. 2N Sodium hydroxide (25 ml) and 2-bromopropanoyl chloride (8.57 g) are added. The mixture is stirred at room temperature for one hour. A mixture of thioacetic acid (4.18 g) and potassium carbonate (4.8 g) in water (50 ml) is added and the mixture is stirred at room temperature for eighteen hours. After acidification, the mixture is extracted with ethyl acetate. The organic layer is dried over magnesium sulfate and concentrated to dryness in vacuo to yield N-(2-acetylthiopropanoyl)-D,L-4,5-dehydropiperidine-2-carboxylic acid. The named product is obtained by following the procedure of step b of Example 44.

EXAMPLE 46

By substituting the appropriate starting material into Examples 44 or 45, respectively, and substantially following the procedures of Examples 44 or 45, the mercapto compounds, HS-Z, as set forth in Table 5 are obtained.

TABLE 5

| | $R_2$ of B moiety | $R_2$ of $A_2$ moiety | m in B moiety of formulae XA, XB and XC | m in $A_2$ moiety |
|---|---|---|---|---|
| (1) | H | $C_2H_5$ | 0 | 0 |
| (2) | $C_3H_7$ | H | 0 | 0 |
| (3) | H | H | 0 | 0 |
| (4) | $CH_3$ | H | 0 | 1 |
| (5) | H | $C_4H_9$ | 0 | 1 |
| (6) | $CH_3$ | $C_3H_7$ | 1 | 0 |
| (7) | $C_5H_{11}$ | H | 1 | 0 |
| (8) | H | $CH_3$ | 1 | 0 |
| (9) | $CH_3$ | H | 1 | 1 |
| (10) | $C_2H_5$ | H | 1 | 1 |
| (11) | $CH_3$ | $CH_3$ | 1 | 1 |

Examples 47-49 describe the synthesis of HS-Z where Z corresponds to formula IX. The procedures followed in these examples are generally defined in U.S. Pat. No. 4,108,886.

EXAMPLE 47

(a) Synthesis of 2-[(3-Benzoylthiopropanoyl)amino]-2-methylpropanoic acid a-Aminiosobutyric acid (5.15 g) is dissolved in 59 ml. of 0.85N sodium hydroxide while stirring in an ice bath. To this, 25 ml. of 2N sodium hydroxide is added, followed by 8.5 g of 3-bromopropionyl chloride. The bath is removed, and the pH adjusted to 7.3 with 2N sodium hydroxide. After 2 hours, a solution of 7.5 g of thiobenzoic acid and 4.8 g of potassium carbonate in 50 ml of water is added. The reaction mixture is stirred overnight at room temperature, acidified with concentrated hydrochloric acid and extracted with ethyl acetate. The organic layer is dried and concentrated to dryness, yield 1.31 g. The product, 2-[(3-benzoylthiopropanoyl)amino]-2-methylpropanoic acid, is crystallized from ethylacetate-ether, yield 5.4 g, m.p. 142°-143°.

(b) Synthesis of 2-[(3-Mercaptopropanoyl)amino]-2-methylpropanoic acid 2.8 g of the product of Step (a) is treated with a mixture of 20 ml water and 20 ml of concentrated ammonium hydroxide solution under an argon blanket for one hour. The benzamide precipitate is filtered and the filtrate is extracted twice with ethyl acetate. The aqueous phase is concentrated in vacuo, acidified with concentrated hydrochloric acid and extracted with ethyl acetate. The organic layer is dried and concentrated to dryness in vacuo and the residual product 2-[(3-mercaptopropanoyl)amino]-2-methylpropanoic acid, is crystallized from acetonitrile, yield 1.2 g, m.p. 169°-170°.

EXAMPLE 48

Synthesis of 1-[(3-Mercaptopropanoyl)amino]cyclopentane carboxylic acid

1-Aminocyclopentane-1-carboxylic acid (6.45 g) is dissolved in 50 ml of 1N sodium hydroxide solution and stirred in an ice bath. To this 25 ml of 2N sodium hydroxide solution is added, followed immediately with 8.5 g of 3-bromopropionyl chloride. The bath is removed and the pH is about 7. Some crystals come out of solution. After 3.5 hours at room temperature, 54 ml of 1N sodium hydroxide solution is added and everything goes into solution. This is followed immediately with 4.12 g of thiolacetic acid. An additional 5 ml of 1N sodium hydroxide is added to bring the pH to near 8. After standing overnight, the mixture is acidified with concentrated hydrochloric acid, extracted with ethyl acetate, dried over magnesium sulfate, and concentrated to dryness in vacuo. The product, 1-[(3-acetylthiopropanoyl)amino]cyclopentane carboxylic acid, is first crystallized from ethyl acetate and hexane. This material is recrystallized from ethyl acetate, yield 3.655 g, m.p. 127°–128°. The named product is obtained by following the procedure of Step (b) of Example 47.

EXAMPLE 49

By substituting the appropriate starting materials into Example 46 and substantially following its procedure, the mercapto compounds, HS-Z (IX), as set forth in Table 6 are obtained.

TABLE 6

| | | | | Methylene bridge | | |
|---|---|---|---|---|---|---|
| | $R_2$ (B moiety) | $R_{14}$ | $R_{14'}$ | $R_2$ ($A_2$ moiety) | $R_{14}$-$R_{14'}$ | $R_{14}$-$R_2$ ($A_2$ moiety) | m |
| (1) | $CH_3$ | $C_2H_5$ | $CH_3$ | H | — | — | 0 |
| (2) | H | $CH_3$ | $C_4H_9$ | $CH_3$ | — | — | 1 |
| (3) | $C_3H_7$ | $CH_3$ | $C_2H_5$ | $C_2H_5$ | — | — | 1 |
| (4) | $CH_3$ | — | — | H | $(CH_2)_4$ | — | 0 |
| (5) | H | — | — | $C_3H_7$ | $(CH_2)_4$ | — | 1 |
| (6) | $C_5H_{11}$ | — | — | $CH_3$ | $(CH_2)_4$ | — | 1 |
| (7) | $CH_3$ | — | H | — | — | $(CH_2)_3$ | 1 |
| (8) | $C_4H_9$ | — | H | — | — | $(CH_2)_3$ | 1 |
| (9) | H | — | $CH_3$ | — | — | $(CH_2)_3$ | 1 |
| (10) | $C_2H_5$ | — | $C_3H_7$ | — | — | $(CH_2)_3$ | 0 |

Examples 50–53 describe the synthesis of HS-Z where Z corresponds to formula VII. The procedures followed in these examples are generally described in U.S. Pat. No. 4,053,651.

EXAMPLE 50

(a) Synthesis of N-(3-Benzoylthiopropionyl)-L-alanine

L-alanine (4.45 g) is dissolved in aqueous 1.0N sodium hydroxide (50 ml) and the solution is chilled in the ice bath with stirring. 2N sodium hydroxide (27 ml) and 3-bromopropionyl chloride (8.5 g) are added in that order, and the mixture is removed from the ice bath and stirred at room temperature for three and one-half hours. A mixture of thiobenzoic acid (7.5 g) and potassium carbonate (4.8 g) in water (50 ml) is added and the mixture is stirred at room temperature overnight. After acidification with concentrated hydrochloric acid the aqueous solution is extracted with ethyl acetate, and the organic phase is washed with water, dried and concentrated to dryness. The residue (14.9 g) is crystallized from ether to yield 7.1 g of N-(3-benzoylthiopropanoyl)-L-alanine, m.p. 99°–100°.

(b) Synthesis of N-(3-Mercaptopropanoyl)-L-alanine

N-(3-benzoylthiopropanoyl)-L-alanine (4.2 g) is dissolved in a mixture of water (7.5 ml) and concentrated ammonium hydroxide (6 ml). After one hour, the mixture is diluted with water, filtered and the filtrate is extracted with ethyl acetate. The aqueous phase is acidified with concentrated hydrochloric acid and extracted with ethyl acetate. The organic phase is washed with water, dried and concentrated to dryness in vacuo. The residue is crystallized from ethyl acetate-hexane to yield 1.87 g of N-(3-mercaptopropanoyl)-L-alanine, m.p. 79°–81°.

EXAMPLE 51

Synthesis of N-(3-mercapto-2-methylpropanoyl)-L-valine

L-valine (88 g) and sodium carbonate (40 g) are dissolved in water (1 l.) and the solution is chilled in an ice bath with vigorous stirring. 3-Acetylthio-2-methylpropanoyl chloride (135 g) and a solution of sodium carbonate (120 g) in 500 ml of water are added in five equal portions over a 15 minute period. After 1.5 hours, the reaction mixture is extracted with ethyl acetate, the aqueous phase is acidified with concentrated hydrochloric acid and extracted with ethyl acetate. The organic phase is washed with water, dried over magnesium sulfate and concentrated to dryness to yield 190 g of N-(3-acetylthio-2-methylpropanoyl)-L-valine. The named product is obtained by following the procedure of Step (b), Example 49.

EXAMPLE 52

By substituting the appropriate starting materials into Examples 50 or 51 and substantially following the procedures of Examples 50 or 51, the mercapto compounds, HS-Z (VIII), as specified in Table 7 are obtained.

TABLE 7

| | $R_4$ (B moiety) | $R_{4'}$ | $R_4$ ($A_2$ moiety) | $R_{11}$ | q |
|---|---|---|---|---|---|
| (1) | — | H | H | $-(CH_2)_4-NH_2$ | 0 |
| (2) | — | H | H | $-(CH_2)_3-NH-\overset{NH}{\overset{\|}{C}}-NH_2$ | 0 |
| (3) | — | $CH_3$ | H | $-CH_2CO_2H$ | 0 |
| (4) | — | H | $CH_3$ | $-CH_2CH(CH_3)_2$ | 0 |
| (5) | — | $C_2H_5$ | $CH_3$ | $C_6H_5CH_2$ | 0 |
| (6) | H | $C_6H_5CH_2$ | H | H | 1 |
| (7) | $CH_3$ | H | H | $CH_2OH$ | 1 |
| (8) | $C_4H_9$ | $CH_3$ | H | 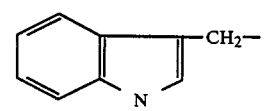 | 1 |
| (9) | H | H | $C_2H_5$ | $CH_3-S-CH_2CH_2-$ | 1 |
| (10) | $CH_3,H$ | H | $CH_3$ | H | 2 |
| (11) | H, $C_6H_5CH_2CH_2$ | $CH_3$ | H | 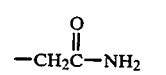 | 2 |

TABLE 7-continued

| | R4 (B moiety) | R4' | R4 (A2 moiety) | R11 | q |
|---|---|---|---|---|---|
| (12) | H | C5H11 | H | 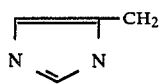—CH2 (N N ring) | 2 |
| (13) | H | H | H | —CH2SH | 2 |
| (14) | H, CH3 | H | C3H7 | CH3 | 2 |
| (15) | H | C3H7 | H | HO—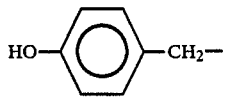—CH2— | 1 |
| (16) | CH3 | C2H5 | C6H5CH2 | —CH(CH3)(C2H5) | 1 |

Examples 53–56 describe the synthesis of HS-Z where Z corresponds to formula IVA or IVB. The procedures followed in these examples are generally described in U.S. Pat. Nos. 4,113,715 and 4,146,611.

EXAMPLE 53

(a) Synthesis of N,S-Diacetyl-D,L-cysteinyl-L-proline tert-butyl ester

To a solution of L-proline tert-butyl ester (0.85 g) and hydroxybenzotriazole (0.67 g) in methylene chloride (10 ml) chilled in an ice bath, dicyclohexylcarbodiimide (1.03 g) and N,S-diacetyl-D,L-cysteine (1.7 g) are added in that order. After fifteen minutes, the ice bath is removed and the mixture is stirred at room temperature overnight. The precipitate is filtered off and the filtrate is washed with 10% potassium bisulfate, water, saturated sodium bicarbonate and water. The organic phase is dried and concentrated to dryness in vacuo to give N,S-diacetyl-D,L-cysteinyl-L-proline tert-butyl ester as an oil. $R_f=0.25$ (silica gel, ethylacetate).

(b) Synthesis of N,S-Diacetyl-D,L-cysteinyl-L-proline

N,S-Diacetyl-D,L-cysteinyl-L-proline tert-butyl ester (1.9 g) is dissolved in a mixture of anisole (6 ml) and trifluoroacetic acid (12 ml) and the solution is stored at room temperature for one hour. The solvents are removed in vacuo and the residue is precipitated from ethyl acetate-ether-hexane, to obtain N,S-diacetyl-D,L-cysteinyl-L-proline, yield 1.08 g, m.p. 80°–140°.

(c) Synthesis of N-Acetyl-D,L-cysteinyl-L-proline

N,S-Diacetyl-D,L-cysteinyl-L-proline (0.3 g) is dissolved in a mixture of water (4 ml) and concentrated ammonia (4 ml) under a blanket of argon. The solution is stored for 30 minutes at room temperature, saturated with sodium chloride and extracted with ethyl acetate and chloroform. The organic layers are pooled and concentrated to dryness in vacuo to obtain N-acetyl-D,L-cysteinyl-L-proline, yield 0.1 g, $R_f=0.25$ (silica gel; benzene:acetic acid, 75:25).

EXAMPLE 54

(a) Synthesis of N-alpha-acetyl-3-acetylthiovalyl-L-proline t-butyl ester

By substituting N,S-diacetyl-penicillamine for the N,S-diacetyle-D,L-cysteine in the procedure of Example 52, Step (a), N-alpha-acetyl-3-acetylthiovalyl-L-proline t-butyl ester is obtained.

(b) Synthesis of N-alpha-acetyl-3-mercaptovalyl-L-proline

By substituting the product of Example 54, Step (a) for the N,S-diacetyl-D,L-cysteinyl-L-proline t-butyl ester in the procedure of Example 53, Step (b) and conducting Step (c) of Example 53 thereafter, the named product is obtained.

EXAMPLE 55

(a) Synthesis of Methyl N-(p-methoxybenzyl)nipecotate hydrochloride

A mixture of 23 g of methyl nipecotate, 24.3 g of potassium carbonate, and 52 g of p-methoxybenzyl trichloroacetate in 800 ml of toluene is refluxed under nitrogen for seventy-two hours. The mixture is cooled, the toluene removed in vacuo, the residue dissolved in chloroform, and this solution washed once with 400 ml of aqueous potassium carbonate and then with 400 ml of 10% hydrochloric acid. The chloroform solution is dried and concentrated in vacuo to a viscous brown oil. Trituration of this oil with ethyl acetate affords 30.7 g of methyl N-(p-methoxybenzyl)nipecotate hydrochloride as an off-white crystalline solid. Recrystallization from ethyl acetate yields the analytical sample, m.p. 150°–154°.

(b) Synthesis of N-(p-Methoxybenzyl)-3-methylene-2-piperidone

A solution of methyl N-(p-methoxybenzoyl)nipecotate hydrochloride (30.7 g) and 8.4 g of sodium hydroxide in 900 ml of methanol and 45 ml of water is stirred at room temperature for seventeen hours. The solution is evaporated to dryness in vacuo, the residue diluted with toluene, and this again evaporated in dryness in vacuo. To the residue is added 1 liter of acetic anhydride and 140 ml of triethylamine, and the resulting mixture is heated under reflux for four hours. The reaction mixture is evaporated to dryness in vacuo, the residue taken up in chloroform, washed with water, dried and concentrated in vacuo. The residual oil is chromatographed on silica gel using 1:1 hexane-ethyl acetate as the eluant, and yields 16.9 g of N-(p-methoxybenzyl)-3-methylene-2-piperidone as a chromatographically pure yellow oil. Alternatively, the oil can be distilled to give analytically pure N-(p-methoxybenzyl)-3-methylene-2-piperidone, m.p. 145°–155°/0.05 mm.

(c) Synthesis of 3-Methylene-2-piperidone

A solution of N-(p-methoxybenzyl)-3-methylene-2-piperidone (16.9 g) and 21.3 g of anisole in 400 ml of trifluoroacetic acid is refluxed under nitrogen for forty-eight hours. The solution is evaporated to dryness in vacuo, and the residue chromatographed on 900 g of silica gel using ethyl acetate as eluant, yielding 6.5 g of 3-methylene-2-piperidone as a crystalline solid.

(d) Synthesis of 2-Methylene-5-aminopentanoic acid hydrochloride

A solution of 2.6 g of 3-methylene-2-piperidone in 150 ml of 6N hydrochloric acid is refluxed for twenty-four hours. The cooled solution is extracted with chloroform, and the aqueous layer concentrated in vacuo to 3.8 g of glassy foam. The foam is heated with methanol, filtered through Celite (diatomaceous earth clarifying agent) to remove a small amount of insoluble material, and the filtrate is evaporated to dryness in vacuo, yielding 2.5 g of 2-methylene-5-aminopentanoic acid hydrochloride as a tan crystalline solid. Recrystallization from isopropanol gives the analytical sample, m.p. 138°-144°.

(e) Synthesis of 2-Methylene-5-(p-methoxybenzyloxycarbonyl)aminopentanoic acid

To a solution of 8.8 g of 2-methylene-5-aminopentanoic acid hydrochloride in 100 ml of water is added with stirring 6.36 g of magnesium oxide, followed by a solution of 12.2 g of p-methoxybenzyloxycarbonyl azide in 100 ml of dioxane, and the resulting mixture is stirred at room temperature for two days. The reaction mixture is filtered, and the filtrate diluted with 200 ml of ethyl acetate, two equivalents of Dowex 50 ion exchange resin is added, and the mixture is stirred at room temperature for two hours. The resin is then filtered off and washed with water. The layers in the filtrate are separated and the aqueous layer is extracted twice with ethyl acetate. The combined organic layers are dried and concentrated in vacuo to give 18.2 g of 2-methylene-5-(p-methoxybenzyloxycarbonyl)aminopentanoic acid as an amber oil which crystallizes on standing. This is used without further purification.

(f) Synthesis of 2-Acetylthiomethyl-5-(p-methoxybenzyloxycarbonyl)amino pentanoic acid A solution of 2-methylene-5-(p-methoxybenzyloxycarbonyl)amino pentanoic acid (53 mmoles) in 50 ml of thiolacetic acid is allowed to stand at room temperature for forty-eight hours. The solution is evaporated to dryness in vacuo, and the residue taken up in chloroform and applied to a silica gel column (700 g). Elution with 5% methanol in chloroform affords 14.2 g of 2-acetylthiomethyl-5-(p-methoxybenzyloxycarbonyl)amino pentanoic acid as an oil. Treatment of this oil with one equivalent of dicyclohexylamine in ether, followed by recrystallization from ethyl acetate, affords the corresponding dicyclohexylamine salt, m.p. 112°-114°.

(g) Synthesis of 2-Acetylthiomethyl-5-(p-methoxybenzyloxycarbonyl)amino pentanoic acid N-hydroxysuccinimide ester To a solution of 3.7 g of 2-acetylthiomethyl-5-(p-methoxybenzyloxycarbonyl)amino pentanoic acid and 1.21 g of N-hydroxysuccinimide in 60 ml of dichloromethane at 0°-5° is added 2.16 g of N,N'-dicyclohexylcarbodiimide over twenty minutes with stirring. The resulting mixture is stirred overnight at 0°-5°. The precipitated dicyclohexylurea is filtered off, the filtrate concentrated in vacuo and the residue taken up in ethyl acetate and washed through a silica gel column to give 4.6 g of 2-acetylthiomethyl-5-(p-methoxybenzyloxycarbonyl)amino pentanoic acid N-hydroxysuccinimide ester as an oil, which crystallizes on trituration with ether. Recrystallization from ethyl acetate-hexane affords the analytical sample, m.p. 85°-87°.

(h) Synthesis of N-[2-Acetylthiomethyl-5-(p-methoxybenzyloxycarbonylamino)pentanoyl]-L-proline tert-butyl ester By substituting 2-acetylthiomethyl-5-(p-methoxybenzyloxycarbonylamino)pentanoic acid for the N,S-diacetyl-D,L-cysteine in the procedure of Example 53, Step (a), N-[2-acetylthiomethyl-5-(p-methoxybenzyloxycarbonylamino)pentanoyl]-L-proline tert-butyl ester is obtained.

(i) Synthesis of N-(2-Acetylthiomethyl-5-aminopentanoyl-L-proline, trifluoroacetate salt N-[2-Acetylthiomethyl-5-(p-methoxybenzyloxycarbonylamino)pentanoyl]-L-proline tert-butyl ester (2 g) is dissolved in a mixture of trifluoroacetic acid (15 ml) and anisole (6 ml). The solution is stored at room temperature for one hour, the solvents are removed in vacuo and the residue is precipitated from ethyl acetate-ether to yield N-(2-acetylthiomethyl-5-aminopentanoyl)-L-proline, trifluoroacetate.

(j) Synthesis of N-(5-Amino-2-mercaptomethylpentanoyl)-L-proline

N-(2-Acetylthiomethyl-5-aminopentanoyl)-L-proline trifluoroacetate (1 g) is dissolved in a mixture of water (12 ml) and concentrated ammonia (12 ml) under a blanket of argon. The solution is stored twenty minutes at room temperature, concentrated to 5 ml and applied to a column of Dowex 50 ion exchange resin in the hydrogen cycle. The column is washed with water and N-(5-amino-2-mercaptomethylpentanoyl)-L-proline is eluted with a buffer of pyridine-acetic acid at pH 6.5.

EXAMPLE 56

By substituting the appropriate starting materials into Examples 53, Steps (a)-(c); 54; Steps (a) and (b) or 55, Steps (a)-(j) and substantially following the respective procedures of formula IVA and IVB as set forth, the mercapto compounds, HS-Z in Table 8 are obtained.

TABLE 8

| | $R_4$ | $R_6$ | $R_{10}$ | $R_{11}$ | methylene bridge $R_{10}$-$R_{11}$ | $R_2$ ($A_2$ moiety) | m | p | $R_2$ ($B_2$ moiety) | $R_{2'}$ |
|---|---|---|---|---|---|---|---|---|---|---|
| (1) | H | H | H | $CH_3$ | — | H | 1 | 0 | H | H |
| (2) | $CH_3$ | H | H | H | — | H | 1 | 0 | H | H |

TABLE 8-continued

| | $R_4$ | $R_6$ | $R_{10}$ | $R_{11}$ | methylene bridge $R_{10}$-$R_{11}$ | $R_2$ ($A_2$ moiety) | m | p | $R_2$ (B moiety) | $R_{2'}$ |
|---|---|---|---|---|---|---|---|---|---|---|
| (3) | H | —CHO | $CH_3$ | $CH_2OH$ | — | $CH_3$ | 1 | 0 | H | H |
| (4) | $C_3H_7$ | H | H | —$CH_2CH_2CO_2H$ | — | H | 0 | 1 | — | — |
| (5) | H | $CH_3C(O)$— | — | — | $(CH_2)_3$ | H | 0 | 1 | — | — |
| (6) | H | H | H | indol-3-ylmethyl ($-CH_2-$) | — | $C_2H_5$ | 0 | 1 | — | — |
| (7) | H | —C(=NH)NH_2 | — | — | $(CH_2)_4$ | H | 1 | 1 | — | — |
| (8) | $C_2H_5$ | $C_2H_5C(O)$— | — | — | $(CH_2)_3$, 3-OH | $C_4H_9$ | 1 | 1 | — | — |
| (9) | $CH_3$ | H | H | —$(CH_2)_4NH_2$ | — | H | 1 | 1 | — | — |
| (10) | H | H | — | — | $(CH_2)_4$, 5-OH | H | 0 | 2 | — | — |
| (11) | H | $C_3H_7C(O)$— | $C_2H_5$ | imidazol-4-ylmethyl ($-CH_2-$) | — | H | 0 | 2 | — | — |
| (12) | $CH_3$ | H | H | —$CH(CH_3)_2$ | — | H | 1 | 2 | — | — |
| (13) | $C_6H_5CH_2$ | H | H | —$CH_2CH(CH_3)_2$ | — | H | 1 | 2 | — | — |
| (14) | H | $CH_3C(O)$— | — | — | $(CH_2)_3$, 4-F | $CH_3$ | 1 | 2 | — | — |
| (15) | H | H | H | —$CH_2CH_2SCH_3$ | — | H | 0 | 3 | — | — |
| (16) | $CH_3$ | —C(=NH)NH_2 | $CH_3$ | 4-hydroxybenzyl (HO-C$_6$H$_4$-CH$_2$—) | — | H | 0 | 3 | — | — |
| (17) | H | H | H | $C_6H_5CH_2$ | — | H | 1 | 3 | — | — |
| (18) | H | $C_4H_9C(O)$— | H | —$CH_2SH$ | — | H | 1 | 3 | — | — |
| (19) | $CH_3$ | H | — | — | $(CH_2)_3$ | H | 0 | 4 | — | — |
| (20) | H | $CH_3C(O)$— | H | —$CH_2C(O)NH_2$ | — | $CH_3$ | 0 | 4 | — | — |
| (21) | H | H | H | —$CH_2(CH_2)_2NHC(=NH)NH_2$ | — | H | 1 | 4 | — | — |
| (22) | H | HC(O)— | —$CH_2OH$ | $CH_3$ | — | H | 1 | 4 | — | — |

Examples 57–61 describe the synthesis of HS-Z where Z corresponds to formula V. The procedures followed in these examples are generally described in U.S. Pat. No. 4,116,962.

EXAMPLE 57

(a) Synthesis of 2-(Acetylthiomethyl)-3-(acetylthio)propanoic acid

A solution of 3.36 g (40 mmoles) of thioacetic acid in 40 ml of N-potassium hydroxide is added dropwise to a solution of 2-bromomethyl-3-bromopropanoic acid in 1.0N potassium hydroxide (20 ml). The mixture is stirred at room temperature overnight, acidified with concentrated hydrochloric acid and extracted with ethyl acetate. The organic layer is dried and concentrated in vacuo. The residue is converted into a dicyclohexylammonium salt (m.p. 116°–118°) and the salt converted back into the free acid, 2-(acetylthiomethyl)-3-(acetylthio)propanoic acid, by distribution between ethyl acetate and 10% potassium bisulfate.

(b) Synthesis of N-[(2-Acetylthiomethyl)-3-(acetylthio)propanoyl]-L-proline

To a solution of L-proline (1.44 g) and sodium carbonate (2.7 g) in water (25 ml) in an ice bath, 2-(acetylthiomethyl)-3-(acetylthio)propanic acid chloride (3.9 g—prepared from 2-(acetylthiomethyl)-3-(acetylthio)-propanic acid and thionyl chloride) is added and the mixture is vigorously stirred at room temperature for two hours. After extraction with ethyl acetate, the aqueous layer is acidified and extracted with ethyl acetate. The organic layer is dried and concentrated to dryness. The residue is chromatographed on a column of silica gel with a mixture of benzene-acetic acid (7:1). The fractions containing the desired material are pooled and concentrated to dryness to yield N-[(2-acetylthiomethyl)-3-(acethylthio)-propanoyl]-L-proline as an oil (1.3 g). $R_f$=0.3 (silica gel:benzene-acetic acid, 75:25).

(c) Synthesis of N-(2-Mercaptomethyl-3-mercaptopropanoyl)-L-proline

N-[(2-Acetylthiomethyl-3-(acetylthio)propanoyl]-L-proline (1.2 g) is dissolved in a mixture of water (12 ml) and concentrated ammonia (12 ml) under an atmosphere of argon. After twenty minutes, the mixture is acidified with concentrated hydrochloric acid. The crystalline precipitate N-(2-mercaptomethyl-3-mercaptopropanoyl)-L-proline is filtered and dried, yielding 0.63 g, m.p. 138°–140°.

EXAMPLE 58

(a) Synthesis of 3-(Acetylthio)-2-(methylthiomethyl)propanoic acid

A mixture of 3-(methylthiomethyl)acrylic acid (5.5 g) and thiolacetic acid (5 ml) is heated in the steam bath until disappearance of vinyl proton absorption in the nmr. The mixture is concentrated to remove the excess thiolacetic acid to obtain 3-(acetylthio)-2-(methylthiomethyl)propanoic acid.

(b) Synthesis of N-[(3-Acetylthio)-2-methylthiomethyl)propanoyl]-L-proline

To a solution of L-proline (1.44 g) and sodium carbonate (2.7 g) in water (25 ml) in an ice bath, 3-(acetylthio)-2-(methylthiomethyl)propanoic acid chloride (prepared from the acid of Example 58, Step (a) with thionyl chloride) (3.6 g) is added, and the mixture is vigorously stirred at room temperature for two hours. After extraction with ethyl acetate, the aqueous layer is acidified and extracted with ethyl acetate. The organic layer is dried and concentrated to dryness in vacuo to give N-[3-(acetylthio)-2-methylthiomethyl)propanoyl]-L-proline.

(c) Synthesis of N-[3-Mercapto-2-(methylthiomethyl)propanoyl]-L-proline

N-[(3-(acetylthio)-2-(methylthiomethyl)propanoyl]-L-proline (1.2 g) is dissolved in a mixture of water (12 ml) and concentrated ammonia (12 ml) under a blanket of argon. After twenty minutes, the reaction mixture is acidified and extracted with ethyl acetate. The organic layer is dried and concentrated to dryness to yield N-[(3-mercapto-2-methylthiomethyl)propanoyl]-L-proline.

EXAMPLE 59

Synthesis of N-(2-Hydroxymethyl)-3-mercaptopropanoyl)-L-proline

N-[2-acetoxymethyl-3-(acetylthio)propanoyl]-L-proline (1.5 g) is dissolved in a mixture of water (12 ml) and concentrated ammonia (12 ml) under a blanket of argon. After one hour, the reaction mixture is concentrated to ca. dryness, diluted with water and the solution applied to a column of cation exchange resin (Dowex 50) in the hydrogen cycle. The water eluate is concentrated to small volume and freeze-dried to yield N-(2-hydroxymethyl-3-mercaptopropanoyl)-L-proline.

EXAMPLE 60

(a) Synthesis of N-[2-Benzoylthio-3-methoxybutanoyl]-L-proline

To a solution of L-proline (5.75 g) in N sodium hydroxide (50 ml) chilled in an ice bath, 2N sodium hydroxide (25 ml) and 2-bromo-3-methoxybutyric acid chloride [obtained from 2-bromo-3-methoxybutyric acid [*J. Am. Chem. Soc.*, 71, 1096, (1949)] and thionyl chloride] (10.7 g) are added, with vigorous stirring. After three hours, thiobenzoic acid (7.5 g) and potassium carbonate (4.8 g) are added and the mixture is stirred at room temperature overnight. The reaction mixture is acidified and extracted with ethyl acetate. The organic layer is concentrated to dryness and the residue is chromatographed on a column of silica gel with benzene-acetic acid to yield N-[2-benzoylthio-3-methoxybutanoyl]-L-proline.

(b) Synthesis of N-[2-Mercapto-3-methoxybutanoyl-L-proline

By substituting N-[2-benzoylthio-3-methoxybutanoyl]-L-proline for the N-[3-acetylthio-2-(methylthiomethyl)propanoyl]-L-proline in the procedure of Example 56, Step (c), N-[2-mercapto-3-methoxybutanoyl]-L-proline is obtained.

EXAMPLE 61

By substituting the appropriate starting materials into Examples 57–60 and substantially following the procedures of Examples 57–60 respectively, the mercapto compounds, HS-Z (V), set forth in Table 9 are obtained.

TABLE 9

| | X | $R_2$ (B moiety) | $R_7$ | $R_{10}$ | $R_{11}$ | methylene bridge $R_{10}$-$R_{11}$ | $R_2$ ($A_2$ moiety) | m | p |
|---|---|---|---|---|---|---|---|---|---|
| (1) | S | — | $C_2H_5$ | H | H | — | H | 0 | 0 |
| (2) | O | — | H | — | — | $(CH_2)_3$ | $CH_3$ | 0 | 0 |

TABLE 9-continued

| | X | $R_2$ (B moiety) | $R_7$ | $R_{10}$ | $R_{11}$ | methylene bridge $R_{10}$-$R_{11}$ | $R_2$ ($A_2$ moiety) | m | p |
|---|---|---|---|---|---|---|---|---|---|
| (3) | S | — | HC(=O)— | H | —CH$_2$CO$_2$H | — | H | 1 | 0 |
| (4) | O | — | H | — | — | (CH$_2$)$_3$, 3-Cl | H | 1 | 0 |
| (5) | S | C$_2$H$_5$ | H | CH$_3$ | —CH(OH)CH$_3$ | — | H | 0 | 1 |
| (6) | S | H | CH$_3$ | H | (indol-3-ylmethyl) | — | H | 1 | 1 |
| (7) | O | H, CH$_3$ | C$_4$H$_9$ | — | — | (CH$_2$)$_4$ | C$_2$H$_5$ | 0 | 2 |
| (8) | S | H | CH$_3$C(=O)— | H | —CH$_2$SH | — | H | 0 | 2 |
| (9) | S | H | H | CH$_2$OH | (CH$_2$)$_4$NH$_2$ | — | H | 1 | 2 |
| (10) | O | CH$_3$, H | C$_3$H$_7$ | — | — | (CH$_2$)$_3$, 3-OH | C$_4$H$_9$ | 1 | 2 |
| (11) | S | H | C$_2$H$_5$C(=O)— | H | (imidazol-4-ylmethyl) | — | H | 0 | 3 |
| (12) | S | H, H, C$_3$H$_7$ | H | H | —CH(CH$_3$)$_2$ | — | H | 0 | 3 |
| (13) | S | H | C$_3$H$_7$C(=O)— | — | — | (CH$_2$)$_4$, 5-OH | H | 1 | 3 |
| (14) | O | H | H | H | CH$_3$SCH$_2$ | — | CH$_3$ | 1 | 3 |
| (15) | O | H | CH$_3$ | C$_3$H$_7$ | —CH$_2$CH$_2$SCH$_3$ | — | H | 0 | 4 |
| (16) | O | H | H | H | C$_6$H$_5$CH$_2$ | (CH$_3$)$_2$ | H | 0 | 4 |
| (17) | O | H | H | H | —CH(CH$_3$)(C$_2$H$_5$) | — | H | 1 | 4 |
| (18) | S | H | CH$_3$C(=O)— | H | CH$_3$ | — | H | 1 | 4 |

Examples 62–66 describe the synthesis of HS-Z where Z corresponds to formula VI. The procedures followed in these examples generally are described in U.S. Pat. No. 4,091,024.

EXAMPLE 62

(a) Synthesis of 3-acetylthio-2-methoxycarbonylmethyl propanoic acid

A mixture of thiolacetic acid (12.5 g) and 3-methoxycarbonyl-2-methylenepropanoic acid (17.1 g) are heated on a steam bath for two hours. The reaction is concentrated in vacuo and the residue is dissolved in ethyl acetate (125 ml) and dicyclohexylamine (35 ml) is added. The crystals are filtered, dried and recrystallized from ethyl acetate to yield 37.8 g, m.p. 120°–121°. This dicyclohexylammonium salt of 3-acetylthio-2-methoxycarbonylmethylpropanoic acid is converted to the free acid by distribution between a system of ethyl acetate and 10% aqueous potassium bisulfate.

(b) Synthesis of N-[3-(acetylthio)-2-methoxycarbonylmethyl)-propanoyl]-L-proline t-butyl ester To a solution of L-proline t-butyl ester (1.71 g) and 3-hydroxybenzotriazole (1.35 g) in dichloromethane (15 ml), dicyclohexylcarbodiimide (2.06 g) and the product of Step (a) (2.2 g) are added. After 18 hours stirring at room temperature, the precipitate formed is filtered off, the filtrate is washed neutral, dried and concentrated to dryness to yield 3.7 g of the named product, $R_f$=0.8 (silica gel-ethyl acetate).

(c) Synthesis of N-[3-(acetylthio)-2-(methoxycarbonylmethyl)-propanoyl]-L-proline 2.9 g of the product from Step (b) is dissolved in a mixture of trifluoroacetic acid (17.5 ml) and anisole (8.4 ml).

After one hour storage at room temperature, the excess trifluoroacetic acid is removed in vacuo and the residue is precipitated twice from ether-hexane to yield 2.1 g of the named product. $R_f$=0.4 (silica-benzene:acetic acid, 75:25).

(d) Synthesis of N-[3-Mercapto-2-(methoxycarbonylmethyl)-propanoyl]-L-proline 2.1 g of the product of Step (c) is dissolved in a mixture of water (35 ml) and concentrated ammonia (35 ml) under a blanket of argon. After 20 minutes, the solution is chilled in an ice bath, made acidic with concentrated hydrochloric acid, saturated with sodium chloride and extracted with ethyl acetate. The organic layer is dried and concentrated to dryness in vacuo to yield 1.1 g of the named product that is purified by chromatography on silica gel (benzene:acetic acid, 75:25) $R_f=0.35$ (silica gel-benzene:acetic acid, 75:25).

EXAMPLE 63

Synthesis of N-[2-Carboxymethyl-3-mercaptopropanoyl]-L-proline

To a solution of the product from Example 62, Step (d) (3.0 g) in methanol (60 ml), 1N sodium hydroxide (60 ml) is added. After 4 hours, the solution is applied to a column of Dowex 50 ion exchange resin in the hydrogen cycle, and the desired material is eluted with water to yield 2.3 g of the named product, $R_f=0.2$ (silica gel-benzene:acetic acid, 75:25).

EXAMPLE 64

Synthesis of N-[2-carbamoylmethyl-3-mercaptopropanoyl]-L-proline 2.1 g of the product from Example 62, Step (d) is dissolved in a mixture of water (40 ml) and concentrated ammonia (40 ml). After one hour the reaction mixture is concentrated in ⅓ volume, and applied to a column of Dowex 50 resin in the hydrogen cycle. The product is eluted with water. The aqueous is extracted with ethyl acetate and then concentrated to dryness to yield 1.4 g of the named product, $R_f=0.50$ (silica gel-chloroform:methanol:acetic acid:water).

EXAMPLE 65

Synthesis of N-[2-([N-butylcarbamoyl]methyl)-3-mercaptopropanoyl]-L-proline

By substituting 3-(acetylthio)-2-[(N-butylcarbamoyl)methyl]propanoic acid for the 3-(acetylthio)-2-(methoxycarbonylmethyl)propanoic acid in Example 62, Step (b) and substantially following the procedures of Example 62, Steps (b)-(d), the named product is obtained.

EXAMPLE 66

By substituting the appropriate starting materials into Examples 62-65 and substantially following, respectively, the procedures of Examples 62-65, the mercapto compounds, HS-Z (VI), as specified in Table 10 are obtained.

TABLE 10

| | $R_5$ | $R_{10}$ | $R_{11}$ | methylene bridge $R_{10}$-$R_{11}$ | $R_2$ | m | p |
|---|---|---|---|---|---|---|---|
| (1) | CN | H | $CH_3$ | — | H | 0 | 0 |
| (2) | $CO_2H$ | H | H | — | H | 0 | 0 |
| (3) |  —C(=O)—NHC$_3$H$_7$ | $C_2H_5$ | —CH(CH$_3$)$_2$ | — | $CH_3$ | 1 | 0 |
| (4) |  —C(=O)—OC$_2$H$_5$ | — | — | $(CH_2)_4$ | H | 1 | 0 |
| (5) |  —C(=O)—NH$_2$ | H | —CH$_2$OH | — | $C_4H_9$ | 0 | 1 |
| (6) | $CO_2H$ | H | $(CH_2)_4NH_2$ | — | H | 0 | 1 |
| (7) |  —C(=O)—OC$_5$H$_{11}$ | — | — | $(CH_2)_3$, 3-OH | H | 0 | 2 |
| (8) |  —C(=O)—NHCH$_3$ | H | 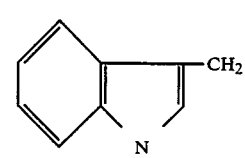 (indol-3-ylmethyl) | — | H | 0 | 2 |
| (9) |  —C(=O)—NH$_2$ | $C_3H_7$ | —CH$_2$—SH | — | H | 1 | 2 |
| (10) | CN | H | 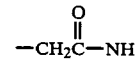 —CH$_2$C(=O)—NH$_2$ | — | $C_2H_5$ | 1 | 2 |
| (11) | $CO_2H$ | — | — | $(CH_2)_4$, 4-OH | H | 0 | 3 |
| (12) |  —C(=O)—NH | H | —CH$_2$CO$_2$H | — | H | 0 | 3 |
| (13) | CN | H | 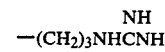 —(CH$_2$)$_3$NHC(=NH)NH$_2$ | — | H | 1 | 3 |

TABLE 10-continued

| | $R_5$ | $R_{10}$ | $R_{11}$ | methylene bridge $R_{10}-R_{11}$ | $R_2$ | m | p |
|---|---|---|---|---|---|---|---|
| (14) | $-\overset{\underset{\|}{O}}{C}-OCH_3$ | H | ⌈──┐-CH$_2$- ⌊N  N⌋ ⟍⟋ | — | H | 0 | 4 |
| (15) | $-\overset{\underset{\|}{O}}{C}-NHC_2H_5$ | CH$_3$ | C$_6$H$_5$CH$_2$- | — | H | 1 | 4 |

Examples 67–76 describe further synthesis of HS-Z.

EXAMPLE 67

(a) Synthesis of 3-acetylthiopropanoyl-L-proline-t-butyl ester 3-acetylthiopropanoic acid, 0.865 g, was dissolved in 2 ml redistilled tetrahydrofuran (THF) and cooled to 0° C. A cooled solution of dicyclohexylcarbodiimide (1.2031 g) in 2 ml of THF was added, following which a cooled solution of L-proline-t-butyl ester (1 g) was added. The reaction mixture was stirred at 0° C. for one hour, than at 4° C. overnight. The reaction mixture was then filtered and the precipitate was washed with ethyl acetate. Solvents of the filtrates were removed under reduced pressure in a rotary evaporator. The residue was dissolved in ethyl acetate which was then washed three times with cold 1N citric acid, twice with saturated NaCl, twice with cold 1N NaHCO$_3$ and three times with saturated NaCl. The solution was dried over anhydrous MgSO$_4$ and filtered. The solvent was removed under reduced pressure in a rotary evaporator at 30° C. yielding a clear colorless oily product in approximately 87% yield. The product migrated as a single spot in thin layer chromatography in all five solvent systems.

(b) Synthesis of 3-mercaptopropanoyl-L-proline

The product of Step (a), 3-acetylthiopropanoyl-L-proline-t-butyl ester (0.5 g) was mixed with 4.5 ml of 5.5N methanolic ammonia at room temperature under nitrogen for one hour to remove the acetyl group. The solvent was then removed at 25° C. with a rotary evaporator. After the product was taken up in methanol and re-evaporated twice more in the rotary evaporator, the clear oily residue was dissolved in ethyl ether, washed twice with 5% potassium bisulfate and once with saturated NaCl, dried over MgSO$_4$ and filtered. Residual solvent was removed in vacuo to yield a clear oily product, migrating as a single spot on thin layer chromatography in three separate solvent systems. The t-butyl ester protecting group was removed by reaction with trifluoroacetic acid in anisole.

EXAMPLES 68–70

By substituting 2-acetylthiopropanoic acid, 3-acetylthio-2-D-methylpropanoic acid, or 3-acetylthio-2-D,L-methylpropanoic acid for the 3-acetylthiopropanoic acid in Example 67, Step (a), and substantially following the procedures of Steps (a) and (b) thereof, the following compounds are obtained. By removing the t-butyl ester protecting group of trifluoroacetic acid in anisole as a first step, the dicyclohexylamine salt can be formed to assist in the resolution of isomers. The acetyl protecting group can be removed in a second step using methanolic ammonia, as described in Step (b) of Example 67.

| Example | Compound |
|---|---|
| 68 | 2-mercaptopropanoyl-L-proline |
| 69 | 3-mercapto-2-D-methylpropanoyl-L-proline |
| 70 | 3-mercapto-2-D,L-methylpropanoyl-L-proline. |

EXAMPLE 71

Synthesis of 3-mercapto-2-methyl-propanoyl-L-3,4-dehydroproline

L-3,4-dehydroproline ($\Delta^3$Pro) (1 mmole) is dissolved in DMF and the solution is cooled to $-15°$ C. The solution is neutralized by adding one equivalent of N-ethyl morpholine. In a separate reaction vessel at $-10°$ C., one equivalent of 3-acetylthio-2-methyl-propanoic acid in an equal volume of DMF is mixed with a 1.1 equivalent of 1,1'-carbonyldiimidazole, and the solution is stirred for one hour. The first solution containing $\Delta^3$Pro is mixed with the second, containing 3-acetylthio-2-methyl propanoic acid while maintaining the temperature at $-10°$ C. The combined solution is stirred for one hour at $-10°$ C. The solution is then allowed to warm slowly to room temperature. The solvent is removed on a rotary evaporator under reduced pressure at 40° C. Ethyl acetate (25 ml) is added and the solution is cooled to 0° C. Two ml of 1N citric acid is added, the two phases are mixed and then allowed to separate. The phases are separated with a separating funnel, and the organic phase is washed twice more with 2 ml 1N citric acid, two times with saturated NaCl and finally dried over anhydrous MgSO$_4$. The MgSO$_4$ is removed by filtration, and the solvent is removed with a rotary evaporator. The residue is dissolved and recrystallized from a non-polar solvent such as benzene to yield 3-acetylthio-2-D,L-methylpropanoyl-L-3,4-dehydroproline. When the 2-D-methyl isomer is desired, the residue is dissolved in acetonitrile (approximately 3 ml) and the solution is warmed to 40° C. One equivalent of dicyclohexylamine is added, and the solution is allowed to stand at room temperature overnight. The crystals are collected by filtration and are washed three times with acetonitrile. When further purification is required, the material can be recrystallized from isopropanol. The acetyl protecting group can be removed as in Example 65, Step (b).

EXAMPLES 72–75

By substituting D,L-3,4-dehydroproline, L-3-hydroxyproline, L-4-hydroxyproline, or L-thiazolidine-4 carboxylic acid for the L-3,4-dehydroproline in Example 71 and substantially following the procedure of Example 71, the following compounds are obtained.

| Example | Compound |
|---|---|
| 72 | 3-mercapto-2-D-methylpropanoyl-D,L-3,4-dehydroproline |
| 73 | 3-mercapto-2-D-methylpropanoyl-L-3-hydroxyproline |
| 74 | 3-mercapto-2-D-methylpropanoyl-L-4-hydroxyproline |
| 75 | 3-mercapto-2-D-methylpropanoyl-L-thiazolidine-4 carboxylic acid |

EXAMPLE 76

Similarly, by substituting 3-acetylthiopropanoic acid or 2-acetylthiopropanoic acid for the 3-acetylthio-2-methyl propanoic acid of Examples 72–75, the L-3,4-dehydroproline, D-L-3,4-dehydroproline, L-3-hydroxyproline, L-4-hydroxyproline and L-thiazolidine-4 carboxylic acid derivatives are obtained, following substantially the described procedures.

Examples 77–215 describe the synthesis of compounds $R_1$-$A_1$-S-Z.

EXAMPLE 77

Synthesis of
N-alpha-[3-(N-alpha-benzoyl-tryptophyl)thioacetyl]-L-proline

A solution of 62 mg of N-alpha-benzoyl-tryptophan in 0.5 ml redistilled dimethylformamide (DMF) is cooled in an ice-dry ice-acetone bath at −20° C. To this solution is added a cold solution of 35 mg of 1,1'-carbonyldiimidazole in 1.0 ml of DMF. The solution is stirred at −10° C. for two hours and then added to a cold solution of 48 mg of N-(2-mercaptoacetyl)-L-proline (from Example 29) in 1 ml of DMF which is neutralized with N-ethyl morpholine. The reaction mixture is stirred at −10° C. for an additional hour and then slowly warmed to room temperature. The solvent is removed under reduced pressure at 40° C., and the ethyl acetate is added to the residue. The mixture is cooled in an ice bath and washed with 0.1N HCl and then three times with saturated NaCl solution. The solvent is removed with a rotary evaporator after drying over anhydrous MgSO4. The product is purified by liquid chromatography on Sephadex LH-20 using a 1.2 cm by 95 cm column and eluted with isopropanol. The peak fractions are pooled and the solvent removed under reduced pressure yielding the named product, as a foam-like material.

EXAMPLE 78

Synthesis of
N-alpha-([2-(N-alpha-benzoylglycyl)thioethyl]sulfonyl)-L-proline

A solution of 33 mg of N-alpha-benzoylglycine in 0.5 ml redistilled dimethylformmamide (DMF) is cooled in an ice-dry ice-acetone bath at −20° C. To this solution is added a cold solution of 35 mg of 1,1'-carbonyldiimidazole in 1.0 ml of DMF. The solution is stirred at −10° C. for two hours and then mixed with a cold solution of 48 mg of N-[(2-mercaptoethyl)sulfonyl]-L-proline (from Example 37) in 1 ml of DMF which is neutralized with N-ethyl morpholine. The reaction mixutre is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO4. The product is purified by liquid chromatography on Sephadex LH-20 using a 1.2 cm by 95 cm column and eluted with THF:isopropanol, 3:7 (parts by volume). The peak fractions are pooled and the solvent removed under reduced pressure yielding the named product.

EXAMPLE 79

Synthesis of
N-alpha-[3-(N-alpha-tert-butyloxycarbonyl-phenylalanylthio)-2-trifluoromethylpropanoyl]-L-proline A solution of 133 mg of N-alpha-tert-butyloxycarbonylphenylalanine (N-alpha-Boc-phenylalanine) in 0.5 ml redistilled dimethylformamide (DMF) is cooled in an ice-dry ice-acetone bath at −20° C. To this solution is added a cold solution of 87 mg of 1,1'-carbonyldiimidazole in 1.0 ml of DMF. The solution is stirred at −10° C. for two hours and then mixed with a cold solution of 119.5 mg of N-(3-mercapto-2-trifluoromethyl) propanoyl-L-proline (from Example 39) in 1 ml of DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO4. The product is purified by liquid chromatography on Sephadex G-10 using a 1:2 cm by 95 cm column and eluted with THF:isopropanol, 3:7 (parts by volume). The peak fractions are pooled and the solvent removed under reduced pressure yielding the named product.

EXAMPLE 80

Synthesis of
N-alpha-(3-phenylalanylthio-2-trifluoromethyl-propanoyl)-L-proline

The product from Example 79 is deprotected by stirring a mixture of 30 mg of the product, 50 ul of anisole and 200 ul of anhydrous trifluoroacetic acid (TFA) at room temperature for one hour. Anisole and TFA are removed under reduced pressure at 35° C. and the residue is triturated with anhydrous ether. The white residue is purified by liquid chromatography on Sephadex G-10 using a 1.2 cm by 95 cm column and eluted with 5% acetic acid. The peak fractions are pooled and freezedried yielding the named compound.

EXAMPLE 81

Synthesis of
N-alpha-([3-(N-alpha-acetyl-tyrosylthio)-1-oxopropyl]amino)-L-proline A solution of 41.5 mg of N-alpha-acetyl-tyrosine in 0.5 ml redistilled dimethylformamide (DMF) is cooled in a ice-dry ice-acetone bath at −20° C. To this solution is added a cold solution of 35 mg of 1,1'-carbonyldiimidazole in 1.0 ml of DMF. The solution is stirred at −10° C. for two hours and then is added to a cold solution of 48 mg of N-[(3-mercapto1-oxopropyl)amino]-L-proline (from Example 42) in 1 ml of DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCL and then three times with saturated NaCl solution. The organic solvent is removed with a rotary evaporator after drying over anhydrous MgSO$_4$. The product is purified by Sephadex LH-20 column chromatography using a 1.2 cm by 95 cm column and eluted with isopropanol. The peak fractions are pooled and the solvent is removed under reduced pressure yielding the named product.

EXAMPLE 82

Synthesis of N-alpha-[3-(N-alpha-cyclopentanecarbonylthio)-2-ethylpropanoyl]-L-3,4,-dehydroproline A solution of 52.5 mg of N-alpha-cyclopentanecarbonylisoleucine in 0.5 ml redistilled dimethylformamide (DMF) is cooled in an ice-dry ice-acetone bath at −20° C. To this solution is added a cold solution of 34 mg of 1,1'-carbonyldiimidazole in 1.0 ml of DMF. The solution is stirred at −10° C. for two hours and then mixed with a cold solution of 45.6 mg of N-(2-ethyl-3-mercaptopropanoyl)-L-3,4-dehydroproline (from Example 44) in 1 ml of DMF which is neutralized with N-ethyl morpholine. The reaction mixutre is stirred at −10 C. for an additional hour and then slowly warmed to room temperature. The solvent is removed under reduced pressure at 40° C. and ethyl acetate is added to the residue. The mixture is cooled and washed with 0.1N HCl and then three times with saturated NaCl solution. The solvent is removed with a rotary evaporator after drying over anhydrous MgSO$_4$. The product is purified by LH-20 column chromatography using a 1.2 cm by 95 cm column and eluted with isopropanol. The peak fractions are pooled and the solvent is removed under reduced pressure yielding the named product.

EXAMPLE 83

Synthesis of ([3-(N-alpha-cyclopentanecarbonyl-N-epsilon-tert-butyloxycarbonyl-L-lysyl-histidyl)thiopropanoyl]amino-2-methyl-propanoic acid A solution of 73.5 mg of N-alpha-cyclopentanecarbonyl-N-epsilon-tert-butyloxycarbonyl-L-lysyl-histidine in 0.5 ml redistilled dimethylformamide (DMF) is cooled in an ice-dry, ice-acetone bath at −20° C. To this solution is added a cold solution of 26 mg of 1,1'-carbonyldiimidazole in 1.0 ml of DMF. The solution is stirred at −10° C. for two hours and then mixed with a cold solution of 36 mg of 2-[(3-mercaptopropanoyl)amino]-2-methylpropanoic acid (from Example 46) in 1 ml of DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice water bath and washed with 1N citric acid and then three times with saturated NaCl solution. The solvent is removed with a rotary evaporator after drying over anhydrous MgSO$_4$. The product is purified by LH-20 column chromatography using a 1.2 cm by 95 cm column and eluted with THF:isopropanol, 3:7 (parts by volume). The peak fractions are pooled and the solvent is removed under reduced pressure yielding the named product.

EXAMPLE 84

Synthesis of ([3-(N-alpha-cyclopentanecarbonyl-L-lysylhistidyl)thiopropanoyl]amino)-2-methylpropanoic acid The N-epsilon-Boc group is removed from the lysine by stirring a mixture of 30 mg of the product from Example 83 with 50 μl anisole and 200 μl of anhydrous trifluoroacetic acid (TFA) at room temperature for one hour. Anisole and TFA are removed under reduced pressure at 35° C. and the residue is triturated with anhydrous ether. The residue is purified by liquid chromatography on Sephadex G-10 using a 1.2 cm by 95 cm column and eluted with 5% acetic acid. The peak fractions are pooled and freeze-dried yielding the named product.

EXAMPLE 85

Preparation of N-alpha-[3-(Pyro-L-glutamyl-valyl)thiopropanoyl]-L-alanine

A solution of 87 mg of 1,1'-carbonyldiimidazole in 1.0 ml DMF is added to a solution of 139 mg of pyro-L-glutamylvaline in 0.5 ml DMF at −15° C. The reaction mixture is stirred at −10° C. for 1 hour, and then a mixture of 119.5 mg of N-(3-mercaptopropanoyl)-L-alanine (from Example 50 to 0.072 ml of N-ethyl morpholine in 1 ml DMF is added. The reaction mixture is stirred at −10° C. for an additional hour and then is slowly warmed to room temperature. DMF is removed under reduced pressure with a rotary evaporator at 40° C. and then 7 ml ethyl acetate and 2 ml 1N citric acid are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2×99 cm) partition column chromatography with n-butanol:acetic acid:H$_2$O (4:1:5 by volume) yielding the named product.

EXAMPLE 86

Preparation of N-alpha-([2-(L-lysyl-leucyl)thiomethyl]-5-aminopentanoyl)-L-proline A solution of 87 mg of 1,1'-carbonyldiimidazole in 1.0 ml DMF is added to a solution of 139 mg of bis-Boc-L-lysylleucine in 0.5 ml DMF at −15° C. The reaction mixture is stirred at −10° C. for 1 hour, and then a mixture of 119.5 mg of N-(5-amino-2-mercaptomethylpentanoyl)-L-proline (from Example 55 and 0.072 ml of N-ethyl morpholine in 1 ml. DMF is added. The reaction mixture is stirred at −10° C. for an additional hour and then is slowly warmed to room temperature. DMF is removed under reduced pressure with a rotary evaporator at 40° C. and then 7 ml ehtyl acetate and 2 ml 1N citric acid are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2×99 cm) partition column chromatography with n-butanol:acetic acid:H$_2$O (4:1:5 by volume). The bis-Boc protecting group is removed by treatment with trifluoroacetic acid in anisole as substantially described in Example 78 to yield the named product.

EXAMPLE 87

Preparation of
N-alpha-[(3-[L-arginyl-alanyl]thio)-2-(methylthiomethyl)propanoyl]-L-proline A solution of 87 mg of 1,1'-carbonyldiimidazole in 1.0 ml DMF is added to a solution of 139 mg of tri-Adoc-L-arginylalanine in 0.5 ml DMF at −15° C. The reaction mixture is stirred at −10° C. for 1 hour, and then a mixture of 119.5 mg of N-[3-mercapto-2-(methylthiomethylpropanoyl]-L-proline (from Example 58 and 0.072 ml of N-ethyl morpholine in 1 ml. DMF is added. The reaction mixture is stirred at −10° C. for an additional hour and then is slowly warmed to room temperature. DMF is removed under reduced pressure with a rotary evaporator at 40° C. and then 7 ml ethyl acetate and 2 ml 1N citric acid are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2×99 cm) partition column chromatography with n-butanol:acetic acid:H$_2$O (4:1:5 by volume). The tri-Adoc protecting group is removed by treatment with trifluoroacetic acid in anisole as substantially described in Example 78 to yield the named product.

EXAMPLE 88

Synthesis of
N-alpha-[3-[N-alpha-pyro-L-glutamyl-L-lysyl-phenylalanyl]-thio)-2-(methoxycarbonylmethyl)-propanoyl]-L-proline.

A solution of 73.5 mg of N-alpha-pyro-L-glutamyl-N-epsilon-tert-butyloxycarbonyl-L-lysyl-phenylalanine in 0.5 ml redistilled dimethylformamide (DMF) is cooled in an ice-dry ice-acetone bath at −20° C. To this solution is added a cold solution of 26 mg of 1,1'carbonyldiimidazole in 1.0 ml of DMF. The solution is stirred at −10° C. for two hours and then mixed with a cold solution of 36 mg of N-[3-mercapto-2-(methoxycarbonylmethyl)propanoyl]-L-proline (from Example 62) in 1 ml of DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice water bath and washed with 1N citric acid and then three times with saturated NaCl solution. The solvent is removed with a rotary evaporator after drying over anhydrous MgSO$_4$. The product is purified by LH-20 column chromatography using a 1.2 cm by 95 cm column and eluted with THF:isopropanol, 3:7 (parts by volume). The peak fractions are pooled and the solvent is removed under reduced pressure yielding the product N-alpha-[(3-[N-alpha-pyro-L-glutamyl-N-epsilon-tertbutyloxycarbonyl-L-lysyl-phenylalanyl]-thio-2-(methoxycarbonylmethyl)propanoyl]-L-proline. The tert-butyloxycarbonyl protecting group is removed as described in Example 82 to yield the named product.

EXAMPLE 89

By substituting the appropriate starting materials from Examples 1–76 using appropriate blocking groups where necessary into Examples 77–88 and substantially following the procedures of Examples 77–88, the following thioester compounds, R$_1$-A$_1$-S-Z, as defined in the following table are obtained.

TABLE 11

| R$_1$ | A$_1$ | Z |
|---|---|---|
| H | Phe | Ex. 32 |
| formyl | Ala | Ex. 33 |
| L-arginyl | His | Ex. 35 |
| pyro-L-glutamyl | Leu | Ex. 36 (2) |
| propanoyl | Phe | Ex. 36 (8) |
| cyclopentanecarbonyl | Tyr | Ex. 36 (15) |
| formyl | Phe | Ex. 36 (21) |
| L-lysyl | Gly | Ex. 36 (29) |
| butanoyl | Trp | Ex. 38 (1) |
| phenylacetyl | Phe | Ex. 38 (5) |
| L-lysyl | Phe | Ex. 38 (9) |
| acetyl | Val | Ex. 40 |
| pyro-L-glutamyl-L-lysyl | Ile | Ex. 41 (4) |
| acetyl | His | Ex. 41 (10) |
| t-butyloxycarbonyl | Phe | Ex. 41 (14) |
| benzoyl | Phe | Ex. 43 (1) |
| phenylpropanoyl | Gly | Ex. 43 (6) |
| cyclopentanecarbonyl-L-lysyl | Val | Ex. 43 (11) |
| H | His | Ex. 43 (16) |
| benzoyl | Trp | Ex. 43 (19) |
| H | Tyr | Ex. 45 |
| t-butyloxycarbonyl | Phe | Ex. 41 (14) |
| benzoyl | Phe | Ex. 43 (1) |
| phenylpropanoyl | Gly | Ex. 43 (6) |
| cyclopentanecarbonyl-L-lysyl | Val | Ex. 43 (11) |
| H | His | Ex. 43 (16) |
| benzoyl | Trp | Ex. 43 (19) |
| H | Tyr | Ex. 45 |
| t-butyloxycarbonyl | Leu | Ex. 46 (3) |
| L-lysyl | Phe | Ex. 46 (7) |
| pyro-L-glutamyl-L-lysyl | Gly | Ex. 46 (11) |
| t-butyloxycarbonyl | Trp | Ex. 48 |
| benzoyl | Ala | Ex. 49 (2) |
| benzoyl | Phe | Ex. 49 (9) |
| H | Ile | Ex. 49 (10) |
| cyclopentanecarbonyl | His | Ex. 51 |
| pyro-L-glutamyl | Gly | Ex. 52 (1) |
| phenylacetyl | Ala | Ex. 52 (7) |
| benzoyl | Val | Ex. 53 |
| L-arginyl | Trp | Ex. 54 |
| cyclopentanecarbonyl | Phe | Ex. 56 (3) |
| formyl | His | Ex. 56 (11) |
| pyro-L-glutamyl | Tyr | Ex. 56 (15) |
| benzoyl | Ala | Ex. 56 (22) |
| propanoyl | Phe | Ex. 57 |
| L-lysyl | Ile | Ex. 58 |
| butanoyl | Val | Ex. 61 (2) |
| H | Gly | Ex. 61 (8) |
| cyclopentanecarbonyl-L-lysyl | Phe | Ex. 61 (14) |
| phenylpropanoyl | Trp | Ex. 61 (18) |
| L-lysyl | Ile | Ex. 63 |
| cyclopentanecarbonyl | His | Ex. 65 |
| benzoyl | Leu | Ex. 66 (1) |
| H | Ala | Ex. 66 (5) |
| t-butyloxycarbonyl | Phe | Ex. 66 (11) |

EXAMPLE 90

Synthesis of
N-alpha-[3-(N-alpha-benzoyl-prolyl)thio-acetyl]-L-proline

A solution of 15 mmoles of n-alpha-benzoyl-proline in redistilled dimethylformamide (DMF) is cooled in an ice-dry ice-acetone bath at −20° C. To this solution is added a cold solution of 15 mmoles of 1,1'-carbonyldiimidazole in DMF. The solution is stirred at −10° C. for two hours and then added to a cold solution of 15 mmoles of N-(2-mercaptoacetyl)-L-proline (from Example 29 in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO$_4$. The product is purified by liquid chromatography on Sephadex LH-20 using a 1.2 cm by 95 cm column and eluted with isopropanol. The peak fractions are pooled and the solvent removed under reduced pressure yielding the named product, as a foam-like material.

EXAMPLE 91

Synthesis of N-alpha-([2-N-alpha-benzoyl-thiazolidine 4-carbonyl thioethyl]-sulfonyl)-L-proline A solution of 10 mmoles of N-alpha-benzoyl-thiazolidine-4-carboxylic acid in redistilled dimethylformamide (DMF) is cooled in an ice-dry ice-acetone bath at −20° C. To this solution is added a cold solution of 10 mmoles of 1,1'-carbonyldiimidazole in DMF. The solution is stirred at −10° C. for two hours and then mixed with a cold solution of 10 mmoles of N-[(2-mercaptoethyl)sulfonyl]-L-proline (from Example 37) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO$_4$. The product is purified by liquid chromatography on Sephadex LH-20 using a 1.2 cm by 95 cm column and eluted with THF:isopropanol, 3:7 (parts by volume). The peak fractions are pooled and the solvent removed under reduced pressure yielding the named product.

EXAMPLE 92

Synthesis of N-alpha-[3-(N-alpha-tert-butyloxycarbonyl-1-amino-1-cyclopropanecarbonylthio)-2-trifluoromethylpropanoyl]-L-proline A solution of 20 mmoles of N-alpha-tert-butyloxycarbonyl-1-amino-1-cyclopropane carboxylic acid (N-alpha-Boc-1-amino-1-cyclopropane carboxylic acid in redistilled dimethylformamide (DMF) is cooled in an ice-dry ice-acetone bath at −20° C. To this solution is added a cold solution of 20 mmoles of 1,1'-carbonyldiimidazole in DMF. The solution is stirred at −10° C. for two hours and then mixed with a cold solution of 20 mmoles of N-(3-mercapto-2-trifluoromethyl)propanoyl-L-proline (from Example 39 in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO$_4$/ The product is purified by liquid chromatography on Sephadex G-10 using a 1.2 cm by 95 cm column and eluted with THF:isopropanol, 3:7 (parts by volume). The peak fractions are pooled and the solvent removed under reduced pressure yielding the named product.

EXAMPLE 93

Synthesis of N-alpha-(3-[1-amino-1-amino-1-cyclopropanecarbonyl]thio-2-trifluoromethylpropanoyl)-L-proline The product from Example 92 is deprotected by stirring a mixture of 30 mg of the product, 50 μl of anisole and 200 μl of anhydrous trifluoroacetic acid (TFA) at room temperature for one hour. Anisole and TFA and removed under reduced pressure at 35° C. and the residue is triturated with anhydrous ether. The residue is purified by liquid chromatography on Sephadex G-10 using a 1.2 cm by 95 cm column and eluted with 5% acetic acid. The peak fractions are pooled and freeze-dried yielding the named compound.

EXAMPLE 94

Synthesis of N-alpha-([3-(N-alpha-acetyl-pyroglutamylthio)-1 oxopropyl]-L-proline A solution of 5 mmoles of N-alpha-acetyl-pyroglutamic acid in redistilled dimethylformamide (DMF) is cooled in an ice-dry ice-acetone bath at −20° C. To this solution is added a cold solution of 5 mmoles of 1,1'-carbonyldiimidazole in DMF. The solution is stirred at −10° C. for two hours and then is added to a cold solution of 5 mmoles of N-[(3-mercapto-1-oxopropyl)amino]-L-proline (from Example 42 in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCL and then three times with saturated NaCl solution. The organic solvent is removed with a rotary evaporator after drying over anhydrous MgSO$_4$/ The product is purified by Sephadex LH-20 column chromatography using a 1.2 cm by 95 cm column and eluted with isopropanol. The peak fractions are pooled and the solvent is removed under reduced pressure yielding the named product.

EXAMPLE 95

Synthesis of N-alpha-[3-(N-alpha-cyclopentanecarbonyl-3-hydroxyprolyl-thio)-2-ethylpropanoyl]-L-3,4-dehyroproline A solution of 25 mmoles of N-alpha-cyclopentanecarbonyl-3-hydroxy-proline in redistilled dimethylformamide (DMF) is cooled in an ice-dry ice-acetone bath at −20° C. To this solution is added a cold solution of 25 mmoles of 1,1'-carbonyldiimidazole in DMF. The solution is stirred at −10° C. for two hours and then mixed with a cold solution of 25 mmoles of N-(2-ethyl-3-mercaptopropanoyl)-L-3,4-dehydroproline (from Example 44) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled and washed with 0.1N HCl and then three times with saturated NaCl solution. The solvent is removed with a rotary evaporator after drying over anhydrous MgSO$_4$. The product is purified by LH-20 column chromatography using a 1.2 cm by 95 cm column and eluted with isopropanol. The peak frac-

EXAMPLE 96

Synthesis of
[3-(N-alpha-cyclopentanecarbonyl-N-epsilon-butyloxycarbonyl-L-lysyl-4-bromo-prolyl)thiopropanoyl-]amino)-2-methyl-propanoic acid A solution of 10 mmoles of N-alpha-cyclopentanecarbonyl-N-epsilon-tert-butyloxycarbonyl-L-lysyl-4-bromo-proline in redistilled dimethylformamide (DMF) is cooled in an ice-dry ice-acetone bath at −20° C. To this solution is added a cold solution of 10 mmoles of 1,1'-carbonyldiimidazole in DMF. The solution is stirred at −10° C. for two hours and then mixed with a cold solution of 10 mmoles of 2-[(3-mercaptopropanoyl-)amino]-2-methylpropanoic acid (from Example 47) in DMF which is neutralized with N-ethyl morpholine. The reaction mixture is stirred at −10° C. for an additional hour and then slowly warmed to room temperature. The solvent is removed under reduced pressure at −4° C. and ethyl acetate is added to the residue. The mixture is cooled in an ice water bath and washed with 1N citric acid and then three times with saturated NaCl solution. The solvent is removed with a rotary evaporator after drying over anhydrous MgSO$_4$. The product is purified by LH-20 column chromatography using a 1.2 cm by 95 cm column and eluted with THF:isopropanol, 3:7 (parts by volume). The peak fractions are pooled and the solvent is removed under reduced pressure yielding the named product.

EXAMPLE 97

Synthesis of
([3-N-alpha-cyclopentanecarbonyl-L-lysyl-4-bromo-prolyl)thiopropanoyl]amino)-2-methylpropanoic acid The N-epsilon-Boc group is removed from the lysine by stirring a mixture of 30 mg of the product from Example 96 with 50 μl anisole and 200 μl of anhydrous trifluoroacetic acid (TFA) at room temperature for one hour. Anisole and TFA are removed under reduced pressure at 35° C. and the residue is triturated with anhydrous ether. The residue is purified by liquid chromatography on Sephadex G-10 using a 1.2 cm by 95 cm column and eluted with 5% acetic acid. The peak fractions are pooled and freeze-dried yielding the named product.

EXAMPLE 98

Preparation of
N-alpha-[Pyro-L-glutamyl-3,4-dehydroproly)thiopropanoyl]-L-alanine A solution of 5 mmoles of 1,1'-carbonyldiimidazole in DMF is added to a solution of 5 mmoles of pyro-L-glutamyl-3,4-dehydroproline in DMF at −15° C. The reaction mixture is stirred at −10° C. for 1 hour, and then a mixture of 5 mmoles of N-(3-mercaptopropanoyl)-L-alanine (from Example 50), neutralized with N-ethyl morpholine in DMF, is added. The reaction mixture is stirred at −10° C. for an additional hour and then is slowly warmed to room temperature. DMF is removed under reduced pressure with a rotary evaporator at 4-° C. and then ethyl acetate:1N citric acid (7:2) are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2×99 cm) partition column chromatography with n-butanol:acetic acid:H$_2$O (4:1:5 by volume) yielding the named product.

EXAMPLE 99

Preparation of
N-alpha-([2-(L-lysyl-3,4-dichloroprolyl)thiomethyl]-5-aminopentanoyl)-L-proline A solution of 5 mmoles of 1,1'-carbonyldiimidazole in DMF is added to a solution of mmoles of bis-Boc-L-lysyl-3,4-dichloroproline in DMF at −15° C. The reaction mixture is stirred at −10° C. for 1 hour, and then a mixture of 5 mmoles of N-(5-N-Boc-amino-2-mercaptomethylpentanoyl)-L-proline (from Example 55), neutralized with N-ethyl morpholine in DMF, is added. The reaction mixture is stirred at −10° C. for an additional hour and then is slowly warmed to room temperature. DMF is removed under reduced pressure with a rotary evaporator at 40° C. and then ethyl acetate:1N citric acid (7:2) are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2×99 cm) partition column chromatography with n-butanol:acetic acid:H$_2$O (4:1:5 by volume). The Boc protecting groups are removed by treatment with trifluoroacetic acid in anisole as substantially described in Example 93 to yield the named product.

EXAMPLE 100

Preparation of
N-alpha-[(3-[L-arginyl-prolyl]thio)-2-(methylthiomethyl)propanoyl]-L-proline A solution of 10 mmoles of 1,1'-carbonyldiimidazole in DMF is added to a solution of 10 mmoles of tri-Adoc-L-arginylproline in DMF at −15° C. The reaction mixture is stirred at −10° C. for 1 hour, and then a mixture of 10 mmoles of N-[3-mercapto-2-(methylthiomethyl)propanoyl]-L-proline (from Example 58), neutralized with N-ethyl morpholine in DMF, is added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2×99 cm) partition column chromatography with n-butanol:acetic acid:H$_2$O (4:1:5 by volume). The tri-Adoc protecting group is removed by treatment with trifluoroacetic acid in anisole as substantially described in Example 93 to yield the named product.

EXAMPLE 101

Synthesis of
N-alpha-[(3-[N-alpha-pyro-L-glutamyl-L-lysyl-4-hydroxy-prolyl]-thio)-2-(methoxycarbonylmethyl)-propanoyl]-L-proline A solution of 5 mmoles of N-alpha-phro-L-glutamyl-N-epsilon-tert-butyloxycarbonyl-L-lysyl-4-hydroxy-proline in redistilled dimethylformamide (DMF) is cooled in an ice-dry ice-acetone bath at −20° C. To this solution is added a cold solution of 5 mmoles of 1,1'-carbonyldiimidazole in DMF. The solution is stirred at −10° C. for two hours and then mixed with a cold solution of 5 mmoles of N-[(3-mercapto-2-methoxycarbonylmethyl)propanoyl]-L-proline (from Example 62 in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice water bath and washed with 1N citric acid and then three times with saturated NaCl solution. The solvent is removed with a rotary evaporator after drying over anhydrous MgSO$_4$. The product is purified by LH-20 column chromatography using a 1.2 cm by 95 cm column and eluted with THF:isopropanol, 3:7 (Parts by volume). The peak fractions are pooled and the solvent is removed under the reduced pressure yielding the product N-alpha-[(3-[N-alpha-pyro-L-glutamyl-N-epsilon-tertbutyloxycarbonyl-L-lysyl-phenylalanyl]-thio-2-(methoxycarbonylmethyl)-propanoyl]-L-proline. The tert-butyloxycarbonyl protecting group is removed as described in Example 97 to yield the named product.

EXAMPLE 102

By substituting the appropriate starting materials from Examples 1-66 using appropriate blocking groups where necessary into Examples 90-101 and substantially following the procedures of Examples 90-100, the following thioester compounds, $R_1$-$A_1$-S-Z, as defined in the following table are obtained.

TABLE 11

| $R_1$ | $A_1$ | Z |
|---|---|---|
| propanoyl | 3-hydroxyproline | Ex. 33 |
| pyro-L-glutamyl | cycloleucine | Ex. 36 (3) |
| H | 3,4-dehydroproline | Ex. 38 (7) |
| benzoyl | 1-amino-1-cyclohexane | Ex. 41 (2) |
| t-butyloxy carbonyl | 4-fluoroproline | Ex. 41 (13) |
| L-lysyl | proline | Ex. 43 (4) |
| cyclotentane carbonyl | 3,4-dibromoproline | Ex. 43 (18) |
| acety | cycloleucine | Ex. 46 (2) |
| benzoyl | alpha-methyl proline | Ex. 46 (6) |
| L-arginyl | thiazolidine-r-carboxylic acid | Ex. 49 (8) |
| cyclopentane carbonyl-L-lysyl | 3,4-dehydroproline | Ex. 52 (6) |
| formyl | pyroglutamic acid | Ex. 54 |
| benzoyl | 3-chloro-4-iodo proline | Ex 56 (6) |
| H | 1-amino-1-cyclobutane | Ex. 56 (17) |
| phenyl acetyl | 4-hydroxyproline | Ex. 61 (3) |
| t-butyloxycarbonyl | proline | Ex. 61 (17) |
| pyro-L-glutamyl-L-lysyl | pyroglutamic acid | Ex. 66 (3) |
| benzoyl | 1-amino-1-cyclopropane carboxylic acid | Ex. 66 (10) |

EXAMPLE 103

Synthesis of N-alpha-[3-(N-alpha-benzoyl-5-methyl-tryptophy)thioacetyl]-L-proline A solution of 10 mmoles of N-alpha-benzoyl-5-methyl-tryptophan in redistilled dimethylformamide (DMF) is cooled in an ice-dry ice-acetone bath at −20° C. To this solution is added a cold solution of 10 mmoles of 1,1′-carbonyldiimidazole in DMF. The solution is stirred at −10° C. for two hours and then added to a cold solution of 10 mmoles of N-(2-mercaptoacetyl)-L-proline (from Example 29) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO$_4$. The product is purified by liquid chromatography on SEphadex LH-20 using a 1.2 cm by 95 cm column and eluted with isopropanol. The peak fractions are pooled and the solvent removed under reduced pressure yielding the named product, as a foam-like material.

EXAMPLE 104

Synthesis of N-alpha-([2-(N-alpha-benzoyl-phenyglycyl)thioethyl]-sulfonyl)-L-proline A solution of 5 mmoles of N-alpha-benzoyl-phenylglycine in redistilled dimethylformamide (DMF) is cooled in an ice-dry ice-acetone bath at −20° C. To this solution is added a cold solution of 5 mmoles of 1,1′-carbonyldiimidazole in DMF. The solution is stirred at −10° C. for two hours and then mixed with a cold solution of 5 mmoles of N-[(2-mercaptoethyl)sulfonyl]-L-proline (from Example 37 in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with sturated NaCl solution. The solvent is removed with a rotary evaporator after drying over anhydrous MgSO$_4$/ The product is purified by liquid chromatography on Sephadex LH-20 using a 1.2 cm by 95 cm column and eluted with THF:isopropanol, 3:7 (parts by volume). The peak fractions are pooled and the solvent removed under reduced pressure yielding the named product.

EXAMPLE 105

Synthesis of N-alpha-[3-(N-alpha-tert-butyloxycarbonyl-4-nitrophenylalanylthio)-2-trifluoromethylpropanoyl]-L-proline A solution of 15 mmoles of N-alpha-tert-butyloxycarbonyl-4-nitrophenylalanine (N-alpha-Boc-4-nitrophenylalanine in redistilled dimethylformamide (DMF) is cooled in an ice-dry ice-acetone bath at −20° C. To this solution is added a cold solution of 15 mmoles of 1,1′-carbonyldiimidazole in DMF. The solution is stirred at −10° C. for two hours and then mixed with a cold solution of 15 mmoles of N-(3-mercapto-2-trifluoromethyl)propanoyl-L-proline (from Example 39) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO$_4$. The product is purified by liquid chromatography on Sephadex G-10 using a 1.2 cm by 95 cm column and eluted with THF:isopropanol, 3:7 (parts by volume). The peak fractions are pooled and the solvent removed under reduced pressure yielding the named product.

EXAMPLE 106

Synthesis of N-alpha-(3-[4-nitro-phenylalanyl]thio-2-trifluoromethyl-propanoyl-L-proline The product from Example 105 is deprotected by stirring a mixture of 30 mg of the product, 50 μl of anisole and 200 μl of anhydrous trifluoroacetic acid (TFA) at room temperature for one hour. Anisole and TFA are removed under reduced pressure at 35° C. and the residue is triturated with anhydrous ether. The residue is purified by liquid chromatography on Sephadex G-10 using a 1.2 cm by 95 cm column and eluted with 5% acetic acid. The peak fractions are pooled and freeze-dried yielding the named compound.

EXAMPLE 107

Synthesis of N-alpha-([3-(N-alpha-acetyl-3-chlorotyrosylthio)-1-oxopropyl]amino)-L-proline A solution of 20 mmoles of N-alpha-acetyl-3-chloro-tyrosine in redistilled dimethylformamide (DMF) is cooled in an ice-dry ice-acetone bath at −20° C. To this solution is added a cold solution of 20 mmoles of 1,1'-carbonyldiimidazole in DMF. The solution is stirred at −10° C. for two hours and then is added to a cold solution of 20 mmoles of N-[(3-mercapto-1-oxopropyl)amino]-L-proline (from Example 42) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCL and then three times with saturated NaCl solution. The organic solvent is removed with a rotary evaporator after drying over anhydrous MgSO4. The product is purified by Sephadex LH-20 column chromatography using a 1.2 cm by 95 cm column and eluted with isopropanol. The peak fractions are pooled and the solvent is removed under reduced pressure yielding the named product.

EXAMPLE 108

Syntheis of N-alpha-[3-(N-alpha-cyclopentanecarbonyl-O-benzyl-tyrosylthio)-2-ethylpropanoyl]-L-3,4-dehydroproline A solution of 5 mmoles of N-alpha-cyclopentanecarbonyl-O-benzyl tyrosine in redistilled dimethylformamide (DMF) is cooled in an ice-dry ice-acetone bath at −20° C. To this solution is added a cold solution of 5 mmoles of 1,1'-carbonyldiimidazole in DMF. The solution is stirred at −10° C. for two hours and then mixed with a cold solution of mmoles of N-(2-ethyl-3-mercaptopropanoyl)-L-3,4-dehydroproline (from Example 44) in DMF which is neutralized with N-ethyl morpholine. The reaction mixture is stirred at −10° C. and ethyl acetate is added to the residue. The mixture is cooled and washed with 0.1N HCl and then three times with saturated NaCl solution. The solvent is removed with a rotary evaporator after drying over anhydrous MgSO4. The product is purified by LH-20 column chromatography using a 1.2 cm by 95 cm column and eluted with isopropanol. The peak fractions are pooled and the solvent is removed under reduced pressure yielding the named product.

EXAMPLE 109

Synthesis of [3-(N-alpha-cyclopentanecarbonyl-N-epsilon-tert-butyloxycarbonyl-L-lysyl-Beta-2-thienyl-alanyl)thio-propanoyl]amino)-2-methylpropanoic acid A solution of 10 mmoles of N-alpha-cyclopentanecarbonyl-N-epsilon-tert-butyloxycarbonyl-L-lysyl-beta-2-thienyl-alanine in redistilled dimethylformamide (DMF) is cooled in an ice-dry ice-acetone bath at −20° C. To this solution is added a cold solution of 10 mmoles of 1,1'-carbonyldiimidazole in DMF. The solution is stirred at −10° C. for two hours and then mixed with a cold solution of 10 mmoles of 2-[(3-mercaptopropanoyl)amino]-2-methylpropanoic acid (from Example 47) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice water bath and washed with 1N citric acid and then three times with saturated NaCl solution. The solvent is removed with a rotary evaporator after drying over anhydrous MgSO4. The product is purified by LH-20 column chromatography using a 1.2 cm by 95 cm column and eluted with THF:isopropanol, 3:7 (parts of volume). The peak fractions are pooled and the solvent is removed under reduced pressure yielding the named product.

EXAMPLE 110

Synthesis of ([3-(N-alpha-cyclopentanecarbonyl-L-lysylthio-propanoyl]amino)-2-methylpropanoic acid The N-epsilon-Boc group is removed from the lysine by stirring a mixture of 30 mg of the product for Example 109 with 50 μl anisole and 200 μl of anhydrous trifluoroacetic acid (TFA) at room temperature for one hour. Anisole and TFA are removed under reduced pressure at 35° C. and the residue is triturated with anhydrous ether. The residue is purified by liquid chromatography on Sephadex G-10 using a 1.2 cm by 95 cm column and eluted with 5% acetic acid. The peak fractions are pooled and freez-dried yielding the named product.

EXAMPLE 111

Preparation of N-alpha-[3-(Pyro-L-glutamyl-3,5-dibromotyrosyl)-thio-propanoyl]-L-alanine.

A solution of 5 mmoles of 1,1'-carbonyldiimidazole in DMF is added to a solution of 5 mmoles of pyro-L-glutamyl-3,5-dibromo-tyrosine in DMF at −15° C. The reaction mixture is stirred at −10° C. for 1 hour, and then a mixture of 5 mmoles of N-(3-mercaptopropanoyl)-L-alanine (from Example 50), neutralized with N-ethyl morpholine in DMF, is added. The reaction mixture is stirred at −10° C. for an additional hour and then is slowly warmed to room temperature. DMF is removed under reduced pressure with a rotary evaporator at 40° C. and then ethyl acetate: 1N citric acid (7:2) are added. The organic phase is washed two times with 1N citric acid and two times with saturated NaCl. The organic phase is dried with anhydrous MgSO4 and then filtered. Solvent is removed using a rotary evaporator. The residue is purified on Sephadex G-25 (1.2 cm×99 cm) partition column chromatography with n-butanol:acetic acid:H₂O (4:1:5 by volume) yielding the named product.

EXAMPLE 112

Preparation of
N-alpha-([2-(L-lysyl-6-fluoro-tryptophyl)thiomethyl]-5-aminopentanoyl)-L-proline A solution of 15 mmoles of 1,1'-carbonyldiimidazole in DMF is added to a solution of 15 mmoles of bis-Boc-L-lysyl-6-fluoro-tryptophyl in DMF at $-15°$ C. The reaction mixture is stirred at $-10°$ C. for 1 hour, and then a mixture of 15 mmoles of N-(5-Boc-amino-2-mercaptomethylpentanoyl)-L-proline (from Example 55), neutralized with N-ethyl morpholine in DMF, is added. The reaction mixture is stirred at $-10°$ C. for an additional hour and then is slowly warmed to room temperature. DMF is removed under reduced pressure with a rotary evaporator at 40° C. and then ethyl acetate:1N citric acid (7:2) are added. The organic phase is washed two times with 1N citric acid and two times with saturated NaCl. The organic phase is dried with anhydrous MgSO₄ and then filtered. Solvent is removed using a rotary evaporator. The residue is purified on Sephadex G-25 (1.2×99 cm) partitition column chromatography with n-butanol:acetic acid:H₂O (4:1:5 by volume). The Boc protecting groups are removed by treatment with trifluoroacetic acid in anisole as substantially described in Example 106 to yield the named product.

EXAMPLE 113

Preparation of
N-alpha-[(3-[L-arginyl-5-methoxy-tryptophyl]-thio)-2-(methyl-thiomethyl)propanoyl]-L-proline A solution on 10 mmoles of 1,1'-carbonyldiimidazole in DMF is added to a solution of 10 mmoles of tri-Adoc-L-arginyl-5-methoxy-tryptophan in 0.5 ml DMF at $-15°$ C. The reaction mixture is stirred at $-10°$ C. for 1 hour and then a mixture of 10 mmoles of N-[3-mercapto-2-(methylthiomethylpropanoyl]-L-proline (from Example 58), neutralized with N-ethyl morpholine in DMF is added. The reaction mixture is stirred at $-10°$ C. for an additional hour and then is slowly warmed to room temperature. DMF is removed under reduced pressure with a rotary evaporator at 40° C. and then 7 ml ethyl acetate and 2 ml 1N citric acid are added. The organic phase is washed two times with 1N citric acid and two times with saturated NaCl. The organic phase is dried with anhydrous MgSO₄ and then filtered. Solvent is removed using a rotary evaporator. The residue is purified on Sephadex G-25 (1.2 cm×99 cm) partition column chromatography with n-butanol:acetic acid:-H₂O (4:1:5 by volume). The tri-Adoc protecting group is removed by treatment with trifluoroacetic acid in anisole as substantially described in Example 106 to yield the named product.

EXAMPLE 114

Synthesis of
N-alpha-[(3-[N-alpha-pyro-L-glutamyl-L-lysyl-3-5dibromo-tyrosyl]-thio)-2-(methoxycarbonylmethyl)-propanoyl]-L-proline A solution of 5 mmoles of N-alpha-pyro-L-glutamyl-N-epsilon-tert-butyloxycarbonyl-L-lysyl-3,5-dibromo-tyrosine in redistilled dimethylformamide (DMF) is cooled in an ice-dry ice-acetone bath at $-20°$ C. To this solution is added a cold solution of 5 mmoles of 1,1'-carbonyldiimidazole in DMF. The solution is stirred at $-10°$ C. for two hours and then mixed with a cold solution of 5 mmoles of N-[3-mercapto-2-(methoxycarbonylmethyl)propanoyl]-L-proline (from Example 62) in DMF which is neutralized with N-ethyl morpholine. The reaction mixture is stirred at $-10°$ C. for an additional hour and then slowly warmed to room temperature. The solvent is removed under reduced pressure at 40° C. and ethyl acetate is added to the residue. The mixture is cooled in an ice water bath and washed with 1N citric acid and then three times with saturated NaCl solution. The solvent is removed with a rotary evaporator after drying over anhydrous MgSO₄. The product is purified by LH-20 column chromatography using a 1.2 cm×95 cm column and eluted with THF:isopropanol, 3:7 (parts by volume). The peak fractions are pooled and the solvent is removed under reduced pressure yielding the product N-alpha-[(3-[N-alpha-pyro-L-glutamyl-N-epsilon-tertbutyloxycarbonyl-L-lysyl-phenylalanyl]thio)-2-(methoxycarbonylmethyl)-propanoyl]-L-proline. The tert-butyloxycarbonyl protecting group is removed as described in Example 110 to yield the named product.

EXAMPLE 115

By substituting the appropriate starting materials from Example 1-66 using appropriate blocking groups where necessary into Examples 102-114 and substantially following the procedures of Example 102-114, the following thioester compounds, $R_1$-$A_1$-S-Z, as defined in the following table are obtained.

TABLE 11

| R | A | Z |
| --- | --- | --- |
| t-butyloxycarbonyl | 3-hydroxy-tyrosine | Ex. 31 |
| L-lysyl | beta-benzyl aspartic acid | 36 (6) |
| formyl | alpha-methyl phenylalanine | 36 (14) |
| butanoyl | thyronine | 36 (23) |
| H | 1-methyl-tryptophan | 38 (3) |
| benzoyl | 3-fluoro-tyrosine | 38 (10) |
| pyro-L-glutamyl | phenylglycine | 40 |
| cyclopenatene carbonyl-l-lysyl | S—benzylcysteine | 41 (1) |
| phenylpropanoyl | gamma-benzyl glutamate | 41 (12) |
| L-arginyl | 4-amino-phenylalanine | 43 (5) |
| H | alpha-methyl tryptophan | 43 (11) |
| formyl | beta-phenyl serine | 43 (15) |
| cyclopentanecarbonyl | O—benzyl tyrosine | 46 (1) |
| benzoyl | 3-nitro-tyrosine | 46 (5) |
| t-butyloxycarbonyl | 5-fluoro-tryptophan | 46 (11) |
| pyro-L-glutamyl-L-tysyl | 3,5-dichloro-tyrosine | 48 |
| H | O—benzyl threonine | 49 (6) |
| benzoyl | 4-methoxy-phenylalanine | 52 (3) |
| L-lysyl | alpha-methyl histidine | 52 (10) |
| acetyl | 3-chloro-5-bromo-tyrosine | 52 (16) |
| cyclopentanecarbonyl | 4-iodo-phenylalanine | 55 |
| L-lysyl | 3-methoxy-tyrosine | 56 (4) |
| benzoyl | alpha-methyl tyrosine | 56 (11) |
| propanoyl | O—benzyl serine | 56 (16) |
| cyclopentanecarbonyl-L-lysyl | 4-nitro-phenylalanine | 58 |
| H | beta-2-thienyl-serine | 60 (5) |
| benzoyl | 3-methoxy-tryptophan | 66 (6) |
| t-butyloxycarbonyl | beta-2-thienyl-alanine | 66 (13) |

EXAMPLE 116

Synthesis of
N-alpha-[3-(L-alpha-glutamylthio)-2-D-methyl-propanoyl]-L-proline

A solution of 160.2 mg (0.4 mmol) of alpha-N-hydroxysuccinimido-gamma-t-butyl-N-alpha-t-butyloxycarbonly-L-glutamate and 87 mg (0.4 mmol) of D-3-mercapto-2-methyl-propanoyl-L-proline in 1.5 ml of redistilled dioxane was cooled in an ice bath with stirring. N-ethyl-morpholine, 0.055 ml (0.4 mmol) was added. The mixture was stirred for 5 min at 0° C. and then at room temperature for one week. Solvent was removed with a rotary evaporator at 30° C. The residue was dissolved in 4 ml of H₂O plus 1 ml of 1N NaHCO₃. The solution was extracted three times with 1 ml portions of ethyl acetate. To the aqueous phase was added 5 ml of ethyl acetate and the mixture was acidified to pH 2 with concentrated hydrochloric acid. The organic phase was saved, and the aqueous phase was extracted once more with 5 ml of ethyl acetate. The combined organic phase was washed three times with saturated NaCl and then dried over anhydrous MgSO₄. The organic phase was evaporated to dryness with a rotary evaporator to yield an oily residue. To the residue was added 0.1 ml of anisole and 0.4 ml of trifluoroacetic acid. The solution was stirred briefly at 0° C. and then at room temperature for 1 hour. The solvent was removed with a rotary evaporator, under high vacuum, at 30° C. The residue was stored in a vacuum desiccator, over NaOH and P₂O₅, for several hours to remove all traces of solvent. The product was purified by partition chromatography (Sephadex G-25, 1.2×95 cm column; equilibrated with n-butanol/acetic acid/H₂O 4:1:5 by volume). The equilibrated column was developed with the upper phase for the first 26 fractions and then with lower phase. Fractions of 2.05 ml were collected. Fractions 60–64 contained the desired product. Solvent was removed with a rotary evaporator, and the product was obtained by lyophilization from H₂O (29 mg). The product behaved as a pure substance on paper electrophoresis (pH 2 and pH 5) and on three thin layer chromatography systems (silica gel plates).

EXAMPLE 117

Synthesis of N-alpha-([2-N-alpha-benzoyl-cysteinyl)thioethyl]-sulfonyl)-L-proline A solution of 25 mmoles of N-alpha-benzoyl-S-acetyl-cysteine in redistilled dimethylformamide (DMF) is cooled in an ice-dry ice-acetone bath at −20° C. To this solution is added a cold solution of 25 mmoles of 1,1′-carbonyldiimidazole in DMF. The solution is stirred at −10° C. for two hours and then mixed with a cold solution of 25 mmoles of N-[(2-mercaptoethyl)-sulfonyl]-L-proline (from Example 37) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO₄. The product is purified by liquid chromatography on Sephadex LH-20, using a 1.2 cm×95 cm column and eluted with THF:isopropanol, 3:7 (parts by volume). The peak fractions are pooled and the solvent removed under reduced pressure. The acetyl protecting group is removed by following the procedure described in Example 53, step (c).

EXAMPLE 118

Synthesis of N-alpha-[3-(N-alpha-tert-butyloxycarbonylnorleucylthio)-2-trifluoromethylpropanoyl]-L-proline A solution of 10 mmoles of N-alpha-tert-butyloxycarbonylnorleucine (N-Boc-norleucine) in redistilled dimethylformamide (DMF) is cooled in an ice-dry ice-acetone bath at −20° C. To this solution is added a cold solution of 10 mmoles of 1,1′-carbonyldiimidazole in DMF. The solution is stirred at −10° C. for two hours and then mixed with a cold solution of 10 mmoles of N-(3-mercapto-2-trifluoromethyl)propanoyl-L-proline (from Example 39) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The solvent is removed with a rotary evaporator after drying over anhydrous MgSO₄. The product is purified by liquid chromatography on Sephadex G-10 using a 1.2 cm×95 cm column and eluted with THF:isopropanol, 3:7 (parts by volume). The peak fractions are pooled and the solvent removed under reduced pressure yielding the named product.

EXAMPLE 119

Synthesis of N-alpha-(3-norleucylthio-2-trifluoromethylpropanoyl)-L-proline

The product from Example 118 is deprotected by stirring a mixture of 30 mg of the product, 50 ul of anisole and 200 ul of anhydrous trifluoroacetic acid (TFA) at room temperature for one hour. Anisole and TFA are removed under reduced pressure at 35° C. and the residue is triturated with anhydrous ether. The residue is purified by liquid chromatography on Sephadex G-10 using a 1.2 cm×95 cm column and eluted with 5% acetic acid. The peak fractions are pooled and freeze-dried yielding the named compound.

EXAMPLE 120

Synthesis of N-alpha-([3-N-alpha-acetyl-methionylthio)-1-oxopropyl]amino)-L-proline A solution of 10 mmoles of N-alpha-acetyl-methionine in redistilled dimethylformamide (DMF) is cooled in an ice-dry ice-acetone bath at −20° C. To this solution is added a cold solution of 10 mmoles of 1,1′-carbonyldiimidazole in DMF. The solution is stirred at −10° C. for two hours and then is added to a cold solution of 10 mmoles of N-[(3-mercapto-1-oxopropyl)amino]-L-proline (from Example 42) in DMF which is neutralized with N-ethyl morpholine. The reaction mixture is stirred at −10° C. for an additional hour and then slowly warmed to room temperature. The solvent is removed under reduced pressure at 40° C. and ethyl acetate is added to the residue. The mixture is cooled in an ice bath and washed with 0.1N HCl and then three times with saturated NaCl solution. The organic solvent is removed with a rotary evaporator after drying over anhydrous MgSO₄. The product is purified by Sephadex LH-20 column chromatography using a 1.2 cm×95 cm column and eluted with isopropanol. The peak fractions are pooled and the solvent is removed under reduced pressure yielding the named product.

EXAMPLE 121

Synthesis of
N-alpha-[3-(N-alpha-cyclopentanecarbonyl-serylthio)-2-ethylpropanoyl]-L-3,4-dehydroproline A solution of 5 mmoles of N-alpha-cyclopentanecarbonyl-O-acetyl-serine in redistilled dimethylformamide (DMF) is cooled in an ice-dry ice-acetone bath at $-20°$ C. To this solution is added a cold solution of 5 mmoles of 1,1'-carbonyl-diimidazole in DMF. The solution is stirred at $-10°$ C. for two hours and then mixed with a cold solution of 5 mmoles of N-(2-ethyl-3-mercaptopropanoyl)-L-3,4-dehydroproline (from Example 44) in DMF which is neutralized with N-ethyl morpholine. The reaction mixture is stirred at $-10°$ C. for an additional hour and then slowly warmed to room temperature. The solvent is removed under reduced pressure at 40° C. and ethyl acetate is added to the residue. The mixture is cooled and washed with 0.1N HCl and then three times with saturated NaCl solution. The solvent is removed with a rotary evaporator after drying over anhydrous MgSO$_4$. The product is purified by LH-20 column chromatography using a 1.2 cm×95 cm column and eluted with isopropanol. The peak fractions are pooled and the solvent is removed under reduced pressure. The acetyl protecting group is removed by treatment with anhydrous HF in the presence of anisole.

EXAMPLE 122

Synthesis of
([3-(N-alpha-cyclopentanecarbonyl-N-epsilon-tert-butyloxycarbonyl-L-lysyl-norvalyl)thiopropanoyl]amino)-2-methyl-propanoic acid A solution of 10 mmoles of N-alpha-(N-alpha-cyclopentanecarbonyl-N-epsilon-tert-butyloxycarbonyl-L-lysyl-norvaline in redistilled dimethylformamide (DMF) is cooled in an ice-dry ice-acetone bath at $-20°$ C. To this solution is added a cold solution of 10 mmoles of 1,1'-carbonyldiimidazole in DMF. The solution is stirred at $-10°$ C. for two hours and then mixed with a cold solution of 10 mmoles of 2-[(3-mercaptopropanoyl)amino]-2-methylpropionic acid (from Example 47) in DMF which is neutralized with N-ethyl morpholine. The reaction mixture is stirred at $-10°$ C. for an additional hour and then slowly warmed to room temperature. The solvent is removed under reduced pressure at 40° C. and ethyl acetate is added to the residue. The mixture is cooled in an ice water bath and washed with 1N citric acid and then three times with saturated NaCl solution. The solvent is removed with a rotary evaporator after drying over anhydrous MgSO$_4$. The product is purified by LH-20 column chromatography using a 1.2 cm×95 cm column and eluted with THF:isopropanol, 3:7 (parts by volume). The peak fractions are pooled and the solvent is removed under reduced pressure yielding the named product.

EXAMPLE 123

Synthesis of
([3-N-alpha-cyclopentanecarbonyl-L-lysyl-norvalyl)-thiopropanoyl]amino)-2-methylpropanoic acid The N-epsilon-Boc group is removed from the lysine by stirring a mixture of 30 mg of the product from Example 122 with 50 ul anisole and 200 ul of anhydrous trifluoroacetic acid (TFA) at room temperature for one hour. Anisole and TFA are removed under reduced pressure at 35° C. and the residue is triturated with anhydrous ether. The residue is purified by liquid chromatography on Sephadex G-10 using a 1.2 cm×95 cm column and eluted with 5% acetic acid. The peak fractions are pooled and freeze-dried yielding the named product.

EXAMPLE 124

Synthesis of
N-alpha-[3-(N-alpha-pyro-L-glutamyl-lysyl)thiopropanoyl]-L-alanine

A solution of 20 mmoles of 1,1'-carbonyldiimidazole in DMF is added to a solution of 20 mmoles of N-alpha-pyro-L-glutamyl-N-epsilon-Boc-lysine in DMF at $-15°$ C. The reaction mixture is stirred at $-10°$ C. for one hour, and then a mixture of 20 mmoles of N-(3-mercaptopropanoyl)-L-alanine (from Example 50), neutralized with N-ethyl morpholine in DMF, is added. The reaction mixture is stirred at $-10°$ C. for an additional hour and then is slowly warmed to room temperature. DMF is removed under reduced pressure with a rotary evaporator at 40° C. and then ethyl acetate:1N citric acid (7:2) are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2×99 cm) partition column chromatography with n-butanol:acetic acid:H$_2$O (4:1:5) by volume). The N-epsilon-Boc group is removed from the lysine as described in Example 123.

EXAMPLE 125

Synthesis of
N-alpha-([2-(L-lysyl-S-ethyl-cysteinyl)thiomethyl]-5-aminopentanoyl)-L-proline A solution of 5 mmoles of 1,1'-carbonyldiimidazole in DMF is added to a solution of 5 mmoles of bis-Boc-L-lysyl-S-ethyl-cysteine in DMF at $-15°$ C. The reaction mixture is stirred at $-10°$ C. for one hour, and then a mixture of 5 mmoles of N-alpha-(5-N-Boc-amino-2-mercaptomethylpentanoyl)-L-proline (prepared from Example 55), neutralized with N-ethyl morpholine in DMF, is added. The reaction mixture is stirred at $-10°$ C. for an additional hour and then is slowly warmed to room temperature. DMF is removed under reduced pressure with a rotary evaporator at 40° C. and then ethyl acetate:1N citric acid (7:2) are added. The organic phase is washed two times with 1N citric acid and two times with saturated NaCl. The organic phase is dried with anhydrous MgSO$_4$ and then filtered. Solvent is removed using a rotary evaporator. The residue is purified on Sephadex G-25 (1.2×99 cm) partition column chromatography with n-butanol:acetic acid:H$_2$O (4:1:5 by volume). The Boc protecting groups are removed by treatment with trifluoroacetic acid in anisole as substantially described in Example 119 to yield the named product.

EXAMPLE 126

Synthesis of
N-alpha-[(3-[L-arginyl-O-phopho-treonyl]thio)-2-(methylthiomethyl)propanoyl]-L-proline A solution of 15 mmoles of 1,1'-carbonyldiimidazole in DMF is added to a solution of 15 mmoles of tri-Adoc- L-arginyl-O-phospho-threonine in DMF at −15° C. The reaction mixture is stirred at −10° C. for one hour, and then a mixture of 15 mmoles of N-[3-mercapto-2-(methylthiomethylpropanoyl]-L-proline (from Example 58) neutralized with N-ethyl morpholine in DMF, is added. The reaction mixture is stirred at −10° C. for an additional hour and then is slowly warmed to room temperature. DMF is removed under reduced pressure with a rotary evaporator at 401 C. and then ethyl acetate:1N citric acid (7:2) are added. The organic phase is washed two times with 1N citric acid and two times with saturated NaCl. The organic phase is dried with anhydrous MgSO4 and then filtered. Solvent is removed using a rotary evaporator. The residue is purified on Sephadex G-25 (1.2×99 cm) partition column chromatography with n-butanol:acetic acid:H2O (4:1:5 by volume). The tri-Adoc protecting group is removed by treatment with trifluoroacetic acid in anisole as substantially described in Example 119 to yield the named product.

EXAMPLE 127

Synthesis of N-alpha-[(3-[N-alpha-pyro-L-glutamyl-L-lysyl-beta-alanyl]-thio)-2-(methoxycarbonylmethyl)propanoyl]-L-proline A solution of 10 mmoles of N-alpha-pyro-L-glutamyl-N-epsilon-tert-butyloxycarbonyl-L-lysyl-beta-alanine in redistilled dimethylformamide (DMF) is cooled in an ice-dry ice-acetone bath at −20° C. To this solution is added a cold solution of 10 mmoles of 1,1'-carbonyldiimidazole in DMF. the solution is stirred at −10° C. for two hours and then mixed with a cold solution of 10 mmoles of N-[3-mercapto-2-(methoxycarbonylmethyl)propanoyl]-L-proline (from Example 62) in DMF which is neutralized with N-ethyl morpholine. The reaction mixture is stirred at −10° C. for an additional hour and then slowly warmed to room temperature. The solvent is removed under reduced pressure to 40° C. and ethyl acetate is added to the residue. The mixture is cooled in an ice water bath and washed with 1N citric acid and then three times with saturated NaCl solution. The solvent is removed with a rotary evaporator after drying over anhydrous MgSO4. The product is purified by LH-20 column chromatography using a 1.2 cm×95 cm column and eluted with THF:isopropanol, 3:7 (parts by volume). The peak fractions are pooled and the solvent is removed under reduced pressure yielding the product N-alpha-[(3-[N-alpha-pyro-L-glutamyl-N-epsilon-tert-butyloxycarbonyl-L-lysyl-beta-alanine]-thio-2-(methoxycarbonylmethyl)-propanoyl]-L-proline. The tert-butyloxycarbonyl protecting group is removed as described in Example 123 to yield the named product.

EXAMPLE 128

By substituting the appropriate starting materials from Examples 1-66 using appropriate blocking groups where necessary into Examples 116-127 and substantially following the procedures of Examples 116-127, the following thioester compounds, $R_1$-$A_1$-S-Z, as defined in the following table, are obtained.

TABLE 12

| R | A | Z Ex. |
|---|---|---|
| H | alpha-amino-butyric acid | 32 |
| benzoyl | homoserine | 35 |
| L-lysyl | arginine | 36 (5) |
| H | alpha-methyl cysteine | 36 (15) |
| formyl | ethionine | 36 (23) |
| pyro-L-glutamyl | alpha-methyl lysine | 38 (2) |
| cyclopentane carbonyl | asparagine | 38 (8) |
| L-arginyl | 5-acetyl-penicillamine | 41 (3) |
| t-butyloxycarbonyl | homocysteine | 41 (15) |
| butanoyl | aspartic acid | 43 (3) |
| benzoyl | alpha-methyl methionine | 43 (16) |
| pyro-L-glutamyl-L-lysyl | threonine | 43 (20) |
| benzoyl | arginine | 46 (2) |
| formyl | ornithine | 46 (10) |
| cyclopentylcarbonyl-L-lysyl | methionine | 49 (3) |
| H | vinylglycine | 49 (9) |
| phenylpropanoyl | omega-nitro-arginine | 52 (2) |
| benzoyl | beta-alanine | 53 |
| t-butyloxycarbonyl | isoserine | 56 (4) |
| H | alpha-methyl-threonine | 56 (13) |
| cyclopentane carbonyl | lysine | 56 (21) |
| L-lysyl | glutamine | 58 |
| benzoyl | alpha-amino-isobutyric acid | 61 (7) |
| acetyl | alpha-methyl leucine | 61 (16) |
| pyro-L-glutamyl | alpha-methyl valine | 65 |
| phenylacetyl | alpha-methyl glutamine | 66 (7) |

EXAMPLE 129

Synthesis of N-alpha-[3-(N-alpha-benzoyl-L-tryptophylthio)-2-D-methylpropanoyl]-1-proline A solution of 62 mg of N-alpha-benzoyl-L-tryptophan in 0.5 ml redistilled dimethylformamide (DMF) was cooled in a ice-dry ice-acetone bath at −20° C. To this solution was added a cold solution of 35 mg of 1,1'-carbonyldiimidazole in 1.0 ml of DMF. The solution was stirred at −10° C. for two hours and then added to a cold solution of 48 mg of 3-mercapto-2-D-methylpropanoyl-L-proline in 1 ml of DMF which was neutralized with N-ethyl morpholine. The reaction mixture was stirred at −10° C. for an additional hour and then slowly warmed to room temperature. The solvent was removed under reduced pressure at 40° C. and ethyl acetate was added to the residue. The mixture was cooled in an ice bath and washed with 0.1N HCl and then three times with saturated NaCl solution. The solvent was removed with a rotary evaporator after drying over anhydrous MgSO4. The product was purified by liquid chromatography on Sephadex LH-20, using a 1.2 cm by 95 cm column and eluted with isopropanol. The peak fractions were pooled and the solvent removed under reduced pressure yielding 60.5 mg of the named product, as a foam-like material. This product was found to be homogeneous using TLC with solvent systems 1, 2, 3 and 5.

EXAMPLES—130–131

By substituting N-alpha-benzoyl-L-tyrosine or N-alpha-benzoyl-L-histidine for the N-alpha-benzoyl-L-tryptophane in Example 129 and substantially following the procedures of Example 129, the following compounds are obtained:

| Example | Compound |
|---|---|
| 130 | N—alpha-[3-(N—alpha-benzoyl-L-tyrosylthio)-2-D-methyl propanoyl-L-proline |
| 131 | N—alpha-[3-(N—alpha-benzoyl-L-histidylthio)-2-D- |

-continued

| Example | Compound |
|---------|----------|
| | methylpropanoyl-L-proline. |

EXAMPLE 132

Similarly, the L-3,4-dehydroproline, D,L-3,4-dehydroproline, L-3-hydroxyproline, L-4-hydroxyproline, and L-thiazolidine-4-carboxylic acid derivatives are obtained by substituting each of the products of Examples 72–75 for the 3-mercapto-2-D-methylpropanoyl-L-proline in each of Examples 129–131, and substantially repeating the procedure of Examples 129 for each substitution.

EXAMPLE 133

Synthesis of N-alpha-[3-(N-alpha-benzoylglycylthio)-2-D-methylpropanoyl]-L-proline A solution of 33 mg of N-alpha-benzoylglycine in 0.5 ml redistilled dimethylformamide (DMF) was cooled in an ice-dry ice-acetone bath at −20° C. To this solution was added a cold solution of 35 mg of 1,1′-carbonyldiimidazole in 1.0 ml of DMF. The solution was stirred at −10° C. for two hours and then mixed with a cold solution of 48 mg of 3-mercapto-2-D-methylpropanoyl-L-proline in 1 ml of DMF which was neutralized with N-ethyl morpholine. The reaction mixture was stirred at −10° C. for an additional hour and then slowly warmed to room temperature. The solvent was removed under reduced pressure at 40° C. and ethyl acetate was added to the residue. The mixture was cooled in an ice bath and washed with 0.1N HCl and then three times with saturated NaCl solution. The solvent was removed with a rotary evaporator after drying over anhydrous MgSO$_4$. The product was purified by liquid chromatography on Sephadex LH-20* using a 1.2 cm by 95 cm column and eluted with THF:isopropanol, 3:7 (parts by volume). The peak fractions were pooled and the solvent removed under reduced pressure yielding 37 mg of the named product. This product was found to be homogeneous using paper electrophoresis at pH 5.0 and using TLC with solvent systems 2, 3, 4 and 5.
*Trademark Pharmacia, Inc. Uppsala, Sweden.

EXAMPLES 134–137

By substituting N-alpha-benzoyl-L-alanine, N-alpha-benzoyl-L-isoleucine, N-alpha-benzoyl-L-leucine, or N-alpha-benzoyl-L-valine for the N-alpha-benzoylglycine in Example 133, and substantially repeating the procedures of Example 133 with each, the following compounds are obtained:

| Example | Compound |
|---------|----------|
| 134 | N—alpha-[3-(N—alpha-benzoyl-L-leucylthio)-2-D-methylpropanoyl-L-proline |
| 135 | N—alpha-[3-(N—alpha-benzoyl-L-isoleucylthio)-2-D-methyl propanoyl]-L-proline |
| 136 | N—alpha-[3-(N—alpha-benzoyl-L-valylthio)-2-D-methyl propanoyl-L-proline |
| 137 | N—alpha-[3-(N—alpha-benzoyl-L-alanylthio)-2-D-methyl propanoyl-L-proline |

EXAMPLE 138

Similarly, the L-3,4-dehydroproline, D,L-3,4-dehydroproline, L-3-hydroxyproline, L-4-hydroxyproline, and L-thiazolidine-4-carboxylic acid derivatives are obtained by substituting each of the various products of Examples 72–75 for the 3-mercapto-2-D-methylpropanoyl-L-proline in each of Examples 133–137, and substantially following the procedures of Example 133 for each substitution.

EXAMPLE 139

Synthesis of N-alpha-[3-(N-alpha-tert-butyloxycarbonyl-L-phenylalanyl-thio)-2-D-methylpropanoyl]-L-proline A solution of 133 mg of N-alpha-tert-butyloxycarbonylL-phenylalanine (N-alpha-Boc-L-phenylalanine) in 0.5 ml redistilled dimethylformamide (DMF) was cooled in an ice-dry ice-acetone bath at −20° C. To this solution was added a cold solution of 87 mg of 1,1′-carbonyldiimidazole in 1.0 ml of DMF. The solution was stirred at −10° C. for two hours and then mixed with a cold solution of 119.5 mg of 3-mercapto-2-D-methylpropanoyl-L-proline in 1 ml of DMF which was neutralized with N-ethyl morpholine. The reaction mixture was stirred at −10° C. for an additional hour and then slowly warmed to room temperature. The solvent was removed under reduced pressure at 40° C. and ethyl acetate was added to the residue. The mixture was cooled in an ice bath and washed with 0.1N HCl and then three times with saturated NaCl solution. The solvent was removed with a rotary evaporator after drying over anhydrous MgSO$_4$. The product was purified by liquid chromatography on Sephadex G-10* using a 1.2 cm×95 cm column and eluted with THF:isopropanol, 3:7 (parts by volume). The peak fractions were pooled and the solvent removed under reduced pressure yielding 165 mg of the named product. This product was found to be homogeneous using paper electrophoresis at pH 5.0 and using TLC with solvent systems 1, 2 and 3.
*Trademark, Pharmacia, Inc., Uppsala, Sweden.

EXAMPLE 140

Synthesis of N-alpha-(3-L-phenylalanylthio-2-D-methylpropanoyl)-L-proline

The product from Example 139 was deprotected by stirring a mixture of 30 mg of the product, 50 ul of anisole and 200 ul of anhydrous trifluoroacetic acid (TFA) at room temperature for one hour. Anisole and TFA were removed under reduced pressure at 35° C. and the residue was triturated with anhydrous ether. The white residue was purified by liquid chromatography on Sephadex G-10 using a 1.2 cm×95 cm column and eluted with 5% acetic acid. The peak fractions were pooled and freeze-dried yielding 17.5 mg of the named compound. This product was found to be homogeneous using paper electrophoresis at pH 1.9 and 5.0 and using TLC with solvent systems 4 and 5.

EXAMPLES 141–148

By substituting N-alpha-Boc-glycine, N-alpha-Boc-alanine, N-alpha-Boc-tryptophan, N-alpha-Boc-tyrosine, N-alpha-Boc-isoleucine, N-alpha-Boc-leucine, N-alpha-Boc-histidine, or N-alpha-Boc-valine for the N-alpha-Boc-phenylalanine in Example 139, and substantially following the procedures of Examples 139 and 140, the following compounds are obtained.

| Example | Compound |
|---|---|
| 141 | N—alpha-(3-glycylthio-2-D-methylpropanoyl)-L-proline |
| 142 | N—alpha-(3-L-tryptophylthio-2-D-methylpropanoyl)-L-proline |
| 143 | N—alpha-(3-L-tyrosylthio-2-D-methylpropanoyl)-L-proline |
| 144 | N—alpha-(3-L-isoleucylthio-2-D-methylpropanoyl)-L-proline |
| 145 | N—alpha-(3-L-leucylthio-2-D-methylpropanoyl)-L-proline |
| 146 | N—alpha-(3-L-histidylthio-2-D-methylpropanoyl)-L-proline |
| 147 | N—alpha-(3-L-valylthio-2-D-methylpropanoyl)-L-proline |
| 148 | N—alpha-(3-L-alanylthio-2-methylpropanoyl)-L-proline |
| 151 | N—alpha-[3-(N—alpha-acetylglycylthio)-2-D-methylpropanoyl]-L-proline |
| 152 | N—alpha-[3-(N—alpha-acetyl-L-tryptophylthio)-2-D-methylpropanoyl]-L-proline |
| 153 | N—alpha-[3-(N—alpha-acetyl-L-tyrosylthio)-2-D-methylpropanoyl]-L-proline |
| 154 | N—alpha-[3-(N—alpha-acetyl-L-isoleucylthio)-2-D-methylpropanoyl]-L-proline |
| 155 | N—alpha-[3-(N—alpha-acetyl-L-leucylthio)-2-D-methylpropanoyl]-L-proline |
| 156 | N—alpha-[3-(N—alpha-acetyl-L-histidylthio)-2-D-methylpropanoyl]-L-proline |
| 157 | N—alpha-[3-(N—alpha-acetyl-L-valylthio)-2-D-methylpropanoyl]-L-proline |
| 158 | N—alpha-[3-(N—alpha-acetyl-L-alanylthio)-2-D-methylpropanoyl]-L-proline |

EXAMPLE 149

Similarly, the L-3,4-dehydroproline, D,L-3,4-dehydroproline, L-3-hydroxyproline, L-4-hydroxyproline, and L-thiazolidine-4-carboxylic acid derivatives are obtained by substituting each of the various products of Examples 72-75, for the 3-mercapto-2-D-methylpropanoyl-L-proline in Examples 139 and 140 and in each of Examples 141-148 and substantially following the procedures of Examples 139 and 140 each time.

EXAMPLE 150

Synthesis of
N-alpha-[3-(N-alpha-acetyl-L-phenylalanylthio)-2-D-methylpropanoyl]-L-proline A solution of 41.5 mg of N-alpha-acetyl-L-phenylalanine in 0.5 ml redistilled dimethylformamide (DMF) was cooled in an ice-dry ice-acetone bath at −20° C. To this solution was added a cold solution of 35 mg of 1,1'-carbonyldiimidazole in 1.0 ml of DMF. The solution was stirred at −10° C. for two hours and then was added to a cold solution of 48 mg of 3-mercapto-2-D-methylpropanoyl-L-proline in 1 ml of DMF which was neutralized with N-ethyl morpholine. The reaction mixture was stirred at −10° C. for an additional hour and then slowly warmed to room temperature. The solvent was removed under reduced pressure at 40° C. and ethyl acetate was added to the residue. The mixture was cooled in an ice bath and washed with 0.1N HCl and then three times with saturated NaCl solution. The organic solvent was removed with a rotary evaporator after drying over anhydrous MgSO₄. The product was purified by Sephadex LH-20[1]/ column chromatography using a 1.2 cm by 95 cm column and eluted with isopropanol. The peak fractions were pooled and the solvent was removed under reduced pressure yielding 35.5 mg of the named product. This product was found to be homogeneous using TLC with solvent systems 1, 2, 3 and 5.

[1]/Trademark, Pharmacia, Inc., Uppsala, Sweden.

EXAMPLES 151-158

By substituting each of N-alpha-acetyl-glycine, N-alphaalanine, N-alpha-acetyl-tryptophan, N-alpha-acetyl-tyrosine, N-alpha-acetyl-isoleucine, N-alpha-acetyl-leucine, N-alpha-acetyl-histidine, or N-alpha-acetyl-valine for the N-alpha-acetyl-phenylalanine in Example 150 and substantially following the procedure of Example 150, the following compounds are obtained.

EXAMPLE 159

Similarly, the L-3,4-dehydroproline, D,L-3,4-dehydroproline, L-3-hydroxyproline, L-4-hydroxyproline and L-thiazolidine4-carboxylic acid derivatives are obtained by substituting each of the various products of Examples 72-75 for the 3-mercapto2-D-methylpropanoyl-L-proline in each of Examples 150-158 and substantially following the procedure of Example 150 in each instance.

EXAMPLE 160

By substituting the N-alpha-formyl, N-alpha-propanoyl, N-alpha-butanoyl, N-alpha-phenylacetyl or N-alpha-phenylpropanoyl derivatives of L-Phe, L-Gly, L-Trp, L-tyr, L-Ile, L-Leu, L-His and L-Val for the N-alpha-acetyl derivatives in each of Examples 151-159 and substantially following the procedure of Example 150, the formyl, propanoyl, butanoyl, phenylacetyl, and phenylpropanoyl derivatives are obtained.

EXAMPLE 161

Synthesis of
N-alpha-[3-(N-tertiary-butyloxycarbonyl-L-phenylalanylthio)-2-D-methylpropanoyl]-L-proline A solution of 133 mg of N-alpha-tertiary-butyloxycarbonyl-L-phenylalanine (N-alpha-Boc-L-Phe) in 0.5 ml redistilled dimethylformamide (DMF) was cooled in an ice-dry ice-acetone bath at −20° C. To this solution was added a cold solution of 87 mg of 1,1'-carbonyldiimidazole in 1.0 ml of DMF. The solution was stirred at −10° C. for two hours and then was added to a cold solution of 119.5 mg of 3-mercapto-2-D-methylpropanoyl-L-proline in 1 ml of DMF which was neutralized with N-ethyl morpholine. The reaction mixture was stirred at −10° C. for an additional hour and then slowly warmed to room temperature. The solvent was removed under reduced pressure at 40° C. and ethyl acetate was added to the residue. The mixture was cooled in an ice bath and washed with 0.1N HCl and then three times with saturated NaCl solution. The solvent was removed with a rotary evaporator after drying over anhydrous MgSO₄. The product was purified by liquid chromatography on Sephadex G-10[2]/ using a 1.2 cm by 95 cm column and eluted with THF:isopropanol, 3:7 (parts by volume). The peak fractions were pooled and the solvent removed under reduced pressure yielding 165 mg of the named product. This product was found to be homogeneous using paper electrophoresis at pH 5.0 and using TLC with solvent systems 1, 2 and 3.

2/Trademark, Pharmacia, Inc., Uppsala, Sweden.

EXAMPLES 162-169

By substituting each of N-alpha-Boc-glycine, N-alpha-Boc-alanine, N-alpha-Boc-tryptophan, N-alpha-tyrosine, N-alpha-Boc-isoleucine, N-alpha-Boc-leucine, N-alpha-Boc-histidine or N-alpha-boc-valine for the N-alpha-Boc-Phe in Example 161 and substantially following the procedures of Example 161, the following compounds are obtained.

| Example | Compound |
| --- | --- |
| 162 | N—alpha-[3-(N—alpha-butyloxycarbonylglycylthio)-2-D-methylpropanoyl]-L-proline |
| 163 | N—alpha-[3-(N—alpha-butyloxycarbonyl-L-tryptophylthio)-2-D-methylpropanoyl]-L-proline |
| 164 | N—alpha-[3-(N—alpha-butyloxycarbonyl-L-tyrosylthio)-2-D-methylpropanoyl]-L-proline |
| 165 | N—alpha-[3-(N—alpha-butyloxycarbonyl-L-isoleucylthio)-2-D-methylpropanoyl]-L-proline |
| 166 | N—alpha-[3-(N—alpha-butyloxycarbonyl-L-leucylthio)-2-D-methylpropanoyl]-L-proline |
| 167 | N—alpha-[3-(N—alpha-butyloxycarbonyl-L-histidylthio)-2-D-methylpropanoyl]-L-proline |
| 168 | N—alpha-[3-(N—alpha-butyloxycarbonyl-L-valylthio)-2-D-methylpropanoyl]-L-proline |
| 169 | N—alpha-[3-(N—butyloxycarbonyl-L-alanylthio)-2-D-methylpropanoyl]-L-proline |

EXAMPLE 170

Similarly, the L-3,4-dehydroproline, D,L-3,4-dehydroproline, L-3-hydroxyproline, L-4-hydroxyproline, and L-thiazolidine-4-carboxylic acid analogs are obtained by substituting each of the products of Examples 72-75 for the 3-mercapto-2-D-methylpropanoyl-L-proline in each of Examples 161-169 and substantially following the procedure of Example 161 in each instance.

EXAMPLE 171

Synthesis of N-alpha-[3-(N-alpha-cyclopentylcarbonyl-L-phenylalanylthio)-2-D-methylpropanoyl]-L-proline A solution of 52.5 mg of the compound from Example 4 in 0.5 ml redistilled dimethylformamide (DMF) was cooled in an ice-dry ice-acetone bath at −20° C. To this solution was added a cold solution of 34 mg of 1,1′-carbonyldiimidazole in 1.0 ml of DMF. The solution was stirred at −10° C. for two hours and then mixed with a cold solution of 45.6 mg of 3-mercapto-2-D-methylpropanoyl-L-proline in 1 ml of DMF which was neutralized with N-ethyl morpholine. The reaction mixture was stirred at −10° C. for an additional hour and then slowly warmed to room temperature. The solvent was removed under reduced pressure at 40° C. and ethyl acetate was added to the residue. The mixture was cooled and washed with 0.1N HCl and then three times with saturated NaCl solution. The solvent was removed with a rotary evaporator after drying over anhydrous MgSO4. The product was purified by LH-20[3/] column chromatography using a 1.2 cm by 95 cm column and eluted with isopropanol. The peak fractions were pooled and the solvent was removed under reduced pressure yielding 60.5 mg of the named product. This product was found to be homogeneous using TLC in solvent systems 1, 2, 3 and 5.

3 /Trademark, Pharmacia, Inc., Uppsala, Sweden

EXAMPLES 172-179

By substituting each of the benzoyl ester toluenesulfonate salts of glycine, L-alanine, L-tryptophan, L-tyrosine, L-isoleucine, L-leucine, L-histidine or L-valine for the L-Phe salt in Example 4 and substantially following the procedures of Examples 4 and 17 in each instance the following compounds are obtained.

| Example | Compound |
| --- | --- |
| 172 | N—alpha-[3-(N—alpha-cyclopentylcarbonylglycylthio) 2-D-methylpropanoyl]-L-proline |
| 173 | N—alpha-[3-(N—alpha-cyclopentylcarbonyl-L-tryptophylthio)-2-D-methylpropanoyl]-L-proline |
| 174 | N—alpha-[3-(N—alpha-cyclopentylcarbonyl-L-tyrosylthio)-2-D-methylpropanoyl]-L-proline |
| 175 | N—alpha-[3-(N—alpha-cyclopentylcarbonyl-L-isoleucylthio)-2-D-methylpropanoyl]-L-proline |
| 176 | N—alpha-[3-(N—alpha-cyclopentylcarbonyl-L-leucylthio)-2-D-methylpropanoyl]-L-proline |
| 177 | N—alpha-[3-(N—alpha-cyclopentylcarbonyl-L-histidylthio)-2-D-methylpropanoyl]-L-proline |
| 178 | N—alpha-[3-(N—alpha-cyclopentylcarbonyl-L-valylthio)-2-D-methylpropanoyl]-L-proline |
| 179 | N—alpha-[3-(N—alpha-cyclopentylcarbonyl-L-alanylthio)-2-D-methylpropanoyl]-L-proline |

EXAMPLE 180

Similarly, each of 3-mercapto-2-D-methylpropanoyl derivatives of the L-3,4-dehydroproline, D,L-3,4-dehydroproline, L-3-hydroxyproline, L-4-hydroxyproline and L-thiazolidine-4-carboxylic acid are obtained by substituting the products of Examples 72-75 for the 3-mercapto-2-D-methylpropanoyl-L-proline in each of Examples 172-179 and substantially following the procedure of Example 171.

EXAMPLE 181

Synthesis of N-alpha-[3-(N-alpha-cyclopentylcarbonyl-N-epsilon-tert-butyloxycarbonyl-L-lysyl-L-phenylalanylthio)-2-D-methylpropanoyl]-L-proline A solution of 73.5 mg of the product from Example 6 in 0.5 ml redistilled dimethylformamide (DMF) was cooled in an ice-dry ice-acetone bath at −20° C. To this solution was added a cold solution of 26 mg of 1,1′-carbonyldiimidazole in 1.0 ml of DMF. The solution was stirred at −10° C. for two hours and then mixed with a cold solution of 36 mg of 3-mercapto-2-D-methylpropanoyl-L-proline in 1 ml of DMF which was neutralized with N-ethyl morpholine. The reaction mixture was stirred at −10° C. for an additional hour and then slowly warmed to room temperature. The solvent was removed under reduced pressure at 40° C. and ethyl acetate was added to the residue. The mixture was cooled in an ice water bath and washed with 1N citric acid and then three times with saturated NaCl solution. The solvent was removed with a rotary evaporator after drying over anhydrous MgSO4. The product was purified by LH-20 column chromatography using a 1.2 cm by 95 cm column and eluted with THF:isopropanol, 3:7 (parts by volume). The peak fractions were pooled and the solvent was removed under reduced pressure yielding the named product which may be abbreviated as N-alpha-[3-N-alpha-Cpc-N-epsilon-Boc-L-Lys-L-Phe-thio)-2-D-methylpropanoyl]-L-proline.

EXAMPLE 182

Synthesis of N-alpha-[3-(N-alpha-cyclopentylcarbonyl-L-phenylalanylthio)-2-D-methylpropanoyl]-L-proline The N-epsilon-Boc group was removed from the lysine by stirring a mixture of 30 mg of the product from Example 180 with 50 μl anisole and 200 μl of anhydrous trifluoroacetic acid (TFA) at room temperature for one hour. Anisole and TFA were removed under reduced pressure at 35° C. and the residue was triturated with anhydrous ether. The residue was purified by liquid chromatography on Sephadex G-10*/ using a 1.2 cm by 95 cm column and eluted with 5% acetic acid. The peak fractions were pooled and freeze-dried yielding the named product which can be abbreviated as N-alpha-[3-(N-alpha-Cpc-L-Lys-L-Phe-thio)-2-D-methylpropanoyl]-L-proline.

*/Trademark, Pharmacia, Inc., Uppsala, Sweden.

EXAMPLES 183–190

By substituting each of glycine, L-alanine, L-tryptophan, L-tyrosine, L-isoleucine, L-leucine, L-histidine, and L-valine for the L-phenylalanine in Example 6 and substantially following the procedures of Examples 181 and 182 in each case, the following compounds are obtained.

| Example | Compound |
|---|---|
| 183 | N—alpha-[3-(N—alpha-cyclopentylcarbonyl-L-lysyl-glycylthio)-2-D-methylpropanoyl]-L-proline |
| 184 | N—alpha-[3-(N—alpha-cyclopentylcarbonyl-L-lysyl-L-tryptophylthio)-2-D-methylpropanoyl]-L-proline |
| 185 | N—alpha-[3-(N—alpha-cyclopentylcarbonyl-L-lysyl-L-tyrosylthio)-2-D-methylpropanoyl]-L-proline |
| 186 | N—alpha-[3-(N—alpha-cyclopentylcarbonyl-L-lysyl-L-isoleucylthio)-2-D-methylpropanoyl]-L-proline |
| 187 | N—alpha-[3-(N—alpha-cyclopentylcarbonyl-L-lysyl-L-leucylthio)-2-D-methylpropanoyl]-L-proline |
| 188 | N—alpha-[3-(N—alpha-cyclopentylcarbonyl-L-lysyl-L-histidylthio)-2-D-methylpropanoyl]-L-proline |
| 189 | N—alpha-[3-(N—alpha-cyclopentylcarbonyl-L-lysyl-L-valylthio)-2-D-methylpropanoyl]-L-proline |
| 190 | N—alpha-[3-(N—alpha-cyclopentylcarbonyl-L-lysyl-L-alanylthio)-2-D-methylpropanoyl]-L-proline |

EXAMPLE 191

By substituting pyro-glutamic acid for the cyclopentanecarboxylic acid in Example 6 and substantially following the procedures of Example 6, steps (a), (b) and (c), N-alphapyro-glutamyl-N-epsilon-tert-butyloxycarbonyl-L-lysine-N-hydroxysuccinimide ester is obtained. By substituting this product for the N-alpha-Cpc-N-epsilon-Boc-L-Lys-N-hydroxysuccinimide ester in Example 6, step (d), and substantially repeating each of Examples 183–191, the pyro-glutamyl derivatives are obtained.

EXAMPLE 193

Preparation of N-alpha-[3-(Pyro-L-glutamyl-L-phenylalanylthio)-2-D-methylpropanoyl]-L-proline A solution of 87 mg of 1,1'-carbonyldiimidazole in 1.0 ml DMF was added to a solution of 139 mg of the product of Example 9 in 0.5 ml DMF at −15° C. The reaction mixture was stirred at −10° C. for 1 hour, and then a mixture of 119.5 mg of 3-mercapto-2-D-methylpropanoyl-L-proline and 0.072 ml of N-ethyl morpholine in 1 ml DMF was added. The reaction mixture was stirred at −10° C. for an additional hour and then was slowly warmed to room temperature. DMF was removed under reduced pressure with a rotary evaporator at 40° C. and then 7 ml ethyl acetate and 2 ml 1N citric acid were added. The organic phase was washed two times with 1N citric acid and two times with saturated NaCl. The organic phase was dried with anhydrous MgSO$_4$ and then filtered. Solvent was removed using a rotary evaporator. The residue was purified on Sephadex G-25*/ (1.2×99 cm) partition column chromatography with n-butanol:acetic acid:H$_2$O (4:1:5 by volume). The product was homogeneous on TLC (systems 1, 2 and 3) and on electrophoresis at pH 5.0.

*/Trademark, Pharmacia, Inc., Uppsala, Sweden.

EXAMPLE 194

By substituting the corresponding benzyl ester derivatives of Gly, Ala, Trp, Tyr, Ile, Leu, His or Val in Example 9 in lieu of the Phe benzyl ester derivative and then subjecting the product in each instance to the process of Example 193, the corresponding pyroglutamyl-Gly, -Ala, -Trp, -Tyr, -Ile, -Leu, -His and -Val analogs of the Example 193 product are each obtained.

EXAMPLE 195

Substitution of bis-Boc-L-Lys or tri-Adoc-L-Arg for pyro-L-glutamic acid in Examples 9 and 193 and in each of the Example 194 processes gives the analogous bis-Boc-L-Lys and tri-Adoc-L-Arg derivatives in each case.

EXAMPLE 196

Preparation of N-[3-(benzoyl-L-phenylalanylthio)-2-D-methylpropanoyl]-L-proline (a) Preparation of N-[3-(Boc-L-phenylalanylthio-2-D-methylpropanoyl]-L-proline A solution of 133 mg (0.5 mmole) of Boc-L-phenylalanine of redistilled dimethylformamide (DMF) was cooled to −20° C. in an ice-dry ice-acetone bath. A cooled solution of 87 mg (0.54 mmole) of 1,1'-carbonyl-diimidazole in 1 ml of DMF was added and the resulting solution was stirred at −10° C. for 2 h. DMF, 1.0 ml, containing 119.5 mg (0.55 mmole) of 2-D-methyl-3-mercaptopropanoyl-L-proline and 0.075 ml (0.55 mmole) of N-ethylmorpholine, all at −10° C., was added, and the final solution was stirred at −10° C. for 1 h. The reaction mixture was slowly warmed to room temperature. Solvent was removed with a rotary evaporator. Ethyl acetate (10 ml) was added, and the solution was cooled in an ice bath. The organic solution was washed twice with about 2 ml of 1N citric acid and then was washed twice with a saturated NaCl solution. The ethyl acetate phase was dried over anhydrous MgSO$_4$ and then filtered. The solvent of the filtrate was removed with a rotary evaporator. The residue was dissolved in a small volume of isopropanol/tetrahydrofuran (7:3 by vol) and was applied to a column (1.2×99 cm) of Sephadex LH-20 equilibrated with the same solvent. Each column eluent fraction contained 2.55 ml. Fractions 31–36 were pooled, and solvent was removed by rotary evaporation. The residue was again dissolved in the isopropanoyl/tetrahydrofuran solvent and was applied to a column (1.2×98 cm) of Sephadex G-10 equilibrated and developed with the same solvent. Fractions, 2.55 ml each, were collected. Fractions 19–23 were pooled and yielded 165 mg of the desired product. Purification of side fractions from the LH-20 chromatography step yielded 40 mg of product. The product behaved as a pure substance on paper electrophoresis at pH 5.0 and on thin layer chromatography (silica gel plates) using three solvent systems. Amino acid analysis: $^{Phe}1.00$, $^{Pro}1.01$.

b. Preparation of
N-[3-(HCl.H-L-phenylalanylthio)-2-D-methyl-propanoyl]-L-proline Anisole (0.2 ml) was added to 200 mg of N-[3-(Boc-L-phenylalanylthio)-2-D-methyl-propanoyl]-L-proline, and the mixture was stirred at 0° C. Anhydrous trifluoroacetic acid (0.4 ml) was added, and the solution was stirred at room temperature (~22° C.) for 45 min. Trifluoroacetic acid was removed by rotary evaporation at 30° C. and then 1 ml of ethyl acetate saturated with hydrogen chloride was added. Excess HCl and ethyl acetate were removed with a rotary evaporator to yield an oily residue. Anhydrous ethyl ether was added, and the mixture was allowed to stand at 0° C. for 1 h. A white solid was recovered by filtration and washed several times with anhydrous ether. The solid material was dried in a vacuum desiccator over NaOH and $P_2O_5$.

c. Preparation of
N-[3-(benzoyl-L-phenylalanylthio)-2-D-methyl-propanoyl]-L-proline A solution of 93 mg (0.23 mmole) of N-[3-(HCl H-L-phenylalanylthio)-2-D-methyl-propanoyl]-L-proline in 0.5 ml of dioxane (redistilled over Na) was mixed with 0.029 ml (0.25 mmole) of benzoylchloride in 0.099 ml (0.71 mmole) of N-ethyl morpholine. After 1 h of reaction at room temperature, an additional 0.029 ml of benzoylchloride and 0.034 ml of N-ethyl morpholine were added. One h after the second addition, glacial acetic acid (0.2 ml) was added. Solvent was removed by rotary evaporation at 35° C. The crude product was purified by partition chromatography [1.2×97 cm column of Sephadex G-25 equilibrated with n-butanol/acetic acid/$H_2O$ (4:1:5)]. The sample was dissolved in a mixture of 0.3 ml of lower phase and 0.3 ml of upper phase. Elution was begun with upper phase. Fractions (2.75 ml each) were collected. Fractions 16–18 were pooled, and solvent was removed at 37° C. with a rotary evaporator. The product was then applied to a column (1.2×98 cm) of silica gel equilibrated and developed with ethyl acetate. Fractions (5.15 ml each) were collected. Fractions 46–60 were pooled and yielded 52.5 mg of product. The product behaved like a pure substance on thin layer chromatography using two solvent systems.

EXAMPLE 197

Preparation of
N-[3-(benzoyl-D-phenylalanylthio)-2-D-methyl-propanoyl]-L-proline a. Preparation of
N-[3-(HCl.H-D-phenylalanylthio)-2-D-methyl-propanoyl]-L-proline A solution of 531 mg (2 mmoles) of Boc-D-phenylalanine in 3 ml of redistilled dimethylformamide (DMF) was cooled to −20° C. and stirred vigorously. 1,1'-carbonyldiimidazole (341 mg; 2.1 mmole) in 3 ml of DMF (at −10° C.) was added, and the resulting solution was stirred at −10° C. for 2 h. A solution of 2-D-methyl-3-mercaptopropanoyl-L-proline (456 mg; 2.1 mmole) in 2 ml of DMF and 0.285 ml of N-ethyl morpholine (2.1 mmole) was added, and the reaction mixture was stirred at −10° C. for 1 h. The mixture was slowly warmed to room temperature. Solvent was removed by rotary evaporation at 35° C. The residue was dissolved in ethyl acetate (25 ml) and 3 ml of water was added. The mixture was cooled to 0° C. and then acidified with 0.3 ml of concentrated HCl. The organic phase was washed once with cold dilute HCl, three times with water, and three times with saturated NaCl. The organic phase was dried over anhydrous $MgSO_4$ and then was filtered. The solvent was removed by rotary evaporation to yield an oily residue. The product was purified on a column (2.2×98 cm) of Sephadex LH-20 equilibrated and developed with isopropanol/tetrahydrofuran (7:3 by vol). Fractions (5.6 ml each) were collected. Fractions 34–38 were pooled. Fractions 33, 39, 40 and 41 were pooled, solvents removed and reapplied to the LH-20 column. Fractions 37–40 of the rechromatographed material and fractions 34–38 of the first chromatography were further purified on a column (1.2×98 cm) of silica gel equilibrated and developed with ethyl acetate. Fractions (5.0 ml each) were collected. Fractions 22–29 were pooled, and solvent was removed by rotary evaporation. The residue was dissolved in 1 ml of anhydrous trifluoroacetic acid containing 0.5 ml of anisole. Deprotection proceeded at room temperature for 0.5 h. Solvent was removed by rotary evaporation at 35° C. The residue was dissolved in 1 ml of ethyl acetate saturated with hydrogen chloride. Anhydrous ether, 5 ml, was added at 0° C., and a white precipitate formed. After 1 h at 0° C., the white solid was collected by filtration and was washed five times with ether. The product was dried overnight in a vacuum desiccator over NaOH and $P_2O_5$. Yield: 381 mg.

b. Preparation of N-[3-(benzoyl-D-phenylalanylthio)-b 2-D-methyl-propanoyl]-L-proline The product of stage a. above, N-[3-(HCl.H-D-phenylalanylthio)-2-D-methyl-propanoyl]-L-proline (93 mg; 0.23 mmole), was reacted with benzoylchloride (0.029 ml; 0.25 mmole) in 0.5 ml of redistilled anhydrous dioxane (0° C.) and 0.099 ml (0.71 mmole) of N-ethyl morpholine. The reaction mixture was stirred vigorously at room temperature for 3 h. Benzoylchloride, 0.015 ml, and N-ethyl morpholine, 0.018 ml, were added and the mixture was stirred for 1 h. Solvent was removed by rotary evaporation at 30° C. The residue was dissolved in a small amount of upper and lower phase of n-butanol/acetic acid/$H_2O$ (4:1:5) and was applied to a column (1.2×98 cm) of Sephadex G-25 equilibrated for partition chromatography. The column was developed with upper phase as the moving phase (2.6 ml fractions). Fractions 15–24 were pooled and solvent removed by rotary evaporation. The residue was dissolved in a small amount of ethyl acetate and further purified on a silica gel (1.2×95 cm column) equilibrated and developed with ethyl acetate (5 ml fractions). The fractions containing the major peak were pooled and solvent was removed. The material was further purified by chromatography on Sephadex LH-20 (1.8×89 cm column) equilibrated and developed isopropanol/tetrahydrofuran (7:3 by vol). Fractions (5.7 ml each) were collected, and the desired material was eluted in fractions 15–17 (yield 98 mg). The final product behaved as a pure substance on paper electrophoresis at pH 5.0 and 2.0 and on thin layer chromatography.

EXAMPLE 198

Preparation of N-[3-(benzoyl-D,L-phenylalanylthio)-2-D-methyl-propanoyl]-L-proline By using a 50:50 mixture of Boc-D-phenylalanine and Boc-L-phenylalanine in the procedures of Example 196 or 197 above, N-[3-(benzoyl-D,L-phenylalanylthio)-2-D-methyl-propanoyl]-L-proline is prepared.

EXAMPLE 199

Preparation of N-(2-benzoylphenylalanylthiopropanoyl)-L-proline and N-(3-benzoylphenylalanylthiopropanoyl)-L-proline derivatives The desired compounds are prepared by substituting 2-mercaptopropanoyl-L-proline and 3-mercaptopropanoyl-L-proline for 2-D-methyl-3-mercaptopropanoyl-L-proline in the procedures of each of Examples 196–198, and reacting the mercapto compound with either Boc-D-phenylalanine, Boc-L-phenylalanine, or a 50:50 mixture thereof, to form the desired D-Phe, L-Phe or D,L-Phe derivative.

EXAMPLE 200

Preparation of L-3,4-dehydroproline, D,L-3,4-dehydroproline, L-3-hydroxyproline, L-4-hydroxyproline and L-thiazolidine-4-carboxylic acid analogs of compounds of Examples 196–199

The desired compounds are prepared by using the appropriate mercapto compound in which L-3,4-dehydroproline, D,L-3,4-dehydroproline, L-3-hydroxyproline, L-4-hydroxyproline or L-thiazolidine-4-carboxylic acid is substituted for L-proline in the procedures of each of Examples 196–199.

EXAMPLE 201

Preparation of D-alanyl, D-tryptophyl, D-tyrosyl, D-isoleucyl, D-leucyl, D-histidyl and D-valyl analogs of compounds of Examples 197 and 200

The desired compounds are each prepared by substituting Boc-D-alanine, Boc-D-tryptophan, Boc-D-tyrosine, Boc-D-isoleucine, Boc-D-leucine, Boc-D-histidine or Boc-D-valine for Boc-D-phenylalanine in the procedures of each of Examples 197 and 200.

EXAMPLE 202

Preparation of D,L-alanyl, D,L-tryptophyl, D,L-tyrosyl, D,L-isoleucyl, D,L-leucyl, D,L-histidyl and D,L-valyl derivatives A 50:50 mixture of Boc-D-$A_1$ and Boc-L-$A_1$, wherein $A_1$ is alanine, tryptophan, tyrosine, isoleucine, leucine, histidine and Boc-L-phenylalanine in the procedure of Example 198 and 200 to obtain the desired compounds.

EXAMPLE 203

By substituting the appropriate compound for benzoyl chloride in each of Examples 196, 197 and 200–202 and following procedures well known in the art as hereinbefore described, the formyl, acetyl, propanoyl, butanoyl, phenylacetate, phenylpropanoyl, cyclopentanecarbonyl, cyclopentanecarbonyl-L-lysyl, pyro-L-glutamyl-L-lysyl, L-lysyl, L-arginyl and pyro-L-glutamyl derivatives are each prepared.

EXAMPLE 204

Preparation of N-[3-(benzoyl-L-phenylalanylthio)-2-methyl-propanoyl]-L-5-oxo-proline L-glutamic acid, 10 mmoles is reacted with 11 mmoles of the acid chloride of methacrylic acid in 35 ml of 1N sodium hydroxide. After 60 min. at room temperature, the reaction is terminated by adding 2N HCl to a pH of ~2. The reaction product is extracted twice with an equal volume of ethyl acetate. The organic phase is reduced to a small volume on a rotary evaporator, and the product is crystallized by adding ethyl ether. The solid product is collected by filtration. Six mmoles of the product are reacted with 6 mmoles of cyclo-hexylcarbodiimide in 25 ml of anhydrous tetrahydrofuran at 0° C. for 1 h and then at 4° C. overnight. The dicyclohexylurea is removed by filtration. The solvent of the filtrate is removed with a rotary evaporator. The resulting anhydride (5 mmoles) is dissolved in 3 ml of anhydrous THF and 6 ml of anhydrous ethyl ether. To the latter solution is added dicyclohexylamine, 5 mmoles in 2 ml of ethyl ether, to yield methacryloyl-L-5-oxo-proline. The salt is converted to the free acid by adding 2N HCl to pH 2.0. The product is extracted into ethyl acetate. The organic phase is evaporated to dryness and the product is crystallized from a mixture of hexane and ethyl acetate. The methacryloyl-L-5-oxoproline, 3 mmoles in 5 ml of toluene, is reacted with thiolacetic acid, 3 mmoles, by refluxing for 1 h to yield 3-acetylthio-2-methyl-propanoyl-L-5-oxo-proline. The product is crystallized in a mixture of ethyl acetate and hexane. The 3-acetylthio-2-methyl-propanoyl-L-5-oxo-proline is deprotected in liquid $NH_3$ in methanol in the presence of anisole. Solvent is removed with a rotary evaporator. The product is dissolved in ethyl acetate and the organic phase is washed with cold dilute HCl. The solvent of the organic phase is removed with a rotary evaporator. The residue is dissolved in dimethylformamide, 4 ml, 1-hydroxybenzotriazole, 2 mmoles, and the N-hydroxy-succinimide ester of benzoyl-L-phenylalanine, 2 mmoles, are added. The reaction is allowed to proceed at room temperature for 48 h. The solvent is removed with a rotary evaporator. The residue is dissolved in a small volume of ethyl acetate. The organic phase is washed with cold dilute HCl and then saturated NaCl. The organic phase is dried over $MgSO_4$. The $MgSO_4$ is removed by filtration and solvent of the filtrate is removed with a rotary evaporator. The residue is dissolved in 0.5 ml of THF. The resulting solution is applied to a column (2.5×100 cm) of LH-20 eqilibrated and developed with THF. The fractions containing the desired product (detectable by its absorption at 280 nm) are combined, and solvent is removed in a rotary evaporator under high vacuum.

EXAMPLE 205 a. Synthesis of 2-benzoylphenylalanylthiopropanoic acid

A solution of benzoyl-phenylalanie prepared as in Example 1, in 30 ml of redistilled dimethylformamide (DMF) is cooled to −20° C. A solution of 1,1'-carbonyldiimidazole in 10 ml redistilled DMF is added dropwise with vigorous stirring. Temperature is not allowed to exceed −14° C. Following the addition, the solution is stirred at −10° C. for two hours. D,L-Thiolactic acid in redistilled DMF previously neutralized with redistilled N-ethylmorpholine is then added with continued stirring at −10° C. for one hour. The solution is then slowly warmed to room temperature. An approximately equal volume of ethyl acetate is added. The mixture is then cooled and neutralized with concentrated HCl in saturated NaCl. The organic phase is then washed three times with subsaturated NaCl, i.e., five volumes saturated NaCl diluted with one volume water. In some cases a three-layer system is observed. In such cases, the middle layer is saved and combined with the lower aqueous phase. The organic phase is dried over anhydrous $MgSO_4$, filtered and placed in the rotary evaporator to remove solvent. The combined aqueous phase and middle phase is acidified at 0° C. with concentrated HCl to pH 2, and extracted three times with ethyl acetate. The organic phase is washed with saturated NaCl and dried over anhydrous magnesium sulfate, filtered and rotary evaporated. A clear oil is recovered.

The resulting product, 2-benzoylphenylalanylthiopropanoic acid is useful for further synthesis of compounds of this invention. The D- and L-isomers may be resolved and then coupled to L-3,4-dehydropropline by conventional techniques.

b. Synthesis of N-(2-benzoylphenylalanylthiopropanoyl)-L-3,4-dehydroproline

Boc-L-3,4-dehydroproline (213 mg; 1 mmole) was deprotected with 1 ml of anhydrous trifluoroacetate acid for 1 hour. Anhydrous ethyl ether, ~3 ml, was added. Solvents were removed using a rotary evaporator at 30° C. The residue was washed three times with ether and then was dried in a vacuum dessicator over NaOH.

A solution of 358 mg (1 mmole) of 2-benzoylphenylalanylthiopropanoic acid in 3 ml of redistilled DMF was cooled to −20° C. in a dry ice-acetone bath. A solution of 1,1′-carbonyldiimidazole, 171 mg (1.05 mmole) in 1 ml of redistilled DMF was added dropwise, and the temperature of the reaction mixture was maintained at −10° C. and −15° C. The reaction mixture was stirred for two hours. A cold solution of 1-3,4-dehydroproline trifluoroacetate in 2 ml of DMF (neutralized with triethylamine) was added. The reaction mixture was warmed slowly to room temperature. Solvent was removed by rotary evaporation, using high vacuum, at 35+ C. The residue was dissolved in 10 ml of ethyl acetate and 2 ml of $H_2O$. The mixture was acidified with 1N HCl to pH 2 at 0° C. and was mixed. The organic phase was separated and saved. The aqueous phase was extracted three more times with 5 ml of ethyl acetate.

The combined organic phase was washed twice with $H_2O$, three times with saturated NaCl and then was decolorized with charcoal. The organic phase was dried with anhydrous $MgSO_4$ and then filtered. The filtrate was evaporated to dryness on a rotary evaporator, and an oily product, 366 mg, was obtained. The product was purified by chromatography on Sephadex LH-20 (1.2×98 cm) equilibrated and eluted with methanol. Fractions of 150 drops (2.9 ml) were collected. The desired compound was eluted in fractions 24–29. Solvent was removed by rotary evaporation.

Additional purification was achieved by a second chromatography step on Sephadex LH-20. The second column was equilibrated and eluted with isopropanol, peak fractions were pooled and solvent was removed by rotary evaporation. The product was approximately 95% pure as judged by thin layer chromatography in two solvent systems: benzene:acetic acid:water, 9:9:1 (part by volume), and n-butanol:acetic acid-water, 150:26:24 (parts by volume).

EXAMPLE 206 a. Preparation of 2-thiopropanoyl-L-3,4-dehydroproline

Two mg of N-(2-benzoylphenylalanylthiopropanoyl)-L-3,4-dehydroproline, prepared as described in Example 203, was hydrolyzed with 0.5 ml of 5.5N $NH_3$ in methanol for 30 minutes at room temperature. $NH_3$ and methanol were removed by a stream of dry $N_2$. One mole equivalent of D,L-dithiothreitol was added before assay.

The reaction products were separated by chromatography on Sephadex LH-20, eluted with isopropanol as described in Example 203.

b. Preparation of N-Benzoyl-Phenylalanine-N-hydroxy Succinimide ester 1.347 g. of Benzoyl-Phenylalanine and 0.576 g of N-hydroxy succinimide were mixed in a 1:1 (by volume) mixture of THF and dimethylformamide (DMF). The mixture was incubated at 4° C. overnight in the presence of 1.133 g of dicyclohexylcarbodiimide.

The reaction mixture was filtered and the solvent was removed under reduced pressure at 30° C. A white residue remained which was recrystallized from THF-isopropyl alcohol to yield 1.194 g (65.2%) of a white solid, m.p. 156° C.–157° C. The infrared absorption spectrum in chloroform showed bands at 3440 cm$^{-1}$ indicating an NH group, at 1818 cm$^{-1}$, 1790 cm$^{-1}$, and 1744 cm$^{-1}$, characteristic of the N-carboxy succinimide group and at 1669 cm$^{-1}$, characteristic of the N-Benzoyl moiety.

c. Synthesis of N-(2-benzoylphenylalanyl-thiopropanoyl)-L-3,4,-dehydroproline

A reaction mixture containing 2-thiopropanoyl-L-3,4-dehydroproline, prepared as described in step a hereof, 1-hydroxybenzotriazole (HOBt), and N-benzoylphenylalanyl-N-hydroxy-succinimide ester, prepared as described in step b hereof, is cooled in an ice bath at approximately 0° C., after which N-ethylmorpholine is added. The reaction mixture is stirred in an ice bath for three hours, incubated at 4° C. overnight, then at room temperature for 20 hours. The reaction is terminated by the addition of N,N-dimethyl-1,3-propanediamine, and stirred for an additional two hours. Ethyl acetate is added to the reaction mixture which is then washed by extraction with cold 0.1N HCl, followed by two washes with water and three washes with saturated NaCl. The mixture is then dried over anhydrous $MgSO_4$ and filtered. The solvent is removed under reduced pressure in a rotary evaporator, yielding a clear, oily product.

The product is purified by chromatography on Sephadex LH-20, eluted with THF. Re-chromatography of side fractions may yield additional product. Peak fractions are pooled and the solvent removed under high vacuum. The product is washed with ether, then dissolved in THF, transferred to a vial, dried in the stream of nitrogen, then further dried over $P_2O_5$ overnight.

EXAMPLE 207

Synthesis of N-[3-(benzoylphenylalanylthio)-2-D-methylpropanoyl]-L-3,4-dehydroproline The compound is synthesized essentially by the method of Example 205, by coupling L-3,4-dehydroproline to 3-(benzoylphenylalanylthio)-2-D-methylpropanoic acid using 1,1'-carbonyldiimidazole.

This compound is alternatively synthesized essentially by the method of Example 206, step c, starting from 3-thio-2-D-methylpropanoyl-L-3,4-dehydroproline and N-benzoylphenylalanyl-N-hydroxy-succinimide ester.

EXAMPLE 208

Synthesis of N-(3-benzoylphenylalanylthiopropanoyl)-L-3,4,-dehydroproline

This compound is synthesized essentially by the method of Example 205, by coupling 1-3,4-dehydroproline to 3-benzoylphenylalanylthiopropanoic acid using 1,1'-carbonyldiimidazole.

The compound is alternatively synthesized essentially by the method of Example 206, step c, starting from 3-thiopropanoyl-L-3,4-dehydroproline and N-benzoylphenylalanyl-N-hydroxysuccinimide ester.

EXAMPLE 209

Preparation of the sodium salt of N-alpha[3-(N-alpha-benzoyl-D,L-phenylalanylthio)-2-D-methylpropanoyl]-L-proline $NaHCO_3$ (0.5 mmole of a 1M solution) was added to 234.3 mg (0.5 mmole) of N-alpha[3-(Bz-D,L-phenylalanylthio)-2-D-methylpropanoyl]-L-proline in 1 ml of absolute ethanol with stirring. Solvents were removed with a rotary evaporator at approximately $-35°$ C. Fresh ethanol was added to the oily residue and again solvent was removed with the rotary evaporator. The procedure was repeated once more with absolute alcohol and then twice with benzene. The white residue was dried in a vacuum desiccator over $P_2O_5$. Recrystallization from 95% ethanol and benzene yielded 135 mg (55.1% yield) of white crystals having a decomposition point of 185°–186° C. (softens at 153° C.). Infrared analysis using a KBr pellet showed zwitterion bands at 1398 and 1600 $cm^{-1}$ and a thio ester band at 1682 $cm^{-1}$. Paper electrophoresis at pH 2 and 5 and thin layer chromatography (silica gel plates) using three separate solvent systems showed only one spot detectable under UV light at short wavelength after reaction with phenazine methosulfate reagents.

Elemental analysis: Calc. for $C_{25}H_{27}N_2SNaO_5 \cdot 2H_2O$; Calc.: C=57.02; H=5.93; N=5.32; S=6.09; Found: C=56.37; H=5.59; N=5.30; S=5.99.

EXAMPLE 210

Preparation of the potassium salt of N-alpha[3-(N-alpha-benzoyl-D,L-phenylalanylthio)-2-D-methylpropanoyl]-L-proline The potassium salt of the named compound was prepared by following the procedure of Example 209 using 1M $KHCO_3$ in place of the 1M $NaHCO_3$. Recrystallization yielded 70 mg of a white solid having a decomposition point of 132°–134° C. Infrared analysis, paper electrophoresis, and thin layer chromatography yielded values identical to those of the correspondig sodium salt from Example 209.

EXAMPLE 211

Preparation of the L-lysine salt of N-alpha[3-(N-alpha-benzoyl-D,L-phenylalanylthio-2-D-methylpropanoyl]-L-proline A solution of 73.1 mg (0.5 mmole) of L-lysine free base in 0.3 ml of deionized water was added dropwise, with stirring, to a solution of 234.3 mg (0.5 mmole) of N-alpha[3-(N-alpha-benzoyl-D,L-phenylalanylthio)-2-D-methylpropanoyl]-L-proline in 1 ml of absolute alcohol. Solvents were removed with a rotary evaporator to yield a white residue. Fresh absolute alcohol was added and again solvent was removed with a rotary evaporator. The procedure was repeated two more times with absolute alcohol and then twice with benzene. The final yield was 0.292 g (dp 152°–154.4° C.) after drying in a vacuum desiccator over $P_2O_5$. Recrystallization from absolute alcohol, a few drops of water and benzene gave a yield of 141 mg of a white precipitate having a decomposition point of 162.5°–163.5° C. (softened at 160° C.). Infrared analysis using a KBr pellet showed zwitterion bands at 1389 and 1620 $cm^{-1}$, carbonyl of amide band at 1641 $cm^{-1}$ and a thio ester band at 1678 $cm^{-1}$. Paper electrophoresis at pH 5 and thin layer chromatography (silica gel plates) using three separate solvent systems showed the presence of both the named compound and lysine.

Additional physiologically acceptable salts can be prepared by substituting the appropriate base for the $NaHCO_3$, $KHCO_3$ or lysine in Exaples 209–211 and substantially following the procedures described. Although Examples 209–211 describe the preparation of the salts of the compound N-alpha[3-(N-alpha-benzoyl-D,L-phenylalanylthio)-2-D-methylpropanoyl]-L-proline, it will be understood that physiologically acceptable salts of any compound described by $R_1$-$A_1$-S-Z can be prepared in the same general manner.

EXAMPLE 212 a. Preparation of 3-Acetylthiopropanoic acid 3-mercaptopropanoic acid was vacuum distilled under 1 mm Hg pressure. The fraction boiling between 94° C.–95° C. was collected. The reaction mixture was prepared by adding 105 g of $KHCO_3$ and 50 ml of water together with 100 ml of ether, cooling the mixture in an ice bath to 0° C.–5° C. with vigorous stirring. Approximately 50 mmoles 3-mercaptopropanoic acid was added. Acetic anhydride, 47 ml (0.5 mmoles) was added dropwise over a period of one-half hour following which the reaction mixture was maintained at 0° C.–5° C. for another one-half hour. The reaction mixture was then slowly warmed to room temperature with stirring for one hour and ooled in an ice bath, after which 95 ml of concentrated HCl was added slowly. The mixture was extracted four times with 50 ml portions of ethyl ether. The collected ether phase was washed twice with a small amount of water and twice with saturated NaCl, then dried over anhydrous $MgSO_4$. Solvent was then removed with a rotary evaporator under high vacuum at 35° C. White crystals resulted which were purified by recrystallization from ethanol and n-hexane. The purified white crystalline material had a melting point of 50° C.–51.5° C. Infrared analysis in chloroform revealed an absorption band at 1135 $cm^{-1}$, indicative of the thiolester group, and carbonyl bands at 1690 and 1715 cm$^{-1}$. The product migrated as a single substance in thin layer chromatography in three solvent systems.

b. Preparation of 3-acetylthiopropanoyl-L-proline-t-butyl ester

The product of step a, 3-acetylthiopropanoic acid, 0.865 g, was dissolved in 2 ml redistilled THF and cooled to 0° C. A cooled solution of dicyclohexylcarbodiimide, 1.2031 g in 2 ml of THF was added, following which a cooled solution of L-proline-t-butyl ester, 1 g, was added. The reaction mixture was stored at 0° C. for one hour, then at 4° C. overnight. The reaction mixture was then filtered and the precipitate was washed with ethyl acetate. Solvents of the filtrates were removed under reduced pressure in a rotary evaporator. The residue was dissolved in ethyl acetate which was then washed three times with cold 1N citric acid, twice with saturated NaCl, twice with cold 1N HaHCO3 and three times with saturated NaCl. The solution was dried over anhydrous MgSO4 and filtered. The solvent was removed under reduced pressure in a rotary evaporator at 30° C. yielding a white clear oily product in approximately 87% yield. The product migrated as a single spot in thin layer chromatography in five solvent systems.

c. Synthesis of 3-mercaptopropanoyl-L-proline-t-butyl ester

The product from step b, 3-acetylthiopropanoyl-L-proline-t-butyl ester, 0.5 g, was mixed with 4.5 ml of 5.5N methanolic ammonia at room temperature under nitrogen for one hour. The solvent was then removed at 25° C. with a rotary evaporator. After the product was taken up in methanol and reevaporated twice more in the rotary evaporator, the clear oily residue was dissolved in ethyl ether, washed twice with 5% potassium bisulphate and once with saturated NaCl, dried over MgSO4 and filtered. Residual solvent was removed in vacuo to yield a clear oily product, migrating as a single spot on thin layer chromatography in three separate solvent systems.

d. Preparation of N-(3-benzoylphenylalanylthiopropanoyl)-L-proline-t-butyl ester The oily product from step d, 3-mercaptopropanoyl-L-proline-t-butyl ester was mixed with 254 mg of 1-Hydroxybenzotriazole (HOBt) and 1 ml of redistilled DMF in an ice bath at 0° C. A solution of 608 mg of N-Benzoyl-Phenylalanyl-N-hydroxy-succinimide ester in 2 ml redistilled DMF was added and the mixture was stirred under nitrogen for one hour, then allowed to stand at room temperature for 40 hours. The reaction was terminated with the addition of 25 μl of N,N-dimethyl-1,3-propanediamine. Solvent was removed under high vacuum at 35° C. Ethyl acetate, 50 ml, was added, and the solution was washed twice with saturated NaCl, three times with 1N sodium bicarbonate and three times with saturated NaCl. The solution was then dried over anhydrous magnesium sulphate and filtered. The solvent was removed yielding 0.725 g of a clear gum-like product. The product appeared to be about 90% pure as judged by thin layer chromatography in four solvent systems.

e. Preparation of N-(3-benzoylphenylalanylthiopropanoyl)-L-proline

The product of step e was deprotected by reaction with trifluoracetic acid in anisole. The reaction mixture was incubated at room temperature for one hour, following which trifluoroacetic acid and anisole were removed in vacuo at 32° C. The reaction mixture was then partitioned between saturated NaHCO3 and ethyl acetate in the cold. The bicarbonate phase was washed twice with ethyl acetate and once with ether. Then, in the presence of ethyl acetate, the bicarbonate phase was acidified with HCl, and, after extraction, the ethyl acetate phase was collected and washed with saturated NaCl, dried over anhydrous MgSO4 and filtered. The solvent was removed under reduced pressure. The product was further purified by chromatography on Sephadex G-25, trademark Pharmacia Company, Uppsala, Sweden, using a 1.2 cm×96 cm column eluted with butanol:acetic acid:water, 4:1:5 (volume ratio). Two 20 ml fractions were collected. Most of the product was found in fractions 21 through 23 as determined by positive reaction with O-tolidine/chlorine reagent and with phenazine methosulfate at pH 5.

EXAMPLE 213 a. Preparation of 2-acetylthiopropanoic acid (acetylthiolactic acid

The procedure described in Example 212, step a, was followed except that the starting material was commercial thiolactic acid.

b. Synthesis of N-(2-benzoylphenylalanylthiopropanoyl)-L-proline

Synthesis of this compound was accomplished by essentially the same process as described in Example 212, steps b through e, using 2-acetyl-thiopropanoic acid from step a hereof as starting material.

EXAMPLE 214

Synthesis of N-[3-(benzoylphenylalanylthio)-2-D-methylpropanoyl]-L-proline

A reaction mixture containing 93.3 mg of 2-D-methyl-3-mercaptopropanoyl-L-proline, 62 mg of HOBt, 165 mg of N-benzoylphenylalanyl-N-hydroxy-succinimide ester, prepared as described in Example 5, was cooled in an ice bath at approximately 0° C., after which 0.0544 ml of N-ethyl morpholine was added. The reaction mixture was stirred in an ice bath for three hours, incubated at 4° C. overnight, then at room temperature for twenty hours. The reaction was terminated by the addition of 25 μl of N,N-dimethyl-1,3-propanediamine, and stirred for an additional two hours. Ethyl acetate was added to the reaction mixture which was then washed by extraction with cold 0.1N HCl, followed by two washes with water and three washes with saturated NaCl. The mixture was then dried over anhydrous MgSO4 and filtered. The solvent was removed under reduced pressure in a rotary evaporator, yielding a clear, oily product.

The product was purified by chromatography on a column of Sephadex LH20, 1.2 cm×96 cm. The column was eluted with THF, and 2.5 ml fractions were collected. Fractions 30 and 31 were pooled and yielded, after solvent removal under high vacuum, 110 mg of product. Anhydrous ether was added and a white gum-like material was obtained. The ether was decanted and the white gum-like material was dissolved in THF and transferred to a vial, dried in a stream of nitrogen, then further dried over $P_2O_5$ overnight. A foam-like product, 82 mg, was obtained.

Fractions 29, 32 and 33 were rechromatographed under identical conditions. Fractions 33 through 36 of the second chromatography were pooled, worked up as described and yielded an additional 51 mg of product. Total yield was 71%.

EXAMPLE 215

(a) Synthesis of 2-benzoylphenylalanylthiopropanoic acid

A solution of 2.6935 g of Benzoyl-Phenylalanine in 30 ml of redistilled DMF was cooled to $-20°$ C. A solution of 1,1'-carbonyldiimidazole in 10 ml redistilled DMF was added dropwise with vigorous stirring. Temperature was not allowed to exceed $-14°$ C. Following the addition, the solution was stirred at $-10°$ C. for two hours. D,L-Thiolactic acid, 1.12 g in 5 ml of redistilled DMF previously neutralized with 1.43 ml of redistilled N-ethylmorpholine was then added with continued stirring at $-10°$ C. for one hour. The solution was then slowly warmed to room temperature. About 50 ml ethyl acetate was added. The mixture was then cooled and neutralized with 1 ml of concentrated HCl in approximately 10 ml saturated NaCl. The organic phase was then washed three times with subsaturated NaCl, i.e., 5 ml saturated NaCl diluted with 1 ml water. Occasionally, a three layer system was observed. In such cases, the middle layer was saved and combined with the lower aqueous phase. The organic phase was dried over anhydrous $MgSO_4$, filtered and placed in the rotary evaporator to remove solvent. A small amount of yellowish oil that was not the desired product was recovered. The combined aqueous phase and middle phase were acidified at 0° C. with concentrated HCl to pH 2, and extracted three times with ethyl acetate and the organic phase was washed with saturated NaCl and dried over anhydrous $MgSO_4$, filtered and rotary evaporated. 3.33 g of clear oil was recovered. The material thus recovered was identified by its behavior on thin layer chromatography.

(b) Synthesis of N-(2-benzoylphenylalanylthiopropanyl)-L-proline-t-butyl ester The product of step (a), 933 mg 2-benzoyl-phenylalanylthiopropanoic acid, was dissolved in 3 ml DMF and cooled to 0° C. in an ice-acetone bath. Dicyclohexylcarbodiimide, 536 mg in 1.5 ml DMF, was added and the mixture was stirred 5 minutes at 0° C. 462 mg of L-proline-t-butyl ester in 1.5 ml DMF was added. The reaction mixture was stirred at 4° C. overnight. The reaction mixture was worked up by addition of 10 ml ethyl acetate, filtration and addition of 20 ml ethyl acetate to the filtrate. The combined ethyl acetate fractions were chilled in a freezer, extracted three times with saturated NaCl, once with ice-cold 0.1N HCl, again three times with saturated NaCl, then three times with ice-cold 1N $NaHCO_3$, and three times with saturated NaCl. The organic phase was dried with anhydrous $MgSO_4$ and again filtered. Solvent was removed with a rotary evaporator under high vacuum, yielding 1.16 g of white residue. The product was substantially pure as judged by thin layer chromatography.

(c) Synthesis of N-(2-benzoylphenylalanylthiopropanoyl)-L-proline

The product of step (b), N-(2-benzoylphenylalanyl-thiopropanoyl)-L-proline-t-butyl ester, 1.25 g, was suspended in 4 ml anisole and reacted with 8 ml trifluoroacetic acid for 1 hour at room temperature with stirring. In view of the fact that some starting material was later recovered, the reaction time should be increased. Trifluoroacetic acid was removed with a rotary evaporator under high vacuum. The residue was dissolved in 1 ml THF and chromatographed on a 2.2 cm×99 cm column of Sephadex LH-20 eluted with THF. Fractions of about 5.3 ml were collected. The product was eluted in fractions 41–43. The combined fractions 41–43 were evaporated to dryness, dissolved in a small amount of isopropanol and rechromatographed on a 1.2 cm×95 cm LH-20 column, eluted with isopropanol. Fractions of about 2.05 ml were collected. Fractions 48–50 contained 78 mg of the desired compound as an oil. Side fractions 46–47 and 51–53 were saved for rechromatography. The oil was dissolved in a small volume of THF in a vial, then the THF was evaporated under a stream of $N_2$. The vial was then placed in a round bottom flask connected to a rotary evaporator. After 3 hours under high vacuum, a stable, dry foam was obtained.

Identification of thiol ester compounds

In many of the foregoing examples, reaction products were separated by thin layer chromatography. The thiol ester compounds were identified using chlorine/o-tolidine reagent which gives a cream colored spot. Compounds containing free sulfhydryl groups react with phenazine methosulfate to yield a reddish-orange color at room temperature. See *Anal. Biochem.*, 79, 610 (1977). The thiol ester compounds require heating at 80° C. for 5–10 minutes to yield an orange color. Some solvent systems, for example, benzene/acetic acid/-$H_2O$, 9:9:1, reduce color development of the thiol ester compounds.

The ensuing examples describe tests conducted with the compounds R, -A, -S, -Z in vivo and in vitro.

EXAMPLE 216

A. ACE activity assay. For most experiments described herein, the enzyme ACE was assayed in 0.05M Hepes buffer, pH 8.0 containing 0.1M NaCl and 0.75M $Na_2SO_4$. The substrate employed was Benzoyl-GlyHis-Leu at a final concentration of $1\times10^{-4}M$, together with about 130,000 cpm of [$^3$H]-Benzoyl GlyHisLeu (25 Ci/mmole). Enzyme was diluted in the above buffer such that 40 μl buffered enzyme was capable of hydrolyzing 13% of substrate in a 15-minute incubation at 37° C. To initiate the assay, 40 μl of enzyme and 10 μl of water or inhibitor dissoved in water were preincubated for five minutes at 37° C. Substrate, 50 μl, was then added to initiate reaction and the solution was incubated for 15 minutes at 37° C. To terminate the reaction, 1 ml of 0.1M HCl was added, following which 1 ml of ethyl acetate was added. The mixture was agitated on a rotary mixer and centrifuged briefly to separate the phases.

An aliquot, 500 μl, of the ethyl acetate layer was transferred to a liquid scintillation vial containing 10 ml of Riafluor, trademark New England Nuclear Corporation, Boston, Mass. For determination of $I_{50}$ values, enzyme activity in the presence of inhibitor at a series of different concentrations was compared to activity in the absence of inhibitor. A plot of inhibitor concentration versus percent inhibition yielded the $I_{50}$ value.

B. In certain experiments, as identified, an alternative assay system was employed using [$^3$H]-HipGlyGly as substrate as described by Ryan, J. W., et al., *Biochem. J.* 167 501 (1977).

EXAMPLE 217

Using the assay system of Example 216A, a series of peptide substrates or substrate analogs was tested for inhibitor potency. Results are given in Table 12.

TABLE 12

| Compound | $I_{50}$* |
|---|---|
| L-proline | $1 \times 10^{-3}$ M |
| Ala—ro | $1 \times 10^{-5}$ M |
| benzoyl-Phe | $4 \times 10^{-4}$ M |
| Phe—Ala—Pro | $2 \times 10^{-7}$ M |
| benzoyl-Phe—Ala—Pro | $1 \times 10^{-7}$ M |

The results illustrate the importance of providing recognition groups on both sides of any substrate bond to be hydrolyzed by ACE.

A series of peptides and analogs in which L-cysteine was incorporated as the penultimate amino acid was tested for inhibitory effectiveness. Results are shown in Table 13.

TABLE 13

| Compound | $I_{50}$* |
|---|---|
| L-cysteine | $2 \times 10^{-4}$ M |
| Cys—Pro | $1.1 \times 10^{-5}$ M |
| γ Glu—Cys—Pro | $1.1 \times 10^{-5}$ M |
| γ Glu—Cys—Gly (glutathione) | $4 \times 10^{-5}$ M |
| acetyl-Cys—Pro | $5 \times 10^{-6}$ M |
| < Glu—Cys—Pro | $4 \times 10^{-6}$ M |
| benzoyl-Phe—Cys—Pro | $6 \times 10^{-7}$ M |
| benzoyl-Gly—Cys—Pro | $5 \times 10^{-7}$ M |

These data provide support for the conclusion that a free sulfhydryl group is not essential for inhibitory potency when the inhibitor, or competitive substrate, is tightly bound to the active site of the enzyme.

EXAMPLE 218

Preparation of ACE from guinea pig or human urine

Fresh urine was ultrafiltered using a membrane (PTGC 142 05, Millipore Corp., Bedford, MA, U.S.A.) with a 10,000 MW retention limit. Typically, 500 ml of urine was ultrafiltered to approx. 15 ml and then the concentrated proteins were washed with water and then applied to a column (2.5×110 cm) of Sephacryl S-200, Trademark, Pharmacia Chemical Co., Uppsala, Sweden, previously equilibrated with 0.05M TrisHCl buffer, pH 8.0, with 0.5M NaCl. Under these conditions, ACE was eluted in two peaks; one, the major peak, was eluted just after the void volume ($V_e/V_o=1.21$) and the second (up to 20% of the total activity) at $V_e/V_o=1.41$. Enzyme activity was measured using [$^3$H]-HipGlyGly as described in Example 1B. Activities of both peaks were inhibited completely by SQ 14,225 at 0.1 μM. The activities were inhibited to a maximum of 84% by antibody to guinea pig lung ACE. The enzyme used herein was that of the first peak to emerge from the Sepacryl column. The enzyme preparation was concentrated about 10-fold by ultrafiltration. In one such experiment, the concentrated urinary protein solution obtained by ultrafiltration contained 2,400 m units of enzyme at 8.0 m units/mg of protein, and peak 1 from the Sephacryl column contained 1,100 m units at 814 m units/mg of protein. Disc gel electrophoresis, at pH 9.0, of 28 μg of the final preparation showed four bands after staining with Coomassie blue. One band ($R_f=0.21$ in respect to bromphenol blue) corresponded to ACE.

EXAMPLE 219

The inhibitory potency of the compounds 2-benzoylphenylalanylthio-2-D-methylpropanoyl-L-proline (I), 2-benzoylphenylalanylthiopropanoyl-L-proline (II) and 3-benzoylphenylalanylthio-propanoyl-L-proline (III) was measured in vitro in the assay system described in Example 216A. Results are shown in Table 14.

TABLE 14

| Compound | $I_{50}$ |
|---|---|
| SQ 14,225 | $3 \times 10^{-8}$ M |
| (I) | $4 \times 10^{-8}$ M |
| (I) | $1 \times 10^{-8}$ M |
| racemic (II) | $7 \times 10^{-8}$ M |
| racemic (II) | $4 \times 10^{-8}$ M |
| (III) | $7 \times 10^{-7}$ M |

In view of the high degree of inhibitory potency exhibited by compound (II), it would appear that stereospecificity in the region of the thiopropanoyl analog is less critical than previously thought.

Thioester compounds (I), (II) and (III) have been found to be surprisingly resistant to alkaline hydrolysis. Compound (I) is not hydrolyzed at pH 9.5 in 1M NaHCO$_3$. Therefore the observed inhibitory effects cannot be accounted for by postulating spontaneous hydrolysis of the thioester bond to regenerate the free sulfhydryl group.

EXAMPLE 220

Oral effectiveness

Female Sprague-Dawley rats, approximately 250 g weight, were fasted overnight and then administered either 0.5 ml of saline, via stomach tube, or 0.5 ml saline containing compound (I) at a dose of 1 mg per kg of body weight. At timed intervals the rats were beheaded using a guillotine and 3 ml-5 ml blood was collected. The sera were assayed for intrinsic ACE activity, using the assay of Example 216B. The results of duplicate runs are shown in Table 15.

TABLE 15

| Time (minutes after drug administration) | ACE activity (Percent of Control) Serum | |
|---|---|---|
| 5 | 100 | 100 |
| 10 | 65 | 52 |
| 30 | 50 | 45 |
| 60 | 50 | 42 |
| 90 | 20 | 20 |

The results indicate a substantial and consistent degree of oral effectiveness for compound (I).

EXAMPLE 221

Oral effectiveness of (I)

Young, unanesthetized rabbits, fasted overnight, weighing about 1 kg, were given compound (I). The compound was dissolved in water at alkaline pH, 1 mg of (I) in 3 ml water containing 50 μl 1N NaHCO$_3$. Blood samples, 0.5 ml, were collected at timed intervals from a marginal ear vein. Sera obtained after clot formation and centrifugation were assayed for intrinsic ACE activity, using 1 μl in the assay of Example 216A. Results are shown in Table 16.

TABLE 16

| Time after administration (hours) | Serum ACE activity Percent of Control | |
|---|---|---|
| | Rabbit 1 | Rabbit 2 |
| −0.1 (control) | 100 | 100 |
| 0.167 | 7 | 11 |
| 0.33 | 8 | 9 |
| 0.5 | 7 | 8 |
| 1.0 | 20 | 44 |
| 1.5 | 14 | 55 |
| 2.0 | 11 | 44 |
| 2.5 | 12 | 40 |
| 3.0 | 30 | — |
| 4.0 | 23 | — |
| 5.0 | 19 | — |
| 20.0 | 70 | — |

The compound was therefore highly effective in duplicate trials. In addition, the long-term effectiveness suggests that compound (I) is relatively stable in vivo, a desirable property for an anti-hypertensive therapeutic agent.

EXAMPLE 222

Oral effectiveness of (I)

Rats (210-290 g body weight) were fasted overnight and then anesthetized with intraperitoneal pentobarbital, 50-60 mg/kg. Tracheostomy was performed and the animals were ventilated mechanically. A cannula was inserted into a femoral vein for injection of angiotensin I or II, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 80 ng of angiotensin I or angiotensin II in 20 μl of 0.9 g % NaCl; an amount of antiotensin I or II sufficient to raise mean arterial blood pressure by 27-40 mm Hg. After the responsiveness of a given rat to angiotensins I and II was established, compound (I), at 2 or 5 mg/kg (drug dissolved in 0.5 ml of H₂O plus 10 μl of 1N NaHCO₃), was given via a stomach tube. At timed intervals, the effects of 80 ng of angiotensin I or angiotensin II on mean arterial blood pressure were tested. Results are shown in Table 17.

TABLE 17

| Time After Oral Administration of (I) (minutes) | Blood Pressure Response to 80 ng of Angiotensin I | | |
|---|---|---|---|
| | Drug at 5 mg/kg | | Drug at 2 mg/kg |
| | Rat 1 | Rat 2 | Rat 3 |
| | (values in % of control) | | |
| −6 | 100% | 100% | 100% |
| +6 | — | 67 | 111 |
| 12 | 41 | 57 | 93 |
| 18 | 36 | — | 81 |
| 24 | — | 43 | 85 |
| 35 | 23 | 37 | 56 |
| 48 | 18 | 17 | — |
| 58 | 23 | 17 | 56 |
| 68 | — | 20 | 52 |
| 78 | — | 17 | — |
| 88 | — | 13 | 30 |
| 118 | 23% | — | 37 |
| 138 | | — | 60 |
| 148 | | — | — |
| 169 | | — | 37 |
| 185 | | 27 | 37 |

TABLE 17-continued

| Time After Oral Administration of (I) (minutes) | Blood Pressure Response to 80 ng of Angiotensin I | | |
|---|---|---|---|
| | Drug at 5 mg/kg | | Drug at 2 mg/kg |
| | Rat 1 | Rat 2 | Rat 3 |
| | (values in % of control) | | |
| 205 | | 33 | 44% |
| 213 | | 33 | |
| 226 | | 43% | |

Compound (I) was highly effective in inhibiting the pressor effects of angiotensin I even in rats anesthetized with pentobarbital, a substance which decreases gastrointestinal motility and which may interfere with gastrointestinal absorption. For a discussion of the pharmacological effects of barbiturates, see Goodman, L. S. and Gilman, A., *The Pharmacological Basis of Therapeutics*, The Macmillan Co., New York, 1965, pp. 105–128. In addition, a graded doseresponse is evident: Compound (I) at 5 mg/kg is clearly more effective than compound (I) at 2 mg/kg. At either dosage, the duration of drug action was long (>226 minutes), a desirable property for a compound to be used to confer therapeutic benefit in hypertensive cardiovascular disease.

The effects of compound (I) were specific. The pressor effects of angiotensin I were inhibited by compound (I) but the effects of angiotensin II were not inhibited. As is well-known, angiotensin I does not raise arterial blood pressure without first being converted to angiotensin II (as through the action of angiotensin converting enzyme).

EXAMPLE 223

Oral effectiveness of (II)

Rats were prepared as described in Example 222. Compound (II) [N-benzoyl-L-phenylalanylthiopropanoyl)-L-proline] was given orally, via a stomach tube, at a dose of 12 mg/kg or 20 mg/kg. Compound (II) was dissolved in 0.5 ml of H₂O plus 10 μl of 1N NaHCO₃. In all other respects, the experimental preparations were exactly as described in Example 222. Results are shown in Table 18.

TABLE 18

| Time After Oral Administration of (II) (minutes) | Blood Pressure Response (% of control) to 80 ng of Angiotensin I | |
|---|---|---|
| | Drug at 12 mg/kg Rat 1 | Drug at 20 mg/kg Rat 2 |
| −8 | 100% | 100% |
| +6 | 109 | 91 |
| 12 | 80 | 70 |
| 23 | — | 76 |
| 30 | 51 | 76 |
| 38 | — | — |
| 47 | 71 | — |
| 56 | 69 | 55 |
| 76 | 63 | 40 |
| 95 | — | 40 |
| 101 | — | — |
| 142 | — | 76 |
| 150 | 49 | — |
| 158 | 57% | 76 |
| 166 | | 76 |
| 176 | | 76% |
| 184 | | |

Thus, in addition to compound (I), compound (II) is also effective when given orally in sufficient dosage. Compound (II) is also specific. It inhibited the pressor effects of angiotensin I but did not inhibit the pressor effects of angiotensin II.

EXAMPLE 224

The inhibitory potency of N-(2-benzoylphenylalanyl-tiopropanoyl)-L-3,4-dehydroproline (B) in vitro was measured in the assay system described in Example 216A. The enzyme preparation was ACE purified from human urine as described by Ryan, J. W., et al, *Tissue and Cell* 10, 555 (1978). Result is shown in Table 19.

TABLE 19

| Compound | $I_{50}$ |
|---|---|
| B (racemic) | $3 \times 10^{-9}$ M |

EXAMPLE 225

Oral effectiveness of compound (B)

Rats (210–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I or II, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 160 ng of angiotensin I or 80 ng of angiotensin II in 20 µl of 0.9 g % NaCl; an amount of angiotensin I or II sufficient to raise mean arterial blood pressure by 27–40 mm Hg. After the responsiveness of a given rat to angiotensins I and II was established, compound (B) at 10 mg (drug dissolved in 0.5 ml of H$_2$O plus 10 µl of 1N NaHCO$_3$), was given via a stomach tube. At timed intervals, the effects of 160 ng of angiotensin I or 80 ng of angiotensin II on mean arterial blood pressure were tested. Results are shown below:

| Oral effectiveness of N—(2-benzoylphenylalanylthio-propanoyl)-L-3,4-dehydroproline (B). | |
|---|---|
| Time After Oral Administration (Minutes) | Blood Pressure Response to 160 mg of Angiotensin I Drug at 10 mg |
| −5 | 100% (27 mmHg) |
| +3 | 100 |
| 9 | 81 |
| 14 | 74 |
| 24 | 74 |
| 28 | 74 |
| 34 | 63 |
| 44 | 56 |
| 54 | 44 |
| 64 | 56 |
| 85 | 37 |
| 94 | 44 |
| 104 | 74 |
| 114 | 56 |
| 146 | 100% |

EXAMPLE 226

The inhibitory potency of the Example 196 and 197 compounds in vitro was measured in the assay system described in Example 216A. The enzyme preparation was purified from human urine as described by Ryan, J. W., et al, *Tissue and Cell* 10, 555 (1978). Table 20 shows the $I_{50}$ value for various compounds. The $I_{50}$ value is the concentration of inhibitor required to produce 50% inhibition of the enzyme under a standard assay system containing substrate at a level substantially below K$_m$.

TABLE 20

| Compound | $I_{50}$ |
|---|---|
| Example 196 | $1.6 \times 10^{-8}$ M |
| Example 197 | $9 \times 10^{-9}$ M |

EXAMPLE 227

The inhibitory potency of N-alpha-[3-(N-alpha-Cpc-N-epsilon-Boc-L-Lys-L-Phe-thio)-2-D-methylpropanoyl]-L-proline (A) and N-alpha-[3-(N-alpha-Cpc-L-Lys-L-Phe-thio)-2-D-methylpropanoyl]-L-proline (B) in vitro were measured in the assay described in Example 216A. The enzyme preparation was ACE purified from human urine as described by Ryan, J. W., et al, *Tissue and Cell* 10, 555 (1978). The $I_{50}$ for (A) was found to be $2.5 \times 10^{-8}$M and for (B), $1.5 \times 10^{-8}$M.

EXAMPLE 228

Oral effectiveness of N-alpha-[3-(N-alpha-cyclopentylcarbonyl-L-lysyl-L-phenylalanylthio)-2-D-methylpropanoyl]-L-proline Rats (210–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/kg of angiotensin I in 20 µl of 0.9 g % NaCl; an amount of angiotensin I sufficient to raise mean arterial blood pressure by 39 mm Hg. After the responsiveness of a given rat to angiotensin I was established, the named compound at 17 µmol/kg (drug dissolved in 0.15 ml of H$_2$O plus 10 µl of 1N NaHCO$_3$), was given via a stomach tube. At timed intervals, the effects of 400 ng/kg of angiotensin I on mean arterial blood pressure were tested. Results are shown below:

| Time After Oral Administration (minutes) | Blood Pressure Response to 400 ng/kg of Angiotensin I (% of Control) |
|---|---|
| −5 | 100 (39 mm Hg) |
| +5 | 59 |
| 10 | 44 |
| 15 | 44 |
| 31 | 44 |
| 37 | 38 |
| 45 | 44 |
| 55 | 44 |
| 81 | 36 |
| 93 | 36 |
| 104 | 38 |

EXAMPLE 229

Intravenous Effectiveness of N-alpha-[3-(N-alpha-cyclopentylcarbonyl-L-lysyl-phenylalanylthio)-2-D-methylpropanoyl]-L-proline Anesthetized rats were prepared as described in Example 228. After the responsiveness of a given rat to angiotensin I was established, the named compound at 2

μmol/kg, in a volume of 15 μl of 0.01N sodium bicarbonate, was injected via a femoral vein. At timed intervals, the effects of angiotensin I, 400 ng/kg, on mean arterial blood pressure were tested. Results are shown below:

| Time After Oral Administration (minutes) | Blood Pressure Response to 400 ng/kg of Angiotensin I (% of Control) |
|---|---|
| −5 | 100 (39 mm Hg) |
| +3 | 8 |
| 9 | 15 |
| 14 | 23 |
| 19 | 23 |
| 24 | 33 |
| 37 | 41 |
| 45 | 46 |
| 54 | 46 |
| 77 | 46 |
| 87 | 51 |

EXAMPLE 230

The inhibitory potency of N-alpha-[3-(N-alpha-Boc-L-Phe-thio)-2-D-methylpropanoyl]-L-proline (A) and N-alpha-[3-(N-alpha-Cpc-L-Phe-thio)-2-D-methylpropanoyl]-L-proline (B) in vitro was measured in the assay system described in Example 216A. The enzyme preparation was ACE purified from human urine as described by Ryan, J. W., et al, *Tissue and Cell* 110, 555 (1978). The $I_{50}$ for (A) was found to be $3.4 \times 10^{-8}$M and for (B), $7.5 \times 10^{-9}$M.

EXAMPLE 231

Oral effectiveness of N-alpha-[3-(N-alpha-cyclopentylcarbonyl-L-phenylalanylthio)-2-D-methylpropanoyl]-L-proline Rats (190–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angtiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/kg of angiotensin I in 20 μl of 0.9 g % NaCl; an amount of angiotensin I sufficient to raise mean arterial blood pressure by 35 mm Hg. After the responsiveness of a given rat to angiotensin I was established, the named compound at 23 μmole/kg (drug dissolved in 0.15 ml of H₂O plus 10 μl of 1N NaHCO₃), was given via a stomach tube. At timed intervals, the effects of 400 ng/kg of angiotensin I on mean arterial blood. pressure were tested. Results are shown below:

| Time After Oral Administration (minutes) | Blood Pressure Response to 400 ng/kg of Angiotensin I (% of Control) |
|---|---|
| −5 | 100 (35 mm Hg) |
| +2 | 71 |
| 6 | 63 |
| 16 | 49 |
| 23 | 43 |
| 37 | 43 |
| 48 | 40 |
| 64 | 26 |
| 71 | 26 |
| 84 | 37 |
| 96 | 37 |
| 109 | 40 |
| 124 | 54 |
| 140 | 51 |
| 157 | 63 |
| 171 | 77 |

EXAMPLE 232

Intravenous effectiveness of N-alpha-[3-(N-alpha-tert-butyloxycarbonyl-L-phenylalanylthio)-2-D-methylpropanoyl]-L-proline Anesthetized rats were prepared as described in Example 231. After the responsiveness of a given rat to angiotensin I was established, the named compound, at 2 μmol/kg, in a volume of 15 μl of 0.01N sodium bicarbonate, was injected via a femoral vein. At timed intervals, the effects of angiotensin I, 400 ng/kg, on mean arterial blood pressure were tested. Results are shown below:

| Time After Intravenous Administration (minutes) | Blood Pressure Response to 400 ng/kg Angiotensin I (% of Control) |
|---|---|
| −5 | 100 (32 mm Hg) |
| +0.5 | 0 |
| 3 | 19 |
| 9 | 19 |
| 13 | 22 |
| 18 | 31 |
| 22 | 31 |
| 34 | 50 |
| 47 | 63 |
| 65 | 78 |
| 103 | 75 |
| 113 | 94 |

EXAMPLE 233

Oral effectiveness of N-alpha-[3-(N-alpha-tert-butyloxycarbonyl-L-phenylalanylthio)-2-D-methylpropanoyl]-L-proline The procedure of Example 231 was followed. The angiotensin I response was 37 mm Hg and the oral dose administered was 20 μmol/kg. Results are shown below:

| Time After Oral Administration (minutes) | Blood Pressure Response to 400 ng/kg of Angiotensin I (% of Control) |
|---|---|
| −5 | 100 (37 mm Hg) |
| +3 | 100 |
| 11 | 43 |
| 22 | 27 |
| 29 | 24 |
| 34 | 22 |
| 51 | 19 |

EXAMPLE 234

The inhibitory potency of N-alpha-[3-(N-alpha-acetyl-L-phenylalanylthio)-2-D-methylpropanoyl]-L-proline in vitro was measured in the assay system described in Example 216A. The enzyme preparation was ACE purified from human urine as described by Ryan, J. W., et al, Tissue and Cell 10, 555 (1978). The $I_{50}$ was found to be $2.6 \times 10^{-8}$ M.

EXAMPLE 235

Oral effectiveness of N-alpha-[3-(N-alpha-acetyl-L-phenylalanylthio)-2-D-methylpropanoyl]-L-proline Rats (210–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/kg of angiotensin I in 20 μl of 0.9 g % NaCl; an amount of angiotensin I sufficient to raise mean arterial blood pressure by 50 mm Hg. After the responsiveness of a given rat to angiotensin I was established, the named compound at 13.6 μmole/kg (drug dissolved in 0.15 ml of $H_2O$ plus 10 μl of 1N $NaHCO_3$), was given via a stomach tube. At timed intervals, the effects of 400 ng/kg of angiotensin I on mean arterial blood pressure were tested. Results are shown below:

| Time After Oral Administration (minutes) | Blood Pressure Response to 400 ng/kg of Angiotensin I (% of Control) |
| --- | --- |
| −5 | 100 (50 mm Hg) |
| +3 | 40 |
| 7 | 40 |
| 13 | 28 |
| 18 | 24 |
| 23 | 20 |
| 31 | 18 |
| 34 | 20 |
| 42 | 20 |
| 48 | 16 |
| 58 | 16 |
| 67 | 20 |
| 80 | 20 |
| 90 | 18 |
| 100 | 16 |
| 112 | 20 |
| 125 | 20 |
| 137 | 30 |
| 167 | 50 |

EXAMPLE 236

The inhibitory potency of N-alpha-(3-phenylalanylthio-2-D-methylpropanoyl)-L-proline in vitro was measured in the assay described in Example 216A. The enzyme preparation was ACE purified from human urine as described by Ryan, J. W., et al, Tissue and Cell 10, 555 (1978). The $I_{50}$ was found to be $8.8 \times 10^{-9}$ M.

EXAMPLE 237

Oral effectiveness of N-alpha-(3-phenylalanylthio-2-D-methylpropanoyl)-L-proline Rats (210–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/ml of angiotensin I in 20 μl of 0.9 g % NaCl; an amount of angiotensin I sufficient to raise mean arterial blood pressure by 37 mm Hg. After the responsiveness of a given rat to angiotensin I was established, the named compound at 20 μmol/kg (drug dissolved in 0.15 ml of $H_2O$ plus 10 μl of 1N $NaHCO_3$), was given via a stomach tube. At timed intervals, the effects of 400 ng/kg of angiotensin I or on mean arterial blood pressure were tested. Results are shown below:

| Time After Oral Administration (minutes) | Blood Pressure Response to 400 ng/kg of Angiotensin I (% of Control) |
| --- | --- |
| −5 | 100 (37 mm Hg) |
| +6 | 77 |
| 10 | 69 |
| 19 | 46 |
| 25 | 38 |
| 29 | 38 |
| 38 | 33 |
| 50 | 33 |
| 57 | 31 |
| 65 | 31 |
| 74 | 26 |
| 88 | 36 |

EXAMPLE 238

The inhibitory potency of N-alpha-[3-(N-alpha-benzoylglycylthio)-2-D-methylpropanoyl]-L-proline in vitro was measured in the assay described in Example 216A. The enzyme preparation was ACE purified from human urine as described by Ryan, J. W., et al, Tissue and Cell 10, 555 (1978). The $I_{50}$ was found to be $7.5 \times 10^{-9}$ M.

EXAMPLE 239

Oral effectiveness of N-alpha-[3-(N-alpha-benzoylglycylthio)-2-D-methylpropanoyl]-L-proline Rats (210–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/ml of angiotensin I in 20 μl of 0.9 g % NaCl; an amount of angiotensin I sufficient to raise means arterial blood pressure by 38 mm Hg. After the responsiveness of a given rat to angiotensin I was established, the named compound at 20 μmol)kg (drug dissolved in 0.15 ml of $H_2O$ plus 10 μl of 1N $NaHCO_3$), was given via a stomach tube. At timed intervals, the effects of 400 ng/kg of angiotensin I on mean arterial blood pressure were tested. Results are shown below:

| Time After Oral Administration (minutes) | Blood Pressure Response to 400 ng/kg of Angiotensin I (% of Control) |
| --- | --- |
| −5 | 100 (38 mm Hg) |
| +1 | 95 |
| 6 | 95 |
| 11 | 95 |
| 22 | 92 |
| 28 | 68 |
| 33 | 61 |
| 39 | 58 |
| 45 | 47 |
| 60 | 47 |
| 67 | 45 |
| 74 | 47 |
| 82 | 47 |
| 92 | 47 |
| 137 | 55 |
| 142 | 55 |
| 152 | 47 |
| 185 | 63 |
| 207 | 79 |
| 230 | 74 |

EXAMPLE 240

Intravenous Effectiveness of N-alpha-[3-(N-alpha-benzoylglycylthio)-2-D-methylpropanoyl]-L-proline Anesthetized rats were prepared as described in Example 239. The animals were administered the named compound via a femoral vein in 15 µl of 0.01N sodium bicarbonate, after the control response to 400 ng/kg of angiotensin I was measured. Intravenous administration of the named compound resulted in a rapid decrease of blood pressure response to angiotensin I, 400 ng/kg, follwed by a gradual rise to the pretreatment level of responsiveness. The time required for recovery of one half of the lost responsiveness to angiotensin I, following injection of the named compound, was designated t½. For example, given the control response of 38 mm Hg, an initial decrease of 19 mm would constitute a reduction to 50% of the control response, and t½ would be the time required for the mean arterial blood pressure response to angiotensin I to reach 28.5 mm (75% of control). Results are shown for two dose levels:

| Dose | t½ (minutes) |
| --- | --- |
| 0.23 µmol/kg | 26 |
| 0.7 µmol/kg | 36 |

EXAMPLE 241

The inhibitory potency of [3-(N-alpha-benzoyl-L-tryptophylthio)-2-D-methylpropanoyl]-L-proline in vitro was measured in the assay described in Example 216A. The enzyme preparation was ACE purified from human urine as described by Ryan, J. W., et al, *Tissue and Cell* 10, 555 (1978). The $I_{50}$ was found to be $9.4 \times 10^{-9}$M.

EXAMPLE 242

Oral effectiveness of N-alpha-[3-(N-alpha-benzoyl-L-tryptopylthio)-2-D-methylpropanoyl]-L-proline Rats (210–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/ml of angiotensin I sufficient to raise mean arterial blood pressure by 25 mm Hg. After the responsiveness of a given rat to angiotensin I was established, the named compound at 20 µmol/kg (drug dissolved in 0.15 ml of $H_2O$ plus 10 µl of 1N $NaHCO_3$), was given via a stomach tube. At timed intervals, the effects of 400 ng/kg of angiotensin I on mean arterial blood pressure were tested. Results are shown below:

| Time After Oral Administration (minutes) | Blood Pressure Response to 400 ng/kg of Angiotensin I (% of Control) |
| --- | --- |
| −5 | 100 (25 mm Hg) |
| +3 | 92 |
| 7 | 64 |
| 21 | 32 |
| 26 | 40 |
| 32 | 40 |
| 38 | 20 |
| 50 | 8 |
| 56 | 8 |
| 70 | 8 |
| 79 | 20 |
| 87 | 12 |
| 104 | 12 |
| 114 | 20 |
| 124 | 40 |
| 136 | 40 |
| 148 | 36 |
| 173 | 48 |
| 186 | 48 |
| 199 | 68 |
| 212 | 64 |
| 226 | 64 |
| 242 | 80 |
| 260 | 80 |
| 291 | 84 |

EXAMPLE 243

Intravenous effectiveness of N-alpha-[3-(N-benzoyl-L-tryptophylthio-2-D-methylpropanoyl]-L-proline Anesthetized rats were prepared as described in Example 242. The named compound was administered intravenously via a femoral vein, at the stated dose, in 15 µl of 0.01N sodium bicarbonate. The response to intravenous administration was a rapid decrease in responsiveness to Angtiotensin I, 400 ng/kg, followed by a gradual recovery to the pretreatment level of responsiveness. The time required for recovery of one half the lost responsiveness to angiotensin I, following injection of the named compound, is designated t½. For example, given the control response of 35 mm Hg, an initial decrease of 17.5 mm would constitute a reduction to 50% of control, and t½ would be the time required for the mean arterial blood pressure response to angiotensin I to increase to 26 mm (75% of control). Results are shown for the three dose levels:

| Dose | t½ (minutes) |
| --- | --- |
| 0.193 µmol/kg | 11 |
| 0.58 µmol/kg | 11 |

| Dose | t½ (minutes) |
|---|---|
| 1.93 μmol/kg | 15 |

EXAMPLE 243

The inhibitory potency of N-alpha-[3-(L-alpha-glutamylthio)-2-D-methylpropanoyl]-L-proline in vitro was measured in the following assay. The $I_{50}$ value was found to be $2.1 \times 10^{-9}$M. Human urinary ACE is prepared as described by Ryan, J. W., et al, *Tissue and Cell* 10, 555 (1978). The enzyme was assayed in 0.05M Hepes buffer, pH 8.0 containing 0.1M NaCl and 0.75M $Na_2SO_4$. The substrate employed was hippuryl-His-Leu at a final concentration of $1 \times 10^{-4}$M, (Km=$2 \times 10^{-4}$M), together with about 130,000 cpm of [$^3$H]-hippuryl-His-Leu (25 C:/mmole). Enzyme was diluted in the above buffer such that 40 μl of buffered enzyme was capable of hydrolyzing 13% of substrate in a 15 minute incubation at 37° C. To initiate the assay, 40 μl of enzyme and 10 μl of water or inhibitor dissolved in water were preincubated for five minutes at 37° C. Substrate, 50 μl, was then added to initiate reaction and the solution was incubated for 15 minutes at 37° C. To terminate the reaction, 1 ml of 0.1M HCl was added, following which 1 ml of ethyl acetate was added. The mixture was agitated on a rotary mixer and centrifuged briefly to separate the phases.

An aliquot, 500 μl, of the ethyl acetate layer was transferred to a liquid scintillation vial containing 10 ml of Riafluor, trademark New England Nuclear Corporation, Boston, Mass. For determination of $I_{50}$ values, enzyme activity in the presence of inhibitor at a series of different concentrations was compared to activity in the absence of inhibitor. A plot of inhibitor concentration versus percent inhibition yielded the $I_{50}$ value.

EXAMPLE 244

Oral effectiveness of
N-alpha-[3-(L-alpha-glutamylthio)-2-D-methylpropanoyl]-L-proline Rats (190–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/ml of angiotensin I in 20 μl of 0.9 g % NaCl; an amount of angiotensin I sufficient to raise mean arterial blood pressure by 38 mm Hg. After the responsiveness of a given rat to angiotensin I was established, the named compound at 10 μmol/kg (drug dissolved in 0.15 ml of $H_2O$ plus 10 μl of 1N $NaHCO_3$), was given via a stomach tube. At timed intervals, the effects of 400 ng/kg of angiotensin I on mean arterial blood pressure were tested. Results are shown below:

| Time After Oral Administration (minutes) | Blood Pressure Response to 400 ng/kg of Angiotensin I (% of Control) |
|---|---|
| −5 | 100 (38 mm Hg) |
| +9 | 66 |
| 18 | 39 |
| 26 | 39 |
| 33 | 26 |
| 39 | 18 |
| 45 | 18 |
| 53 | 13 |
| 64 | 13 |
| 77 | 26 |
| 89 | 26 |
| 111 | 24 |
| 125 | 26 |

EXAMPLE 245

Intravenous effectiveness of
N-alpha-[3-(L-alpha-glutamylthio)-2-D-methylpropanoyl]-L-proline.

The intravenous effectiveness of the named compound was examined by following the procedure described in Example 244 except that 1 μmole/kg of the drug was given intravenously. The results are shown below:

| Time After IV Administration (minutes) | Blood Pressure Response to 400 ng/kg of Angiotensin I (% of Control) |
|---|---|
| −5 | 100 (38 mm Hg) |
| +0.5 | 13 |
| 3 | 13 |
| 7 | 13 |
| 11 | 21 |
| 22 | 21 |
| 28 | 18 |
| 37 | 29 |
| 47 | 37 |
| 56 | 39 |
| 82 | 53 |
| 92 | 71 |

EXAMPLE 246

Oral effectiveness of the sodium salt of
N-alpha-[3-(N-alpha-benzoyl-D,L-phenylalanylthio)-2-D-methylpropanoyl]-L-proline Rats (150–190 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 400 ng/kg of angiotensin I in 20 μl of 0.9 g % NaCl; an amount of angiotensin I sufficient to raise mean arterial blood pressure by 45 mm Hg. After the responsiveness of a given rat to angiotensin I was established, the named compound at 10 μmol/kg (drug dissolved in 0.15 ml of $H_2O$ plus 10 μl of 1N $NaHCO_3$), was given via a stomach tube. At timed intervals, the effects of 400 ng/kg of angiotensin I on mean arterial blood pressure were tested. Results are shown below:

| Time After Oral Administration (minutes) | Blood Pressure Response to 400 ng/kg of Angiotensin I (% of Control) |
| --- | --- |
| −5 | 100 (45 mm Hg) |
| +5 | 82 |
| 10 | 33 |
| 15 | 24 |
| 20 | 27 |
| 30 | 27 |
| 40 | 22 |
| 50 | 24 |
| 60 | 27 |
| 90 | 36 |
| 120 | 44 |
| 150 | 62 |
| 180 | 60 |
| 210 | 71 |
| 240 | 73 |

EXAMPLE 247

Intravenous effectiveness of the potassium salt of N-alpha-[3-(N-alpha-benzoyl-D,L-phenylalanylthio)-2-D-methylpropanoyl]-L-proline.

The intravenous effectiveness of the named compound was examined by following the procedure described in Example 246 except that 1 μmole/Kg of the drug was given intravenously. The results are shown below:

| Time After IV Administration (minutes) | Blood Pressure Response to 400 ng/kg of Angiotensin I (% of Control) |
| --- | --- |
| −5 | 100 (54 mm Hg) |
| +5 | 46 |
| 10 | 37 |
| 15 | 41 |
| 20 | 37 |
| 30 | 44 |
| 40 | 50 |
| 50 | 39 |
| 60 | 46 |
| 90 | 52 |
| 120 | 59 |

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A compound having the formula $$R_1-A_1-S-B-A_2$$

wherein, $R_1$ is hydrogen or an acyl group consisting of hydrogen or a hydrocarbyl moiety linked to a carbonyl group;

$A_1$ is a residue of a carboxylic acid having at least one alpha-amino or alpha-imino group, is linked to $R_1$ through such an alpha-amino or alpha-imino group to form an amide linkage therewith and is linked to the sulfur atom through a carboxyl group to form a thiolester bond;

B represents a substituted or unsubstituted 2 to 4 carbon backbone chain which is in mercapto linkage with the sulfur atom and which includes a carbonyl group through which B is linked to a nitrogen atom of $A_2$ in amido relationship therewith; and $A_2$ is a carboxylic acid or lower alkyl ester or physiologically acceptable salt thereof which contains at least one amino- or imino-nitrogen atoms.

2. A method for reducing blood pressure in mammals which comprises administering to mammals in need thereof an effective amount of a compound having the formula $$R_1-A_1-S-B-A_2$$

wherein, $R_1$ is hydrogen or an acyl group consisting of hydrogen or a hydrocarbyl moiety linked to a carbonyl group;

$A_1$ is a residue of a carboxylic acid having at least one alpha-amino or alpha-imino group, is linked to $R_1$ through such an alpha-amino or alpha-imino group to form an amide linkage therewith and is linked to the sulfur atom through a carboxyl group to form a thiolester bond;

B represents a substituted or unsubstituted 2 to 4 carbon backbone chain which is in mercapto linkage with the sulfur atom and which includes a carbonyl group through which B is linked to a nitrogen atom of $A_2$ in amido relationship therewith; and $A_2$ is a carboxylic acid or lower alkyl ester or physiologically acceptable salt thereof which contains at least one amino- or imino-nitrogen atom.

* * * * *

UNITED STATES PATENT AND TRADEMARK OFFICE
CERTIFICATE OF CORRECTION

PATENT NO. : 4,745,124

DATED : May 17, 1988

INVENTOR(S) : James W. Ryan and Alfred Chung

It is certified that error appears in the above-identified patent and that said Letters Patent is hereby corrected as shown below:

Col. 14, line 42 delete H-alpha and insert -- N-alpha--.

Col 60, line 4 delete "N-alpha-(3-[1-amino-1-amino-1-cyclopentanecar-" and insert -- N-alpha-(3-[1-amino-1-cyclopentanecar- --

Col 68, line 33 delete "Table 11" and insert -- Table 11A--

UNITED STATES PATENT AND TRADEMARK OFFICE
CERTIFICATE OF CORRECTION

PATENT NO. : 4,745,124

DATED : May 17, 1988

INVENTOR(S) : James W. Ryan and Alfred Chung

Page 2 of 15

It is certified that error appears in the above-identified patent and that said Letters Patent is hereby corrected as shown below:

Col 67, line 13 delete "N-(5-Boc-amino-2-mer-" and insert --N-(5-N-Boc-amino-2-mer- --

Col 71, line 45 delete ")amino]-2-methylpropionic acid" and insert -- )amino]-2-methylpropanoic acid --

Col 84, line 39 delete "N-[3-(benzoyl-D-phenylalanylthio)-b" and insert -- N-[3-benzoyl-D-phenylalanylthio) --

Col 95, line 15 delete "Ala-ro" and insert -- Ala-Pro--

Cover Page - below References Cited insert the following omitted U.S. Patents:

| | | |
|---|---|---|
| 3,832,337 | 8/74 | Ondetti, et al. |
| 3,891,616 | 6/75 | Ondetti |
| 3,947,575 | 3/76 | Ondetti, et al. |
| 4,052,551 | 10/77 | Cushman, et al. |
| 4,053,651 | 10/77 | Ondetti, et al. |
| 4,046,889 | 9/77 | Ondetti |
| 4,113,715 | 9/78 | Ondetti, et al. |
| 4,154,840 | 5/79 | Ondetti, et al. |

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

| | | |
|---|---|---|
| 4,070,361 | 1/78 | Petrillo |
| 4,154,935 | 5/79 | Ondetti, et al. |
| 4,154,934 | 5/79 | Berstein, et al. |
| 4,129,566 | 1/79 | Ondetti, et al. |
| 4,108,886 | 8/78 | Ondetti, et al. |
| 4,053,651 | 10/77 | Ondetti, et al. |
| 4,113,715 | 9/78 | Ondetti, et al. |
| 4,146,611 | 3/79 | Ondetti, et al. |
| 4,116,962 | 9/78 | Ondetti, et al. |
| 4,261,895 | 4/81 | Wiskott, et al. |
| 4,283,407 | 8/81 | Malen, et al. |
| 4,303,583 | 12/81 | Kim, et al. |
| 4,304,771 | 12/81 | Suh, et al. |
| 4,350,704 | 9/82 | Hoefle, et al. |
| 4,356,183 | 10/82 | Iwao, et al. |
| 4,248,883 | 2/81 | Sawayma, et al. |
| 4,216,209 | 8/80 | Bellini, et al. |
| 4,356,182 | 10/82 | Krapcho |
| 4,179,568 | 12/79 | Cohen, et al. |
| 4,226,775 | 10/80 | McEvoy, et al. |
| 4,288,368 | 9/81 | Hangwitz |
| 4,331,806 | 5/82 | Haugwitz |

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

| | | |
|---|---|---|
| 4,299,769 | 11/81 | McEvoy |
| 4,105,789 | 8/78 | Ondetti |
| 4,151,172 | 4/79 | Ondetti, et al. |
| 4,154,937 | 5/29 | Cushman, et al. |
| 4,168,267 | 9/29 | Petrillo |
| 4,254,268 | 3/81 | Rovnyak |
| 4,252,943 | 2/81 | Krapcho |
| 4,241,076 | 12/80 | Ondetti, et al. |
| 4,237,129 | 12/80 | Ondetti, et al. |
| 4,237,134 | 12/80 | Ondetti, et al. |
| 4,234,489 | 11/80 | Ondetti, et al. |
| 4,221,912 | 9/80 | Ondetti, et al. |
| 4,221,804 | 9/80 | Rovnyak |
| 4,217,458 | 8/80 | Ondetti |
| 4,217,359 | 8/80 | Krapcho |
| 4,216,209 | 8/80 | Bellini, et al. |
| 4,211,786 | 7/80 | Rovnyak |
| 4,206,137 | 6/80 | Condon, et al. |
| 4,206,122 | 6/80 | Natarajan |
| 4,206,121 | 6/80 | Ondetti, et al. |
| 4,199,512 | 4/80 | Ondetti, et al. |
| 4,198,517 | 4/80 | Ondetti, et al. |

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

| | | |
|---|---|---|
| 4,198,515 | 4/80 | Ondetti, et al. |
| 4,198,509 | 4/80 | Ondetti |
| 4,192,878 | 3/80 | Ondetti |
| 4,186,268 | 1/80 | Petrillo |
| 4,179,434 | 12/79 | Ondetti, et al. |
| 4,177,277 | 12/79 | Ondetti, et al. |
| 4,173,704 | 11/79 | Ondetti, et al. |
| 4,112,119 | 9/78 | Ondetti, et al. |
| 4,127,729 | 11/78 | Ondetti |
| 4,128,721 | 12/78 | Ondetti |
| 4,129,571 | 12/78 | Ondetti, et al. |
| 4,140,786 | 2/79 | Ondetti, et al. |
| 4,140,797 | 2/79 | Ondetti, et al. |
| 4,140,864 | 2/79 | Ondetti, et al. |
| 4,154,736 | 5/79 | Ondetti, et al. |
| 4,154,936 | 5/79 | Ondetti, et al. |
| 4,154,942 | 5/79 | Ondetti, et al. |
| 4,154,960 | 5/79 | Ondetti, et al. |
| 4,156,084 | 5/79 | Ondetti, et al. |
| 4,156,786 | 5/79 | Ondetti, et al. |
| 4,165,320 | 8/79 | Ondetti, et al. |
| 4,175,199 | 11/79 | Ondetti, et al. |

UNITED STATES PATENT AND TRADEMARK OFFICE
CERTIFICATE OF CORRECTION

PATENT NO. : 4,745,124

DATED : May 17, 1988

INVENTOR(S) : James W. Ryan and Alfred Chung

It is certified that error appears in the above-identified patent and that said Letters Patent is hereby corrected as shown below:

| | | |
|---|---|---|
| 4,176,235 | 11/79 | Ondetti, et al. |
| 4,178,291 | 12/79 | Ondetti, et al. |
| 4,192,945 | 3/80  | Ondetti |
| 4,220,791 | 9/80  | Rovnyak |
| 4,225,495 | 9/80  | Ondetti |
| 4,235,885 | 11/80 | Sudeen, et al. |
| 4,263,293 | 4/81  | Sudeen, et al. |
| 4,266,065 | 5/81  | Rovnyak |
| 4,282,235 | 2/81  | Ondetti |
| 4,281,561 | 8/81  | Petrillo, et al. |
| 4,284,779 | 8/81  | Ondetti, et al. |
| 4,284,780 | 8/81  | Ondetti, et al. |
| 4,291,040 | 9/81  | Krapcho |
| 4,296,113 | 10/81 | Ondetti |
| 4,297,275 | 10/81 | Sudeen, et al. |
| 4,321,392 | 3/82  | Ryono, et al. |
| 4,339,600 | 7/82  | Ondetti, et al. |
| 4,154,946 | 5/79  | Ondetti, et al. |
| 4,308,392 | 12/79 | Petrillo, et al. |
| 4,316,906 | 8/78  | Ondetti, et al. |
| 4,330,548 | 1/80  | Ondetti, et al. |
| 4,091,024 | 12/76 | Ondetti |

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

| | | |
|---|---|---|
| 4,146,611 | 12/77 | Ondetti |
| 4,105,776 | 12/76 | Ondetti |
| 3,865,934 | 4/73 | Plotnikoff |
| 3,973,006 | 2/75 | Ondetti |
| 3,976,770 | 2/75 | Bumpus |
| 3,891,696 | 11/73 | Bodor |
| 4,483,861 | 11/84 | Iwao |

Cover Page - Insert the following omitted Foreign Patents:

| | | |
|---|---|---|
| WO800444 | | PCT |
| 2407204 | 5/79 | France |
| 155166 | 78 | Japan |
| 144079 | 79 | Japan |
| 2018248 | | United Kingdom |
| 2066240A | | United Kingdom |
| 41632 | 78 | Japan |
| 49657 | 78 | Japan |
| 81116 | 78 | Japan |
| 135093 | 78 | Japan |
| 12519 | 78 | Japan |
| 18812 | 79 | Japan |

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

| | | |
|---|---|---|
| 2703828 | 77 | West Germany |
| 2457463 | 76 | West Germany |

Cover Page - insert the following omitted References

Buxton et al., J. Chem. Soc. 366 (1954), "Studies upon -Trifluoro-methylacrylic Acid, -Trifluoromethylpropionic Acid, and Some Derived Compounds"

Carter et al., J. Biol. Chem. 138:627 (1941), "Benzoylation of Amino Acids"

Cushman et al., Experientia 29:1032 (1973), Inhibition of Angiotensin-Converting Enzyme by Analogs of Peptides from Bothrops jararaca Venom"

Cushman et al., Biochemistry 16: 5484 (1977) "Design of Potent Competive Inhibitors of Angiotensin-Converting Enzyme. Carboxyalkanoyl and Mercaptoalkanovl Amino Acids"

Dorer et al., Biochim. Biophys. Acta., 429:220 (1976) "Kinetic Properties of Pulmonary Angiotensin-converting Enzyme. Hydrolysis of Hippurylglycylglycine."

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

Engel et al., Proc. Soc. Exp. Biol. Med. 143: 483 (1973) "Effects of the Nonapeptide SQ 20881 on Blood Pressure of Rats with Experimental Renovascular Hypertension"

Gavras, et al., New Eng. J. Med. 291: 817 (1974) "An Angiotensin Converting-Enzyme Inhibitor to Identify and Treat Vasoconstrictor and Volume Factors in Hypertensive Patients"

Gavras et al., New Eng. J. Med. 298: 991 (1978) "Antihypertensive Effect of the Oral Angiotensin Converting-Enzyme Inhibitor SQ 14225 In Man"

Goodman et al., The Pharmacological Basis of Theraputics
The MacMillian Co., New York (1965) 105-128 "Hypnotics and Sedatives"

Jager et al., Chem. Ber. 103: 1727 (1970) "Der Adamantyl-(1)-oxycarbonyl-Rest als Schutzgruppe fur die Guanidinofunktion des Arginins"

UNITED STATES PATENT AND TRADEMARK OFFICE
CERTIFICATE OF CORRECTION

PATENT NO. : 4,745,124

DATED : May 17, 1988

INVENTOR(S) : James W. Ryan and Alfred Chung

It is certified that error appears in the above-identified patent and that said Letters Patent is hereby corrected as shown below:

Klosterman et al., Biochemistry 6: 170 (1967) "Isolation, Characterization, and Synthesis of Linatine. A Vitamin $B_6$ Antagonist from Flaxseed (Linum usitatissumum)"

Lehninger, Biochemistry, 2nd ed. Worth Publications, Inc. New York (1975) 189-195 "Kinetics of Enzyme-Catalyzed Reactions: The Michaelis-Menten Equation"

Litjinsky et al., Tetrahedron 26:5137 (1970) "Nonribosomal Polypeptide Synthesis on Polyenzyme Templates"

Lipmann, Accounts Chem. Res. 6:361 (1973) "The Preparation and Properties of Some Nitrosamino Acids"

Methoden der Organischen Chem (Houben-Weyl) Vol. XV. Part I, pp. 376-380 (1974) "Der Verknupfungaschritt"

Methoden der Organischen Chem (Houben-Weyl) Vol XV Part II, pp. 1-12 (1974) "die Herstellung der Peptidbindung"

Nagasawa et al., J. Med. Chem. 16:583 (1973) "A New Method for Nitrosation of Proline and Related sec- -Amino

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

Acids to N-Nitrosamino Acids with Possible Oncogenic Activity"

Ondetti et al., Science 196:441 (1977) "Design of Specific Inhibitors of Angiotensin-Conversting Enzyme: New Class of Orally Active Antihypertensive Agents"

Ryan et al., Biochem J. 167: 501 (1977) "A Simple Radioassay for Angiotensin-Converting Enzyme"

Ryan et al., Tissue and Cell 10:555 (1978) "New Substrates for the Radioassay of Angiotensin Converting Enzyme of Endothelial Cells in Culture"

Ricci et al., Anal. Biochem. 79:610 (1977) "A New Spot Test for Sulfhydryl-Containing Compounds"

Pfister et al., J. Amer. Chem. Soc. 71:1096 (1949) "The Synthesis of DL-Threonone, I. From  -Bromo-B-methoxy-n-butyric Acid and Derivatives"

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

Mita et al., Chem. Pharm. Bull. 26 (4): 1333-1335 (1978) "New Sulfhydryl Compounds with Potent Antihypertensive Activities"

Kripalani, et al., Clin. Pharmacol Ther., 27(5): 636-641 (May, 1980) "Disposition of captopril in normal subjects"

Gavras et al., Compr. Ther. 6:14 (1980) "Angiotensin Inhibitors for Hypertension"

Cushman et al., Fed Proc. 38: 2778 (1979)

Cheung H.S. et al., J. Bio. Chem. 255: 401 (1979) "Binding of Peptide Substrates and Inhibitors of Angiotensin-converting Enzyme"

Cushman D.W., et al., Progr. Cardiovasc. Dis. 21:176 (1978)

[Editorial] Br. Med. J. 281: 60 (1980) "Inhibitors of angiotensin I converting enzyme for treating hypertension"

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

Dipalma, J.R. Am. Fam. Physician 22 (1980) "Angiotensin-converting Enzyme Inhibitors"

Cushman et al., Biochem. Pharmacol. 29: 1871 (1980) "Inhibitors of Angiotensin-Converting Enzyme for Treatment of Hypertension"

Cushman et al., Adv. Exp. Biol. 130:199 (1980) "Inhibitors of Angiotensin-Converting Enzyme"

Oparil et al., Circ. Res. 32: 415 (1973) "Substrate Requirements for Angiotensin I Conversion *in Vivo* and *In Vitro*"

Oparil et al., Circ. Res. 29: 682 (1971) "Mechanism of Pulmonary Conversion of Angiotensin I to Angiotensin II in the Dog"

Dorer et al., Biochem. J. 141: 915 (1974) "Hydrolysis of Bradykinin and Its Higher Homologues by Angiotensin-Converting Enzyme"

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

Merrifield, R.B. Adv. Enzym. 32: 221 (1969) "Solid-Phase Peptide Synthesis"

Engel, Proc. Soc. Exp. Biol. Med. 143:483 (1973) "Effects of the Nonapeptide SQ 20881 on Blood Pressure of Rats with Experimental Renovascular Hypertension (37348)

Fischer et al., Ber. Vol 33 (1900) pp. 2383-2393.

Fisher FEBS Letters Vol 107 (1979) pp. 273-275.

Lehninger, A. Biochemistry, Worth Publishers, Inc. New York (1970) pp. 153-157.

Cushman et al., Fed. Proc. 38, 2778 (1979).

Sharpless, S.K. "Hypnotics and Sedatives", The Pharmacological Basis of Therapeautics, The MacMillian Co., (1965), pp. 105-128

Kripalani, K.J. et al., Abstracts, Joint Meeting of ASPET/SOT, August 13-17, 1978.

UNITED STATES PATENT AND TRADEMARK OFFICE
CERTIFICATE OF CORRECTION

PATENT NO. : 4,745,124
DATED : May 17, 1988
INVENTOR(S) : James W. Ryan and Alfred Chung It is certified that error appears in the above-identified patent and that said Letters Patent is hereby corrected as shown below:

Singhvi, S.M. et al., Abstracts, Joint Meeting of ASPET/SOT, August 13-17, 1978

Wong, K.K. and Dreyfuss, J. Abstracts, Joint Meeting of ASPET/SOT, August 13-17, 1978

Signed and Sealed this

Eighteenth Day of September, 1990

Attest:

HARRY F. MANBECK, JR.

Attesting Officer      Commissioner of Patents and Trademarks